(12) United States Patent
Zhang et al.

(10) Patent No.: US 10,443,103 B2
(45) Date of Patent: Oct. 15, 2019

(54) CHEMOTHERAPY REGIMEN SELECTION

(71) Applicant: Innomedicine, LLC, Tallahassee, FL (US)

(72) Inventors: Jinfeng Zhang, Tallahassee, FL (US); Kaixian Yu, Tallahassee, FL (US); Amy Qingxiang Sang, Tallahassee, FL (US)

(73) Assignee: Innomedicine, LLC, Tallahassee, FL (US)

( * ) Notice: Subject to any disclaimer, the term of this patent is extended or adjusted under 35 U.S.C. 154(b) by 0 days.

(21) Appl. No.: 15/248,814

(22) Filed: Aug. 26, 2016

(65) Prior Publication Data
US 2017/0073769 A1  Mar. 16, 2017

Related U.S. Application Data

(60) Provisional application No. 62/219,252, filed on Sep. 16, 2015.

(51) Int. Cl.
*C12Q 1/6886* (2018.01)
*G06F 19/18* (2011.01)
*C40B 30/02* (2006.01)
*A61K 31/704* (2006.01)
*A61K 31/337* (2006.01)
*G01N 33/574* (2006.01)
*G16H 50/50* (2018.01)
*G06F 19/00* (2018.01)

(52) U.S. Cl.
CPC ......... *C12Q 1/6886* (2013.01); *A61K 31/337* (2013.01); *A61K 31/704* (2013.01); *C40B 30/02* (2013.01); *G01N 33/57415* (2013.01); *G06F 19/00* (2013.01); *G06F 19/18* (2013.01); *G16H 50/50* (2018.01); *C12Q 2600/106* (2013.01); *C12Q 2600/158* (2013.01); *G01N 2800/52* (2013.01)

(58) Field of Classification Search
None
See application file for complete search history.

(56) References Cited

PUBLICATIONS

Couzin-Frankel (Science Magazine (Aug. 2010) pp. 614-615).*
Baggerly (The Annals of Applied Sciences (2009) vol. 3 pp. 1309-1334).*
Cheung et al (Nature Genetics, 2003, vol. 33, pp. 422-425).*
Saito-Hisaminato et al. (DNA research (2002) vol. 9, pp. 35-45).*
Benner et al (Trends in Genetics (2001) vol. 17, pp. 414-418.*
Greenbaum et al (Genome Biology 2003, vol. 4, article 117, pp. 1-8).*
May et al (Science (1988) vol. 241, p. 1441).*
Moreno-Aspitia( Journal of Clinical Oncology (2008) vol. 27, pp. 11-15).*
Liaw ( R news (2002) vol. 2/3, pp. 18-22).*

* cited by examiner

*Primary Examiner* — Steven Pohnert
(74) *Attorney, Agent, or Firm* — Xingsheng Wang; Hon-Man Lee

(57) ABSTRACT

The present invention provides, inter alia, kits for selecting a chemotherapy regimen for a subject. The kits comprise one or more components for detecting the expression of at least one gene from the group of SLC12A7, GZMB, TAF6L, NFIB, METRN, ROPN1B, TTK, CCND1, PTTG1, H2AFZ, WDR45L, DEK, MCM2, USP1, CDT1, TMEM97, RER1, MCM6, LZTFL1, C11orf17, CCL5, XCL1, XCL2, MELK, CTSL2, TPX2, AURKA, CDKN2C, BRP44, PNP, SMC4, NR4A2, C3orf37, MTPAP, CDC25B, ABCF1, MTAP, SNAPC3, RANBP9, COIL, FAM86B1, ITGA6, S100P, RANBP1, PRSS16, SMARCA2, STK24, TSPYL5, SRI, LRP12, CENPF, TUBD1, KIAA1324, DBF4, CCNA2, DLGAP5, FHL1, SIRT3, GTSE1, PCNA, CCNE2, CHD3, CAP1, GPM6B, GUSBP3, GNAI3, LMO4, PSRC1, USP1, STK38, BAT2L1, PMP22, NME5, CENPA, BANK1, and derivatives thereof. Methods for selecting a chemotherapy regimen for a subject are also provided.

2 Claims, 47 Drawing Sheets

CHEMOTHERAPY REGIMEN SELECTION

FIELD OF INVENTION

The present invention relates generally to cancer therapy. In one embodiment, there are provided methods and systems for selecting a chemotherapy regimen for a subject, as well as methods and systems for predicting the efficacy of a chemotherapy regimen for a subject. Kits for selecting a chemotherapy regimen for a subject are also provided.

BACKGROUND OF THE INVENTION

Breast cancer is a very heterogeneous disease (The Cancer Genome Atlas Network, et al., 2012). In the past, validated clinicopathologic prognostic factors, such as tumor size, lymph node involvement, histologic grade, and age have been widely used by clinicians to guide treatment decisions. This approach resulted in significant numbers of over-treated and undertreated patients. It is well known that patients with similar pathological characteristics can have very different responses toward certain therapies, although the mechanisms of such responses have been poorly understood. More recently, evaluation of the status of estrogen receptor (ER), human epidermal growth factor receptor 2 (HER2) gene, and progesterone receptor (PR) has become routine practice because each has been validated as a prognostic marker. The development of high-throughput genomics technologies such as microarrays and next generation sequencing has allowed more personalized cancer therapy (PCT) based on patients' genomic profiles (Oakman, et al., 2010, Dotan, et al., 2010, Eng-Wong, et al., 2010). The genomic information obtained using these technologies can be much better predictors of treatment responses than the commonly used clinical variables. In PCT, a set of genetic markers from the large volume of genomic information needs to be carefully selected, which is often combined with clinical information, to build models to predict the likely outcome of a patient's current standing or response to a particular treatment. For chemotherapy, two decisions need to be made: whether chemotherapy should be received and, if so, which chemotherapy should be received. Both decision making steps can potentially benefit from PCT. Many studies have found gene signatures for predicting overall survival or recurrence of breast cancer (van de Vijver, et al., 2002, Paik, et al., 2006, Wang, et al., 2005, van't Veer, et al., 2002, Mook, et al., 2007, Strayer, et al., 2010, Buyse, et al., 2006, Foekens, et al., 2006, Look, et al., 2002, Harbeck, et al., 2013), which can be used to provide guidance on whether a more aggressive treatment strategy, such as chemotherapy, should be taken. For example, ONCOTYPE DX, a commercially available diagnostic test based on the expression of a 21-gene panel, has been widely used in the prognosis of breast cancer. Studies have also been performed to predict responses for a particular type of treatment or for a population with mixed treatments without stratification by treatment types (Hatzis, et al., 2011, Graeser, et al., 2010, Shen, et al., 2012, Esserman, et al., 2012, Miyake, et al., 2012, Lips, et al., 2012, Hess, et al., 2006, Takada, et al., 2012, Albain, et al., 2010, Liu, et al., 2012). No studies in the past has developed a personalized treatment strategy to select among multiple chemotherapy regimens. When chemotherapy is to be received, patients still lack guidance on which regimen is the most effective for them. An interesting and important problem, which few studies in the past have addressed, is how much PCT can benefit patients when they decide to receive one of the currently available regimens. In principle, if all patients respond similarly to currently available regimens, then PCT will not be useful at present, although it may become useful when new treatments are introduced. Another challenge is, given a significant number of patients who respond differently to at least two regimens (those who can benefit from PCT), identifying and assigning those patients to the most effective regimen. Hence, there is a need to develop improved methods for selecting suitable and effective chemotherapy regimens for breast cancer patients.

SUMMARY OF THE INVENTION

Herein, data was reanalyzed from several previous studies in which breast cancer patients were treated with neoadjuvant chemotherapy. Chemotherapies can be given at different stages of breast cancer: before surgery (also called neoadjuvant chemotherapy), after surgery and after metastasis. Neoadjuvant chemotherapy is often used to shrink tumors to make them more operable. There are two main categories of cytotoxic chemotherapy drugs for breast cancer: anthracyclines and taxanes. Many different combinations of the two types of drugs have been used for treating breast cancer, despite the fact that no effective guidelines are available for the selection of a specific regimen for a patient (Dotan, et al., 2010). Herein, data was collected from 1111 breast cancer patients from GEO database (Gene Expression Omnibus (Edgar, et al., 2002, Barrett, et al., 2013)), where clinical information including responses to chemotherapy and gene expression data are available. The responses were coded as pCR (pathologic complete response) or RD (residual disease). pCR has been shown to be a potential surrogate marker for survival (Kaufmann, et al., 2006, Kuerer, et al., 1999, von Minckwitz, et al., 2012) and used as a measure for chemosensitivity (Strayer, et al., 2010). Among the 1111 patients, 21.2% of them have pCR and the rest have RD as their responses. Using pCR/RD as the measure of outcome, whether the current rate of pCR can be improved by personalized regimen selection using genomic variables is studied herein. Patients were divided into three regimen groups: patients treated with anthracycline only (A group), patients treated with anthracycline and paclitaxel (TA group), and patients treated with anthracycline and docetaxel (TxA group). Random Forest models were trained for the three groups and 10-fold cross validation was used to assess the performance of the models. Both clinical variables, including ER, PR and HER2 status, and genetic variables (gene expression) were used as predictors. Models with both genetic and clinical variables were found to perform better in general than models with only clinical variables. Three genes were found to be significant predictors of pCR for the A group, 5 genes for the TA group, and 11 genes for the TxA group. It was also found that personalized regimen selection using genetic variables can benefit a substantial number of patients with the currently available chemotherapy regimens. Based on the predicted responses from the models, patients were reassigned to the regimen for which they are predicted to have the highest probability of pCR. The new assignment approach, called PERS (PErsonalized Regimen Selection), was estimated to have a 39.1% pCR rate, an 84% increase, compared to a 21.2% pCR rate obtained using the original assignments. It was found that 17.28% of patients were over-treated and 9.63% of patients were undertreated. Based on the study population, patients who receive TxA regimen have a higher rate of pCR (33.1%) than those who receive TA regimen (19.7%) and those who receive A regimen (8.6%). However, to maximize the rate of pCR, regimens should be selected based both on a patient's genomic and clinical variables. Patients were further stratified by the status of HER2, ER, and lymph node status, and similar results were obtained.

In one embodiment of the present invention, there is provided a kit for selecting a chemotherapy regimen for a subject. The kit comprises one or more agents for detecting the expression of at least one gene of the following: SLC12A7, GZMB, TAF6L, NFIB, METRN, ROPN1B, TTK, CCND1, PTTG1, H2AFZ, WDR45L, DEK, MCM2, USP1, CDT1, TMEM97, RER1, MCM6, LZTFL1, C11orf17, CCL5, XCL1, XCL2, MELK, CTSL2, TPX2, AURKA, CDKN2C, BRP44, PNP, SMC4, NR4A2, C3orf37, MTPAP, CDC25B, ABCF1, MTAP, SNAPC3, RANBP9, COIL, FAM86B1, ITGA6, S100P, RANBP1, PRSS16, SMARCA2, STK24, TSPYL5, SRI, LRP12, CENPF, TUBD1, KIAA1324, DBF4, CCNA2, DLGAP5, FHL1, SIRT3, GTSE1, PCNA, CCNE2, CHD3, CAP1, GPM6B, GUSBP3, GNAI3, LMO4, PSRC1, USP1, STK38, BAT2L1, PMP22, NME5, CENPA, BANK1, and derivatives thereof.

In another embodiment, the present invention provides a method for predicting the efficacy of a chemotherapy regimen for a subject. The method comprises: (a) determining, from a sample derived from the subject, the expression of at least one biomolecule predictive of the efficacy of a chemotherapy regimen; (b) applying a model to the expression of said biomolecule(s) to calculate a predicted probability of pathological complete response (pCR) to a chemotherapy regimen; (c) classifying the predicted probability of pathological complete response (pCR) into a set of probability intervals (PIs) associated with the chemotherapy regimen; and (d) determining a quantitative measure of chemotherapy outcome for the chemotherapy regimen, wherein the quantitative measure of chemotherapy outcome is predictive of the efficacy of the chemotherapy regimen for the subject.

In another embodiment, the present invention provides a method for predicting the efficacy of a chemotherapy regimen for a subject. The method comprises determining, from a sample derived from the subject, the expression of at least two biomolecules selected from the following: SLC12A7, GZMB, TAF6L, NFIB, METRN, ROPN1B, TTK, CCND1, PTTG1, H2AFZ, WDR45L, DEK, MCM2, USP1, CDT1, TMEM97, RER1, MCM6, LZTFL1, C11orf17, CCL5, XCL1, XCL2, MELK, CTSL2, TPX2, AURKA, CDKN2C, BRP44, PNP, SMC4, NR4A2, C3orf37, MTPAP, CDC25B, ABCF1, MTAP, SNAPC3, RANBP9, COIL, FAM86B1, ITGA6, S100P, RANBP1, PRSS16, SMARCA2, STK24, TSPYL5, SRI, LRP12, CENPF, TUBD1, KIAA1324, DBF4, CCNA2, DLGAP5, FHL1, SIRT3, GTSE1, PCNA, CCNE2, CHD3, CAP1, GPM6B, GUSBP3, GNAI3, LMO4, PSRC1, USP1, STK38, BAT2L1, PMP22, NME5, CENPA, BANK1, and derivatives thereof.

In another embodiment, there is provided a method for predicting the efficacy of a chemotherapy regimen for a subject wherein the chemotherapy regimen comprises anthracycline without paclitaxel or docetaxel. The method comprises: (a) determining, from a sample derived from the subject, the expression of at least one biomolecule selected from: SLC12A7, GZMB, TAF6L, and derivatives thereof; (b) applying a model to the expression of said biomolecule (s) to calculate a predicted probability of pathological complete response (pCR) to a chemotherapy regimen; (c) classifying the predicted probability of pathological complete response (pCR) into a set of probability intervals (PIs) associated with the chemotherapy regimen; and (d) determining a quantitative measure of chemotherapy outcome for the chemotherapy regimen, wherein the quantitative measure of chemotherapy outcome is predictive of the efficacy of the chemotherapy regimen for the subject.

In another embodiment, there is provided a method for predicting the efficacy of a chemotherapy regimen for a subject, wherein the chemotherapy regimen comprises anthracycline with paclitaxel but without docetaxel. The method comprises: (a) determining, from a sample derived from the subject, the expression of at least one biomolecule selected from: NFIB, METRN, ROPN1B, TTK, CCND1, and derivatives thereof; (b) applying a model to the expression said biomolecule(s) to calculate a predicted probability of pathological complete response to a chemotherapy regimen; (c) classifying the predicted probability of pathological complete response (pCR) into a set of probability intervals (PIs) associated with the chemotherapy regimen; and (d) determining a quantitative measure of chemotherapy outcome for the chemotherapy regimen, wherein the quantitative measure of chemotherapy outcome is predictive of the efficacy of the chemotherapy regimen for the subject.

In another embodiment of the present invention, there is provided a method for predicting the efficacy of a chemotherapy regimen for a subject, wherein the chemotherapy regimen comprises anthracycline with docetaxel but without paclitaxel. The method comprises: (a) determining, from a sample derived from the subject, the expression of at least one biomolecule selected from the following: PTTG1, H2AFZ, WDR45L, DEK, MCM2, USP1, CDT1, TMEM97, RER1, MCM6, LZTFL1, and derivatives thereof; (b) applying a model to the expression of said biomolecule(s) to calculate a predicted probability of pathological complete response (pCR) to a chemotherapy regimen; (c) classifying the predicted probability of pathological complete response (pCR) into a set of probability intervals (PIs) associated with the chemotherapy regimen; and (d) determining a quantitative measure of chemotherapy outcome for the chemotherapy regimen, wherein the quantitative measure of chemotherapy outcome is predictive of the efficacy of the chemotherapy regimen for the subject.

In another embodiment, the present invention provides a method for predicting the efficacy of a chemotherapy regimen for a HER2-negative subject, wherein the chemotherapy regimen comprises anthracycline without paclitaxel or docetaxel. The method comprises: (a) determining, from a sample derived from the subject, the expression of at least one biomolecule selected from the following: SLC12A7, GZMB, C11orf17, TAF6L, CCL5, XCL1, XCL2, and derivatives thereof; (b) applying a model to the expression of said biomolecule(s) to calculate a predicted probability of pathological complete response (pCR) to a chemotherapy regimen; (c) classifying the predicted probability of pathological complete response (pCR) into a set of probability intervals (PIs) associated with the chemotherapy regimen; and (d) determining a quantitative measure of chemotherapy outcome for the chemotherapy regimen, wherein the quantitative measure of chemotherapy outcome is predictive of the efficacy of the chemotherapy regimen for the subject.

In another embodiment, the present invention provides a method for predicting the efficacy of a chemotherapy regimen for a HER2-negative subject, wherein the chemotherapy regimen comprises anthracycline with paclitaxel but without docetaxel. The method comprises: (a) determining, from a sample derived from the subject, the expression of at least one biomolecule selected from the following: NFIB, ROPN1B, TTK, MELK, CTSL2, METRN, and derivatives thereof; (b) applying a model to the expression of said biomolecule(s) to calculate a predicted probability of pathological complete response (pCR) to a chemotherapy regimen; (c) classifying the predicted probability of pathological complete response (pCR) into a set of probability intervals (PIs) associated with the chemotherapy regimen; and (d) determining a quantitative measure of chemotherapy outcome for the chemotherapy regimen, wherein the quantitative measure of chemotherapy outcome is predictive of the efficacy of the chemotherapy regimen for the subject.

In another embodiment, the present invention provides a method for predicting the efficacy of a chemotherapy regimen for a HER2-negative subject, wherein the chemotherapy regimen comprises anthracycline with docetaxel but without paclitaxel. The method comprises: (a) determining, from a sample derived from the subject, the expression of at least one biomolecule selected from the following: TPX2, PTTG1, MCM2, MCM6, AURKA, CDKN2C, BRP44, H2AFZ, PNP, SMC4, DEK, TMEM97, NR4A2, C3orf37, LZTFL1, MTPAP, CDC25B, ABCF1, and derivatives thereof; (b) applying a model to the expression of said biomolecule(s) to calculate a predicted probability of pathological complete response (pCR) to a chemotherapy regimen; (c) classifying the predicted probability of pathological complete response (pCR) into a set of probability intervals (PIs) associated with the chemotherapy regimen; and (d) determining a quantitative measure of chemotherapy outcome for the chemotherapy regimen, wherein the quantitative measure of chemotherapy outcome is predictive of the efficacy of the chemotherapy regimen for the subject.

In another embodiment of the present invention, there is provided a method for predicting the efficacy of a chemotherapy regimen for a HER2-negative, ER-negative subject, wherein the chemotherapy regimen comprises anthracycline with paclitaxel and without docetaxel. The method comprises: (a) determining, from a sample derived from the subject, the expression of at least one biomolecule selected from the following: NFIB, MTAP, SNAPC3, RANBP9, COIL, FAM86B1, ITGA6, S100P, RANBP1, PRSS16, SMARCA2, STK24, and derivatives thereof; (b) applying a model to the expression of said biomolecule(s) to calculate a predicted probability of pathological complete response (pCR) to a chemotherapy regimen; (c) classifying the predicted probability of pathological complete response (pCR) into a set of probability intervals (PIs) associated with the chemotherapy regimen; and (d) determining a quantitative measure of chemotherapy outcome for the chemotherapy regimen, wherein the quantitative measure of chemotherapy outcome is predictive of the efficacy of the chemotherapy regimen for the subject.

In another embodiment, there is provided a method for predicting the efficacy of a chemotherapy regimen for a HER2-negative, ER-negative subject, wherein the chemotherapy regimen comprises anthracycline with docetaxel and without paclitaxel. The method comprises: (a) determining, from a sample derived from the subject, the expression of at least one biomolecule selected from the following: TSPYL5, SRI, and derivatives thereof; (b) applying a model to the expression of said biomolecule(s) to calculate a predicted probability of pathological complete response (pCR) to a chemotherapy regimen; (c) classifying the predicted probability of pathological complete response (pCR) into a set of probability intervals (PIs) associated with the chemotherapy regimen; and (d) determining a quantitative measure of chemotherapy outcome for the chemotherapy regimen, wherein the quantitative measure of chemotherapy outcome is predictive of the efficacy of the chemotherapy regimen for the subject.

In another embodiment, the present invention provides a method for predicting the efficacy of a chemotherapy regimen for a HER2-negative, ER-positive subject, wherein the chemotherapy regimen comprises anthracycline and paclitaxel but without docetaxel. The method comprises: (a) determining, from a sample derived from the subject, the expression of at least one biomolecule selected from the group consisting of LRP12, CENPF, TUBD1, KIAA1324, TTK, and derivatives thereof; (b) applying a model to the expression of said biomolecule(s) to calculate a predicted probability of pathological complete response (pCR) to a chemotherapy regimen; (c) classifying the predicted probability of pathological complete response (pCR) into a set of probability intervals (PIs) associated with the chemotherapy regimen; and (d) determining a quantitative measure of chemotherapy outcome for the chemotherapy regimen, wherein the quantitative measure of chemotherapy outcome is predictive of the efficacy of the chemotherapy regimen for the subject.

In another embodiment, there is provided a method for predicting the efficacy of a chemotherapy regimen for a HER2-negative, ER-positive subject, wherein the chemotherapy regimen comprises anthracycline and docetaxel without paclitaxel. The method comprises: (a) determining, from a sample derived from the subject, the expression of at least one biomolecule selected from the following: DBF4, DEK, CDC25B, CCNA2, DLGAP5, MCM2, CDKN2C, FHL1, SIRT3, GTSE1, PCNA, CCNE2, and derivatives thereof; (b) applying a model to the expression of said biomolecule(s) to calculate a predicted probability of pathological complete response (pCR) to a chemotherapy regimen; (c) classifying the predicted probability of pathological complete response (pCR) into a set of probability intervals (PIs) associated with the chemotherapy regimen; and (d) determining a quantitative measure of chemotherapy outcome for the chemotherapy regimen, wherein the quantitative measure of chemotherapy outcome is predictive of the efficacy of the chemotherapy regimen for the subject.

In another embodiment, there is provided a method for predicting the efficacy of a chemotherapy regimen for a HER2-negative, lymph node-negative subject, wherein the chemotherapy regimen comprises anthracycline and paclitaxel without docetaxel. The method comprises: (a) determining, from a sample derived from the subject, the expression of at least one biomolecule selected from the following: CHD3, CAP1, GPM6B, GUSBP3, and derivatives thereof; (b) applying a model to the expression of said biomolecule(s) to calculate a predicted probability of pathological complete response (pCR) to a chemotherapy regimen; (c) classifying the predicted probability of pathological complete response (pCR) into a set of probability intervals (PIs) associated with the chemotherapy regimen; and (d) determining a quantitative measure of chemotherapy outcome for the chemotherapy regimen, wherein the quantitative measure of chemotherapy outcome is predictive of the efficacy of the chemotherapy regimen for the subject.

In another embodiment, there is provided a method for predicting the efficacy of a chemotherapy regimen for a HER2-negative, lymph node-negative subject, wherein the chemotherapy regimen comprises anthracycline and docetaxel without paclitaxel. The method comprises: (a) determining, from a sample derived from the subject, the expression of at least one biomolecule selected from the following: CDKN2C, GNAI3, LMO4, PSRC1, USP1, STK38, and derivatives thereof; (b) applying a model to the expression of said biomolecule(s) to calculate a predicted probability of pathological complete response (pCR) to a chemotherapy regimen; (c) classifying the predicted probability of pathological complete response (pCR) into a set of probability intervals (PIs) associated with the chemotherapy regimen; and (d) determining a quantitative measure of chemotherapy outcome for the chemotherapy regimen, wherein the quantitative measure of chemotherapy outcome is predictive of the efficacy of the chemotherapy regimen for the subject.

In another embodiment, there is provided a method for predicting the efficacy of a chemotherapy regimen for a HER2-negative, lymph node-positive subject, wherein the chemotherapy regimen comprises anthracycline and paclitaxel without docetaxel. The method comprises: (a) determining, from a sample derived from the subject, the expression of at least one biomolecule selected from the following: NFIB, ROPN1B, and derivatives thereof; (b) applying a model to the expression of said biomolecule(s) to calculate a predicted probability of pathological complete response (pCR) to a chemotherapy regimen; (c) classifying the predicted probability of pathological complete response (pCR) into a set of probability intervals (PIs) associated with the chemotherapy regimen; and (d) determining a quantitative measure of chemotherapy outcome for the chemotherapy regimen, wherein the quantitative measure of chemotherapy outcome is predictive of the efficacy of the chemotherapy regimen for the subject.

In another embodiment, there is provided a method for predicting the efficacy of a chemotherapy regimen for a HER2-negative, lymph node-positive subject, wherein the chemotherapy regimen comprises anthracycline and docetaxel without paclitaxel. The method comprises: (a) determining, from a sample derived from the subject, the expression of at least one biomolecule selected from the following: TPX2, BAT2L1, PMP22, PTTG1, NME5, CENPA, BANK1, and derivatives thereof; (b) applying a model to the expression of said biomolecule(s) to calculate a predicted probability of pathological complete response (pCR) to a chemotherapy regimen; (c) classifying the predicted probability of pathological complete response (pCR) into a set of probability intervals (PIs) associated with the chemotherapy regimen; and (d) determining a quantitative measure of chemotherapy outcome for the chemotherapy regimen, wherein the quantitative measure of chemotherapy outcome is predictive of the efficacy of the chemotherapy regimen for the subject.

In another embodiment, there is provided a method for selecting a chemotherapy regimen for a subject. The method comprises: (a) determining, from a sample derived from the subject, the expression of at least two biomolecules selected from the following: SLC12A7, GZMB, TAF6L, NFIB, METRN, ROPN1B, TTK, CCND1, PTTG1, H2AFZ, WDR45L, DEK, MCM2, USP1, CDT1, TMEM97, RER1, MCM6, LZTFL1, C11orf17, CCL5, XCL1, XCL2, MELK, CTSL2, TPX2, AURKA, CDKN2C, BRP44, PNP, SMC4, NR4A2, C3orf37, MTPAP, CDC25B, ABCF1, MTAP, SNAPC3, RANBP9, COIL, FAM86B1, ITGA6, S100P, RANBP1, PRSS16, SMARCA2, STK24, TSPYL5, SRI, LRP12, CENPF, TUBD1, KIAA1324, DBF4, CCNA2, DLGAP5, FHL1, SIRT3, GTSE1, PCNA, CCNE2, CHD3, CAP1, GPM6B, GUSBP3, GNAI3, LMO4, PSRC1, USP1, STK38, BAT2L1, PMP22, NME5, CENPA, BANK1, and derivatives thereof.

In another embodiment, there is provided a method for selecting a chemotherapy regimen for a subject comprising: (a) determining, from a sample derived from the subject, the expression of a first set of biomolecule(s) predictive of the efficacy of a first chemotherapy regimen; (b) applying a first model to the expression of the first set of biomolecule(s) to calculate a first predicted probability of pathological complete response (pCR) to a first chemotherapy regimen; (c) classifying the first predicted probability of pathological complete response (pCR) into a first set of probability intervals (PIs) associated with the first chemotherapy regimen; and (d) determining a first quantitative measure of chemotherapy outcome for the first chemotherapy regimen, wherein the first quantitative measure of chemotherapy outcome is predictive of the efficacy of the first chemotherapy regimen for the subject.

In another embodiment, there is provided a method for selecting a biomarker predictive of the efficacy of a chemotherapy regimen. The method comprises: (a) screening a set of genes/biomolecules using a random sampling screening (RSS) procedure to identify at least one genetic predictor; (b) generating a model incorporating at least one variable representing the genetic predictor(s), wherein the model outputs a quantitative measure of model performance; (c) determining a quantitative measure of model performance for said model; (d) at least once, repeating steps (b)-(c) to generate additional model(s) and corresponding quantitative measure(s) of model performance for said model(s); and (e) selecting a biomarker from the set of biomolecules, the selected biomarker represented by one of the variables incorporated into one of the generated models having a locally optimal quantitative measure of model performance.

In another embodiment, the present invention provides a system for selecting a chemotherapy regimen for a subject. The system comprises: (a) a data acquisition module configured to produce a data set from a sample derived from the subject, the data set comprising a diagnostic marker profile, wherein the diagnostic marker profile indicates the expression of at least one gene/biomolecule predictive of the efficacy of a chemotherapy regimen such as (i) anthracycline without paclitaxel or docetaxel, (ii) anthracycline with paclitaxel but without docetaxel, and (iii) anthracycline and docetaxel without paclitaxel; (b) a data processing module configured to process the data set by applying a learning statistical classifier system to the data set to produce a statistically derived prediction of the efficacy of a chemotherapy regimen for the subject; and (c) a display module configured to display the statistically derived prediction.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

3C shows a plot for HER2-negative, Node-negative patients.

FIG. 4 shows plots of the consistency of the predictions. In each plot, the vertical axis denotes the predicted probability of the model build on the HER2-negative, nonestratified population and the horizontal axis denotes the predicted probability of the model build on the stratified sub-population. Poor quality models (4B and 4C) tend to have poor correlations, which is expected.

FIG. 5 shows the test f-scores of individual probes and paired probes for the group of all patients. The horizontal axis shows the f-score and the vertical axis is the index. The solid line is the mean f-score of 300 randomly selected sets of probes, and dashed lines show the 95% confidence interval bounds.

FIG. 6 shows the test f-scores of individual probes and paired probes for the group of HER2-neg patients. The horizontal axis shows the f-score and the vertical axis is the index. The solid line is the mean f-score of 300 randomly selected sets of probes, and dashed lines show the 95% confidence interval bounds.

FIG. 7 shows the test f-scores of individual probes and paired probes for the group of HER2-negative, ER-negative patients. The horizontal axis shows the f-score and the vertical axis is the index. The solid line is the mean f-score of 300 randomly selected sets of probes, and dashed lines show the 95% confidence interval bounds.

FIG. 8 shows the test f-scores of individual probes and paired probes for the group of HER2-negative, ER-positive patients. The horizontal axis shows the f-score and the vertical axis is the index. The solid line is the mean f-score of 300 randomly selected sets of probes, and dashed lines show the 95% confidence interval bounds.

FIG. 9 shows the test f-scores of individual probes and paired probes for the group of HER2-negative, Lymph-Node-negative patients. The horizontal axis shows the f-score and the vertical axis is the index. The solid line is the mean f-score of 300 randomly selected sets of probes, and dashed lines show the 95% confidence interval bounds.

FIG. 10 shows the test f-scores of individual probe and paired probes for the group of HER2-negative, Lymph-Node-positive patients. The horizontal axis shows the f-score and the vertical axis is the index. The solid line is the mean f-score of 300 randomly selected sets of probes, and dashed lines show the 95% confidence interval bounds.

DETAILED DESCRIPTION OF THE INVENTION

Figure 1:
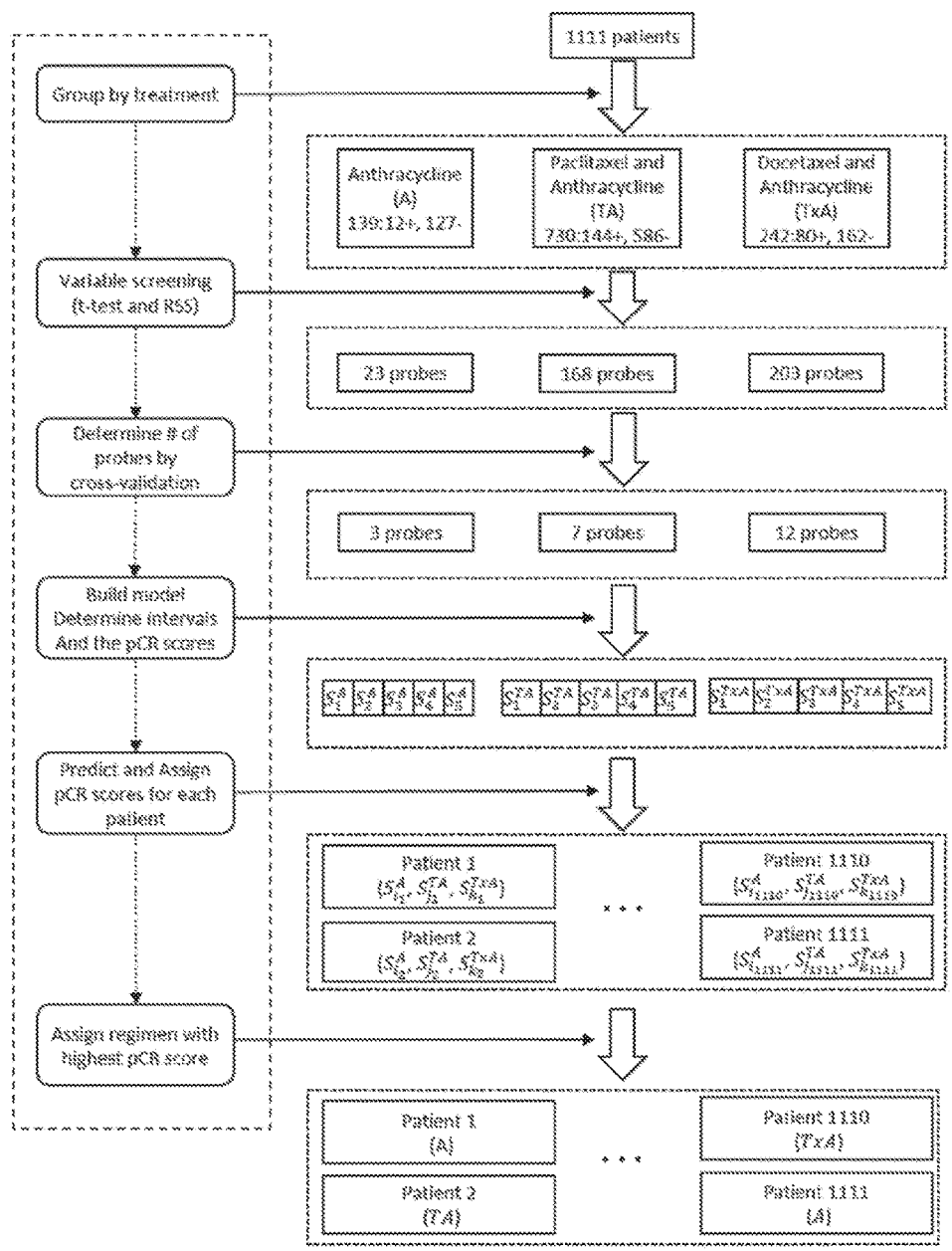
FIG. 1 is a flowchart showing the Personalized Regimen Selection (PERS) procedure.

In one embodiment, the present invention provides a kit for selecting a chemotherapy regimen for a subject. The kit comprises: one or more agents for detecting the expression of at least two biomolecules selected from the following: SLC12A7, GZMB, TAF6L, NFIB, METRN, ROPN1B, TTK, CCND1, PTTG1, H2AFZ, WDR45L, DEK, MCM2, USP1, CDT1, TMEM97, RER1, MCM6, LZTFL1, C11orf17, CCL5, XCL1, XCL2, MELK, CTSL2, TPX2, AURKA, CDKN2C, BRP44, PNP, SMC4, NR4A2, C3orf37, MTPAP, CDC25B, ABCF1, MTAP, SNAPC3, RANBP9, COIL, FAM86B1, ITGA6, S100P, RANBP1, PRSS16, SMARCA2, STK24, TSPYL5, SRI, LRP12, CENPF, TUBD1, KIAA1324, DBF4, CCNA2, DLGAP5, FHL1, SIRT3, GTSE1, PCNA, CCNE2, CHD3, CAP1, GPM6B, GUSBP3, GNAI3, LMO4, PSRC1, USP1, STK38, BAT2L1, PMP22, NME5, CENPA, BANK1, and derivatives thereof.

In one embodiment, "selecting a chemotherapy regimen" and grammatical variations thereof, may be performed when a subject has two or more chemotherapy regimens available as potential therapeutic options. In another embodiment, "selecting a chemotherapy regimen" and grammatical variations thereof, may be performed when a subject has one chemotherapy regimen available as a potential therapeutic option. Thus, in the context of the present invention, "selecting a chemotherapy regimen" may be performed, for example, when a medical professional seeks the optimal chemotherapy regimen for a subject amongst multiple chemotherapy regimens or when a medical professional decides whether to administer a chemotherapy regimen to a subject at all.

In one embodiment, "selecting a chemotherapy regimen" and grammatical variations thereof may be performed before or after the initial administration of said chemotherapy regimen to a subject. When performed before initial administration of chemotherapy, the selected chemotherapy regimen will, preferably, be administered to the subject thereafter. When performed after initial administration of chemotherapy, the selected chemotherapy regimen can be compared with the actual administered chemotherapy regimen to determine further courses of treatment.

As used herein, unless specified otherwise, a "chemotherapy regimen" may refer to any treatment in which chemotherapeutics are administered to a subject. Chemotherapeutics of the present invention include, but are not limited to, DNA damaging agents, antimetabolites, antimicrotubule agents, antibiotic agents, etc. DNA damaging agents include, but are not limited to, alkylating agents, platinum-based agents, intercalating agents, and inhibitors of DNA replication. Non-limiting examples of DNA alkylating agents include cyclophosphamide, mechlorethamine, uramustine, melphalan, chlorambucil, ifosfamide, carmustine, lomustine, streptozocin, busulfan, temozolomide, pharmaceutically acceptable salts thereof, prodrugs, and combinations thereof. Non-limiting examples of platinum-based agents include cisplatin, carboplatin, oxaliplatin, nedaplatin, satraplatin, triplatin tetranitrate, pharmaceutically acceptable salts thereof, prodrugs, and combinations thereof. Non-limiting examples of intercalating agents include anthracyclines such as doxorubicin, daunorubicin, idarubicin, mitoxantrone, valrubicin, epirubicin, pharmaceutically acceptable salts thereof, prodrugs, and combinations thereof. Non-limiting examples of inhibitors of DNA replication include irinotecan, topotecan, amsacrine, etoposide, etoposide phosphate, teniposide, pharmaceutically acceptable salts thereof, prodrugs, and combinations thereof. Antimetabolites include folate antagonists such as methotrexate and premetrexed, purine antagonists such as 6-mercaptopurine, dacarbazine, and fludarabine, and pyrimidine antagonists such as 5-fluorouracil, arabinosylcytosine, capecitabine, gemcitabine, decitabine, pharmaceutically acceptable salts thereof, prodrugs, and combinations thereof. Anti-microtubule agents include without limitation *vinca* alkaloids, paclitaxel (Taxol®), docetaxel (Taxotere®), and ixabepilone (Ixempra®). Antibiotic agents include without limitation actinomycin, bleomycin, plicamycin, mitomycin, pharmaceutically acceptable salts thereof, prodrugs, and combinations thereof.

As used herein, a "subject" is a mammal, for example, a human. In addition to humans, categories of mammals within the scope of the present invention include, for example, farm animals, domestic animals, laboratory animals, etc. Examples of farm animals include cows, pigs, horses, goats, etc. Examples of domestic animals include dogs, cats, etc. Examples of laboratory animals include primates, rats, mice, rabbits, guinea pigs, etc.

As used herein, a "subject" may also exhibit a variety of genetic characteristics relevant to the present invention. For example, a "subject" of the present invention includes, but is not limited to, a HER2-positive subject, a HER2-negative subject, a HER2-negative, ER-negative subject, a HER2-negative, ER-positive subject, a HER2-negative, lymph node-negative subject, and a HER2-negative, lymph node-positive subject.

As used herein, "components/agents for detecting the expression" of genes/biomolecules of the present invention refer to, for example, any substance, compound, composition, device, reagent, or detection agent that can be used in a laboratory or clinical setting to determine the presence and/or amount of an expression product of a biomolecule/gene in a given sample. Components/Agents for detecting expression of the present invention include, but are not limited to, a nucleic acid, a deoxyribonucleic acid, a ribonucleic acid, a set of primers, a plurality of probes, a protein, an antibody, an antigen binding fragment, a DNA array chip, a RNA array chip, an oligonucleotide array chip, and a protein array chip. It is generally known in the art that such detection agents may employ various labels, such as radioactive, fluorescent labels etc., to aid in the detection of gene expression.

As used herein, an "expression product" refers to any substance that indicates, by its presence in a sample, that a corresponding biomolecule/gene was expressed in said sample or expressed by the subject from which the sample was taken. An expression product may be, but is not limited to, an mRNA transcribed from a given biomolecule or a protein translated from said mRNA. Additionally, expression products include any fragment of an mRNA transcribed from a given biomolecule or any fragments derived from a protein translated from a given mRNA.

As used herein, "expression" refers to qualitative and quantitative measures of the amount of a given substance generated by a cell. "Expression" may include the "expression level" of a given biomolecule/gene of the present invention. Suitable forms of expression of the present invention include absolute amounts and relative amounts of a given substance generated by a cell. In the context of the present invention, "expression" includes, but is not limited to, mRNA expression, protein expression, non-coding RNA expression, and miRNA expression.

As used herein, a "biomolecule" refers to any molecule or part of a molecule present in, or secreted by, a cell. Biomolecules of the present invention include, but are not limited to, genes and gene fragments, as well as mRNA transcripts and protein products thereof. Additional biomolecules of the present invention include, but are not limited to, non-coding DNA, non-coding RNA, such as tRNAs and rRNAs, as well as miRNAs.

A "gene" is well known to those of skill in the art. Briefly, for the sake of illustration and not to be limiting in any way, a "gene" refers to any nucleic acid sequence found within an organism that can be processed biologically to produce a functional biological entity. For example, a gene can be transcribed to produce a mRNA, tRNA, or ribozyme. Furthermore, a mRNA transcribed from a gene can be translated to produce a protein, e.g. an enzyme or an antibody.

Derivatives of biomolecules of the present invention include epigenetically modified DNA, including epigenetically modified genes or gene fragments, post-transcriptionally modified RNAs (such as, but not limited to, alternatively spliced RNAs), and post-translationally modified proteins (such as, but not limited to, glycosylated proteins or proteolytically activated proteins).

In some embodiments, at least two biomolecules may be selected from a group consisting of a plurality of biomolecules. Accordingly, at least two biomolecules refers to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, or more biomolecules.

Nucleotide and polypeptide sequences corresponding to the biomolecules of the present invention are listed below in Table 1.

TABLE 1

Nucleotide and Polypeptide Sequences For Biomolecules Predictive of the Efficacy of Chemotherapy Regimens

| Biomolecule Name | Accession No. | Organism | Nucleic acid/polypeptide | Additional Details |
|---|---|---|---|---|
| SLC12A7 | NM_006598.2 | Human | Nucleic acid | |
| SLC12A7 | NP_006589.2 | Human | Polypeptide | |
| GZMB | NM_004131.4 | Human | Nucleic acid | |
| GZMB | AAH30195.1 | Human | Polypeptide | |
| TAF6L | NM_006473.3 | Human | Nucleic acid | |
| TAF6L | NP_006464.1 | Human | Polypeptide | |
| NFIB | NM_001190 737.1 | Human | Nucleic acid | Transcript variant 1 |
| NFIB | NM_001190 738.1 | Human | Nucleic acid | Transcript variant 2 |
| NFIB | NM_005596.3 | Human | Nucleic acid | Transcript variant 3 |
| NFIB | NM_001282 787.1 | Human | Nucleic acid | Transcript variant 4 |
| NFIB | NP_001177 666.1 | Human | Polypeptide | Isoform 1 |
| NFIB | NP_001177 667.1 | Human | Polypeptide | Isoform 2 |
| NFIB | NP_005587.2 | Human | Polypeptide | Isoform 3 |
| NFIB | NP_001269 716.1 | Human | Polypeptide | Isoform 4 |
| METRN | NM_024042.2 | Human | Nucleic acid | |
| METRN | NP_076947.1 | Human | Polypeptide | |
| ROPN1B | NM_001012 337.1 | Human | Nucleic acid | |
| ROPN1B | AAI41850.1 | Human | Polypeptide | |
| ROPN1B | AAH15413.1 | Human | Polypeptide | |
| TTK | NM_003318.4 | Human | Nucleic acid | Transcript variant 1 |
| TTK | NM_001166 691.1 | Human | Nucleic acid | Transcript variant 2 |
| TTK | NP_003309.2 | Human | Polypeptide | Isoform 1 |
| TTK | NP_001160 163.1 | Human | Polypeptide | Isoform 2 |
| CCND1 | NM_053056.2 | Human | Nucleic acid | |
| CCND1 | NP_444284.1 | Human | Polypeptide | |
| PTTG1 | NM_001282 382.1 | Human | Nucleic acid | Transcript variant 1 |
| PTTG1 | NM_004219.3 | Human | Nucleic acid | Transcript variant 2 |
| PTTG1 | NM_001282 383.1 | Human | Nucleic acid | Transcript variant 3 |
| PTTG1 | CAG46486.1 | Human | Polypeptide | |
| H2AFZ | NM_002106.3 | Human | Nucleic acid | |
| H2AFZ | CAG33696.1 | Human | Polypeptide | |
| WDR45L | AM182326.1 | Human | Nucleic acid | |
| WDR45L | EAW89808.1 | Human | Polypeptide | Isoform CRA_a |
| WDR45L | EAW89809.1 | Human | Polypeptide | Isoform CRA_b |
| WDR45L | EAW89810.1 | Human | Polypeptide | Isoform CRA_c |
| WDR45L | EAW89811.1 | Human | Polypeptide | Isoform CRA_d |
| WDR45L | EAW89813.1 | Human | Polypeptide | Isoform CRA_e |
| WDR45L | EAW89814.1 | Human | Polypeptide | Isoform CRA_f |
| DEK | NM_003472.3 | Human | Nucleic acid | Transcript variant 1 |
| DEK | NM_001134 709.1 | Human | Nucleic acid | Transcript variant 2 |
| DEK | NP_003463.1 | Human | Polypeptide | Isoform 1 |
| DEK | NP_001128 181.1 | Human | Polypeptide | Isoform 2 |
| MCM2 | NM_004526.3 | Human | Nucleic acid | Transcript variant 1 |
| MCM2 | NR_073375.1 | Human | Nucleic acid | Transcript variant 2 |
| MCM2 | NP_004517.2 | Human | Polypeptide | |
| USP1 | NM_003368.4 | Human | Nucleic acid | Transcript variant 1 |
| USP1 | NM_001017415.1 | Human | Nucleic acid | Transcript variant 2 |
| USP1 | NM_001017 416.1 | Human | Nucleic acid | Transcript variant 3 |
| USP1 | EAX06586.1 | Human | Polypeptide | |
| CDT1 | NM_030928.3 | Human | Nucleic acid | |
| CDT1 | AAH00137.2 | Human | Polypeptide | |
| TMEM97 | NM_014573.2 | Human | Nucleic acid | |
| TMEM97 | NP_055388.2 | Human | Polypeptide | |
| TMEM97 | EAW51069.1 | Human | Polypeptide | Isoform CRA_a |
| RER1 | NM_007033.4 | Human | Nucleic acid | |
| RER1 | EAW56113.1 | Human | Polypeptide | Isoform CRA_a |
| RER1 | EAW56114.1 | Human | Polypeptide | Isoform CRA_b |
| MCM6 | NM_005915.5 | Human | Nucleic acid | |
| MCM6 | NP_005906.2 | Human | Polypeptide | |
| LZTFL1 | NM_020347.3 | Human | Nucleic acid | Transcript variant 1 |
| LZTFL1 | NM_001276 378.1 | Human | Nucleic acid | Transcript variant 2 |
| LZTFL1 | NM_001276 379.1 | Human | Nucleic acid | Transcript variant 3 |
| LZTFL1 | NR_075080.1 | Human | Nucleic acid | Transcript variant 4 |
| LZTFL1 | NP_065080.1 | Human | Polypeptide | Isoform 1 |
| LZTFL1 | NP_001263 307.1 | Human | Polypeptide | Isoform 2 |
| LZTFL1 | NP_001263 308.1 | Human | Polypeptide | Isoform 3 |
| C11orf17 | NM_020642.3 | Human | Nucleic acid | Transcript variant 1 |
| C11orf17 | NM_001206 646.1 | Human | Nucleic acid | Transcript variant 2 |
| C11orf17 | NM_001206 647.1 | Human | Nucleic acid | Transcript variant 3 |
| C11orf17 | NM_001206 648.1 | Human | Nucleic acid | Transcript variant 4 |
| C11orf17 | NP_065693.2 | Human | Polypeptide | Isoform a |
| C11orf17 | NP_001193 575.1 | Human | Polypeptide | Isoform b |
| C11orf17 | NP_001193 576.1 | Human | Polypeptide | Isoform c |
| C11orf17 | NP_001193 577.1 | Human | Polypeptide | Isoform d |
| CCL5 | NM_002985.2 | Human | Nucleic acid | Transcript variant 1 |
| CCL5 | NM_001278 736.1 | Human | Nucleic acid | Transcript variant 2 |
| CCL5 | NP_002976.2 | Human | Nucleic acid | Isoform 1 |
| CCL5 | NP_001265 665.1 | Human | Nucleic acid | Isoform 2 |
| XCL1 | NM_002995.2 | Human | Nucleic acid | |
| XCL1 | NP_002986.1 | Human | Nucleic acid | |
| XCL2 | NM_003175.3 | Human | Nucleic acid | |
| XCL2 | NP_003166.1 | Human | Polypeptide | |
| MELK | NM_041791.3 | Human | Nucleic acid | Transcript variant 1 |
| MELK | NM_001256 685.1 | Human | Nucleic acid | Transcript variant 2 |
| MELK | NM_001256 687.1 | Human | Nucleic acid | Transcript variant 3 |
| MELK | NM_001256 688.1 | Human | Nucleic acid | Transcript variant 4 |
| MELK | NM_001256 689.1 | Human | Nucleic acid | Transcript variant 5 |
| MELK | NM_001256 690.1 | Human | Nucleic acid | Transcript variant 6 |
| MELK | NM_001256 691.1 | Human | Nucleic acid | Transcript variant 7 |
| MELK | NM_001256692.1 | Human | Nucleic acid | Transcript variant 8 |
| MELK | NM_001256 693.1 | Human | Nucleic acid | Transcript variant 9 |
| MELK | NP_055606.1 | Human | Polypeptide | Transcript variant 1 |
| MELK | NP_001243 614.1 | Human | Polypeptide | Transcript variant 2 |
| MELK | NP_001243 616.1 | Human | Polypeptide | Transcript variant 3 |

TABLE 1-continued

Nucleotide and Polypeptide Sequences For Biomolecules Predictive of the Efficacy of Chemotherapy Regimens

| Biomolecule Name | Accession No. | Organism | Nucleic acid/polypeptide | Additional Details |
|---|---|---|---|---|
| MELK | NP_001243 617.1 | Human | Polypeptide | Transcript variant 4 |
| MELK | NP_001243 618.1 | Human | Polypeptide | Transcript variant 5 |
| MELK | NP_001243 619.1 | Human | Polypeptide | Transcript variant 6 |
| MELK | NP_001243 620.1 | Human | Polypeptide | Transcript variant 7 |
| MELK | NP_001243 621.1 | Human | Polypeptide | Transcript variant 8 |
| MELK | NP_001243 622.1 | Human | Polypeptide | Transcript variant 9 |
| CTSL2 | NM_001333.3 | Human | Nucleic acid | Transcript variant 1 |
| CTSL2 | NM_001201 575.1 | Human | Nucleic acid | Transcript variant 2 |
| CTSL2 | NP_001188 504.1 | Human | Polypeptide | |
| TPX2 | NM_012112.4 | Human | Nucleic acid | |
| TPX2 | NP_036244.2 | Human | Polypeptide | |
| AURKA | NM_198433.1 | Human | Nucleic acid | Transcript variant 1 |
| AURKA | NM_003600.2 | Human | Nucleic acid | Transcript variant 2 |
| AURKA | NM_198434.1 | Human | Nucleic acid | Transcript variant 3 |
| AURKA | NM_198435.1 | Human | Nucleic acid | Transcript variant 4 |
| AURKA | NM_198436.1 | Human | Nucleic acid | Transcript variant 5 |
| AURKA | NM_198437.1 | Human | Nucleic acid | Transcript variant 6 |
| AURKA | NP_940839.1 | Human | Polypeptide | |
| CDKN2C | NM_001262.2 | Human | Nucleic acid | Transcript variant 1 |
| CDKN2C | NM_078626.2 | Human | Nucleic acid | Transcript variant 2 |
| CDKN2C | NP_523240.1 | Human | Polypeptide | |
| BRP44 | NM_001143 674.3 | Human | Nucleic acid | Transcript variant 1 |
| BRP44 | NM_015415.3 | Human | Nucleic acid | Transcript variant 2 |
| BRP44 | NP_056230.1 | Human | Polypeptide | |
| PNP | NM_000270.3 | Human | Nucleic acid | |
| PNP | NP_000261.2 | Human | Polypeptide | |
| SMC4 | NM_005496.3 | Human | Nucleic acid | Transcript variant 1 |
| SMC4 | NM_001002 800.2 | Human | Nucleic acid | Transcript variant 2 |
| SMC4 | NM_001288 753.1 | Human | Nucleic acid | Transcript variant 3 |
| SMC4 | NP_005487.3 | Human | Polypeptide | Isoform 1 |
| SMC4 | NP_001275 682.1 | Human | Polypeptide | Isoform 2 |
| NR4A2 | NM_006186.3 | Human | Nucleic acid | |
| NR4A2 | NP_006177.1 | Human | Polypeptide | |
| C3orf37 | NM_001006 109.1 | Human | Nucleic acid | Transcript variant 1 |
| C3orf37 | NM_020187.2 | Human | Nucleic acid | Transcript variant 2 |
| C3orf37 | NP_064572.2 | Human | Polypeptide | |
| MTPAP | NM_018109.3 | Human | Nucleic acid | |
| MTPAP | NP_060579.3 | Human | Polypeptide | |
| CDC25B | NM_021873.3 | Human | Nucleic acid | Transcript variant 1 |
| CDC25B | NM_004358.4 | Human | Nucleic acid | Transcript variant 2 |
| CDC25B | NM_021872.3 | Human | Nucleic acid | Transcript variant 3 |
| CDC25B | NM_001287 516.1 | Human | Nucleic acid | Transcript variant 4 |
| CDC25B | NM_001287 517.1 | Human | Nucleic acid | Transcript variant 5 |
| CDC25B | NM_001287 518.1 | Human | Nucleic acid | Transcript variant 6 |
| CDC25B | NM_001287 519.1 | Human | Nucleic acid | Transcript variant 7 |
| CDC25B | NM_001287 520.1 | Human | Nucleic acid | Transcript variant 8 |
| CDC25B | NM_001287 522.1 | Human | Nucleic acid | Transcript variant 9 |
| CDC25B | NM_001287 524.1 | Human | Nucleic acid | Transcript variant 10 |
| CDC25B | NP_068659.1 | Human | Polypeptide | Isoform 1 |
| CDC25B | NP_004349.1 | Human | Polypeptide | Isoform 2 |
| CDC25B | NP_068658.1 | Human | Polypeptide | Isoform 3 |
| CDC25B | NP_001274 445.1 | Human | Polypeptide | Isoform 4 |
| CDC25B | NP_001274 446.1 | Human | Polypeptide | Isoform 5 |
| CDC25B | NP_001274 447.1 | Human | Polypeptide | Isoform 6 |
| CDC25B | NP_001274 448.1 | Human | Polypeptide | Isoform 7 |
| CDC25B | NP_001274 451.1 | Human | Polypeptide | Isoform 8 |
| CDC25B | NP_001274 453.1 | Human | Polypeptide | Isoform 9 |
| ABCF1 | NM_001025 091.1 | Human | Nucleic acid | Transcript variant 1 |
| ABCF1 | NM_001090.2 | Human | Nucleic acid | Transcript variant 2 |
| ABCF1 | NP_001020 262.1 | Human | Polypeptide | Isoform a |
| ABCF1 | NP_001081.1 | Human | Polypeptide | Isoform b |
| MTAP | NM_002451.3 | Human | Nucleic acid | |
| MTAP | NP_002442.2 | Human | Polypeptide | |
| SNAPC3 | NM_001039 697.1 | Human | Nucleic acid | |
| SNAPC3 | NP_001034 786.1 | Human | Polypeptide | |
| RANBP9 | NM_005493.2 | Human | Nucleic acid | |
| RANBP9 | NP_005484.2 | Human | Polypeptide | |
| COIL | NM_004645.2 | Human | Nucleic acid | |
| COIL | NP_004636.1 | Human | Polypeptide | |
| FAM86B1 | NM_001083 537.1 | Human | Nucleic acid | |
| FAM86B1 | NP_001077 006.1 | Human | Polypeptide | |
| ITGA6 | NM_001079 818.1 | Human | Nucleic acid | Transcript variant 1 |
| ITGA6 | NM_000210.2 | Human | Nucleic acid | Transcript variant 2 |
| ITGA6 | NP_001073 286.1 | Human | Polypeptide | Isoform a |
| ITGA6 | NP_000201.2 | Human | Polypeptide | Isoform b |
| S100P | NM_005980.2 | Human | Nucleic acid | |
| S100P | NP_005971.1 | Human | Polypeptide | |
| RANBP1 | NM_001278 639.1 | Human | Nucleic acid | Transcript variant 1 |
| RANBP1 | NM_002882.3 | Human | Nucleic acid | Transcript variant 2 |
| RANBP1 | NM_001278 640.1 | Human | Nucleic acid | Transcript variant 3 |
| RANBP1 | NM_001278 641.1 | Human | Nucleic acid | Transcript variant 4 |
| RANBP1 | NP_001265568.1 | Human | Polypeptide | Isoform 1 |
| RANBP1 | NP_002873.1 | Human | Polypeptide | Isoform 2 |
| RANBP1 | NP_001265 569.1 | Human | Polypeptide | Isoform 3 |
| RANBP1 | NP_001265 570.1 | Human | Polypeptide | Isoform 4 |
| PRSS16 | NM_005865.3 | Human | Nucleic acid | |
| PRSS16 | NP_005856.1 | Human | Polypeptide | |
| SMARCA2 | NM_003070.4 | Human | Nucleic acid | Transcript variant 1 |
| SMARCA2 | NM_139045.3 | Human | Nucleic acid | Transcript variant 2 |
| SMARCA2 | NM_001289 396.1 | Human | Nucleic acid | Transcript variant 3 |
| SMARCA2 | NM_001289 397.1 | Human | Nucleic acid | Transcript variant 4 |
| SMARCA2 | NM_001289 398.1 | Human | Nucleic acid | Transcript variant 5 |
| SMARCA2 | NM_001289 399.1 | Human | Nucleic acid | Transcript variant 6 |
| SMARCA2 | NM_001289 400.1 | Human | Nucleic acid | Transcript variant 7 |
| SMARCA2 | NP_001276 325.1 | Human | Polypeptide | Isoform a |
| SMARCA2 | NP_620614.2 | Human | Polypeptide | Isoform b |
| SMARCA2 | NP_001276 326.1 | Human | Polypeptide | Isoform c |
| SMARCA2 | NP_001276 327.1 | Human | Polypeptide | Isoform d |

TABLE 1-continued

Nucleotide and Polypeptide Sequences For Biomolecules
Predictive of the Efficacy of Chemotherapy Regimens

| Biomolecule Name | Accession No. | Organism | Nucleic acid/ polypeptide | Additional Details |
|---|---|---|---|---|
| SMARCA2 | NP_001276 328.1 | Human | Polypeptide | Isoform e |
| SMARCA2 | NP_001276 329.1 | Human | Polypeptide | Isoform f |
| STK24 | NM_003576.4 | Human | Nucleic acid | Transcript variant 1 |
| STK24 | NM_001032 296.3 | Human | Nucleic acid | Transcript variant 2 |
| STK24 | NM_001286 649.1 | Human | Nucleic acid | Transcript variant 3 |
| STK24 | NP_003567.2 | Human | Polypeptide | Isoform a |
| STK24 | NP_001027 467.2 | Human | Polypeptide | Isoform b |
| STK24 | NP_001273 578.1 | Human | Polypeptide | Isoform c |
| TSPYL5 | NM_033512.2 | Human | Nucleic acid | |
| TSPYL5 | NP_277047.2 | Human | Polypeptide | |
| SRI | NM_003130.3 | Human | Nucleic acid | Transcript variant 1 |
| SRI | NM_198901.1 | Human | Nucleic acid | Transcript variant 2 |
| SRI | NM_001256 891.1 | Human | Nucleic acid | Transcript variant 3 |
| SRI | NM_001256 892.1 | Human | Nucleic acid | Transcript variant 4 |
| SRI | NP_003121.1 | Human | Polypeptide | Isoform A |
| SRI | NP_944490.1 | Human | Polypeptide | Isoform B |
| SRI | NP_001243 820.1 | Human | Polypeptide | Isoform C |
| SRI | NP_001243 821.1 | Human | Polypeptide | Isoform D |
| LRP12 | NM_013437.4 | Human | Nucleic acid | Transcript variant 1 |
| LRP12 | NM_001135 703.2 | Human | Nucleic acid | Transcript variant 2 |
| LRP12 | NP_038465.1 | Human | Polypeptide | Isoform a |
| LRP12 | NP_001129 175.1 | Human | Polypeptide | Isoform b |
| CENPF | NM_016343.3 | Human | Nucleic acid | |
| CENPF | NP_057427.3 | Human | Polypeptide | |
| TUBD1 | NM_016261.3 | Human | Nucleic acid | Transcript variant 1 |
| TUBD1 | NM_001193 609.1 | Human | Nucleic acid | Transcript variant 2 |
| TUBD1 | NM_001193610.1 | Human | Nucleic acid | Transcript variant 3 |
| TUBD1 | NM_001193 611.1 | Human | Nucleic acid | Transcript variant 4 |
| TUBD1 | NM_001193 612.1 | Human | Nucleic acid | Transcript variant 5 |
| TUBD1 | NM_001193 613.1 | Human | Nucleic acid | Transcript variant 6 |
| TUBD1 | NP_057345.2 | Human | Polypeptide | Isoform 1 |
| TUBD1 | NP_001180 538.1 | Human | Polypeptide | Isoform 2 |
| TUBD1 | NP_001180 539.1 | Human | Polypeptide | Isoform 3 |
| TUBD1 | NP_001180 540.1 | Human | Polypeptide | Isoform 4 |
| TUBD1 | NP_001180 541.1 | Human | Polypeptide | Isoform 5 |
| TUBD1 | NP_001180 542.1 | Human | Polypeptide | Isoform 6 |
| KIAA1324 | NM_020775.4 | Human | Nucleic acid | Transcript variant 1 |
| KIAA1324 | NM_001267 048.1 | Human | Nucleic acid | Transcript variant 2 |
| KIAA1324 | NM_001284 352.1 | Human | Nucleic acid | Transcript variant 4 |
| KIAA1324 | NM_001284 353.1 | Human | Nucleic acid | Transcript variant 5 |
| KIAA1324 | NP_065826.2 | Human | Polypeptide | Isoform 1 |
| KIAA1324 | NP_001253 977.1 | Human | Polypeptide | Isoform 2 |
| KIAA1324 | NP_001271 281.1 | Human | Polypeptide | Isoform 4 |
| KIAA1324 | NP_001271 282.1 | Human | Polypeptide | Isoform 5 |
| DBF4 | NM_006716.3 | Human | Nucleic acid | |
| DBF4 | NP_006707.1 | Human | Polypeptide | |
| CCNA2 | NM_001237.3 | Human | Nucleic acid | |
| CCNA2 | NP_001228.1 | Human | Polypeptide | |
| DLGAP5 | NM_014750.4 | Human | Nucleic acid | Transcript variant 1 |
| DLGAP5 | NM_001146 015.1 | Human | Nucleic acid | Transcript variant 2 |
| DLGAP5 | NP_055565.3 | Human | Polypeptide | Isoform a |
| DLGAP5 | NP_001139 487.1 | Human | Polypeptide | Isoform b |
| FHL1 | NM_001159 702.2 | Human | Nucleic acid | Transcript variant 1 |
| FHL1 | NM_001449.4 | Human | Nucleic acid | Transcript variant 2 |
| FHL1 | NM_001159 700.1 | Human | Nucleic acid | Transcript variant 3 |
| FHL1 | NM_001159 704.1 | Human | Nucleic acid | Transcript variant 4 |
| FHL1 | NM_001159 701.1 | Human | Nucleic acid | Transcript variant 5 |
| FHL1 | NM_001159 703.1 | Human | Nucleic acid | Transcript variant 6 |
| FHL1 | NM_001159 699.1 | Human | Nucleic acid | Transcript variant 7 |
| FHL1 | NM_001167 819.1 | Human | Nucleic acid | Transcript variant 9 |
| FHL1 | NP_001153 174.1 | Human | Polypeptide | Isoform 1 |
| FHL1 | NP_001440.2 | Human | Polypeptide | Isoform 2 |
| FHL1 | NP_001153 173.1 | Human | Polypeptide | Isoform 3 |
| FHL1 | NP_001153 175.1 | Human | Polypeptide | Isoform 4 |
| FHL1 | NP_001153 171.1 | Human | Polypeptide | Isoform 5 |
| SIRT3 | NM_012239.5 | Human | Nucleic acid | Transcript variant 1 |
| SIRT3 | NM_001017 524.2 | Human | Nucleic acid | Tanscript variant 2 |
| SIRT3 | NP_036371.1 | Human | Polypeptide | Isoform a |
| SIRT3 | NP_001017 524.1 | Human | Polypeptide | Isoform b |
| GTSE1 | NM_016426.6 | Human | Nucleic acid | |
| GTSE1 | NP_057510.4 | Human | Polypeptide | |
| PCNA | NM_002592.2 | Human | Nucleic acid | Transcript variant 1 |
| PCNA | NM_182649.1 | Human | Nucleic acid | Transcript variant 2 |
| PCNA | NP_872590.1 | Human | Polypeptide | |
| CCNE2 | NM_057749.2 | Human | Nucleic acid | |
| CCNE2 | NP_477097.1 | Human | Polypeptide | |
| CHD3 | NM_001005 273.2 | Human | Nucleic acid | Transcript variant 1 |
| CHD3 | NM_005852.3 | Human | Nucleic acid | Transcript variant 2 |
| CHD3 | NM_001005 271.2 | Human | Nucleic acid | Transcript variant 3 |
| CHD3 | NP_001005 273.1 | Human | Polypeptide | Isoform 1 |
| CHD3 | NP_005843.2 | Human | Polypeptide | Isoform 2 |
| CHD3 | NP_001005 271.2 | Human | Polypeptide | Isoform 3 |
| CAP1 | NM_006367.3 | Human | Nucleic acid | Transcript variant 1 |
| CAP1 | NM_001105 530.1 | Human | Nucleic acid | Transcript variant 2 |
| CAP1 | NP_006358.1 | Human | Polypeptide | |
| GPM6B | NM_001001 995.1 | Human | Nucleic acid | Transcript variant 1 |
| GPM6B | NM_001001 996.1 | Human | Nucleic acid | Transcript variant 2 |
| GPM6B | NM_005278.3 | Human | Nucleic acid | Transcript variant 3 |
| GPM6B | NM_001001 994.1 | Human | Nucleic acid | Transcript variant 4 |
| GPM6B | NP_001001 995.1 | Human | Polypeptide | Isoform 1 |
| GPM6B | NP_001001 996.1 | Human | Polypeptide | Isoform 2 |
| GPM6B | NP_005269.1 | Human | Polypeptide | Isoform 3 |
| GPM6B | NP_001001 994.1 | Human | Polypeptide | Isoform 4 |
| GUSBP3 | NR_027386.1 | Human | Nucleic acid | |
| GNAI3 | NM_006496.3 | Human | Nucleic acid | |
| GNAI3 | NP_006487.1 | Human | Polypeptide | |
| LMO4 | NM_006769.3 | Human | Nucleic acid | |
| LMO4 | NP_006760.1 | Human | Polypeptide | |
| PSRC1 | NM_032636.7 | Human | Nucleic acid | Transcript variant 1 |
| PSRC1 | NM_001005 290.3 | Human | Nucleic acid | Transcript variant 2 |
| PSRC1 | NM_001032 291.2 | Human | Nucleic acid | Transcript variant 3 |

TABLE 1-continued

Nucleotide and Polypeptide Sequences For Biomolecules
Predictive of the Efficacy of Chemotherapy Regimens

| Biomolecule Name | Accession No. | Organism | Nucleic acid/ polypeptide | Additional Details |
|---|---|---|---|---|
| PSRC1 | NP_001027 462.1 | Human | Polypeptide | Isoform a |
| PSRC1 | NP_001005 290.1 | Human | Polypeptide | Isoform b |
| USP1 | NM_003368.4 | Human | Nucleic acid | Transcript variant 1 |
| USP1 | NM_001017 415.1 | Human | Nucleic acid | Transcript variant 2 |
| USP1 | NM_001017 416.1 | Human | Nucleic acid | Transcript variant 3 |
| USP1 | NP_001017 416.1 | Human | Polypeptide | |
| STK38 | NM_007271.2 | Human | Nucleic acid | |
| STK38 | NP_009202.1 | Human | Polypeptide | |
| BAT2L1 | NM_013318.3 | Human | Nucleic acid | |
| BAT2L1 | NP_037450.2 | Human | Polypeptide | |
| PMP22 | NM_000304.3 | Human | Nucleic acid | Transcript variant 1 |
| PMP22 | NM_153321.2 | Human | Nucleic acid | Transcript variant 2 |
| PMP22 | NM_153322.2 | Human | Nucleic acid | Transcript variant 3 |
| PMP22 | NM_001281 455.1 | Human | Nucleic acid | Transcript variant 4 |
| PMP22 | NM_001281 456.1 | Human | Nucleic acid | Transcript variant 5 |
| PMP22 | NP_001268 384.1 | Human | Polypeptide | |
| NME5 | NM_003551.2 | Human | Nucleic acid | |
| NME5 | NP_003542.1 | Human | Polypeptide | |
| CENPA | NM_001809.3 | Human | Nucleic acid | Transcript variant 1 |
| CENPA | NM_001042 426.1 | Human | Nucleic acid | Transcript variant 2 |
| CENPA | NP_001800.1 | Human | Polypeptide | Isoform a |
| CENPA | NP_001035 891.1 | Human | Polypeptide | Isoform b |
| BANK1 | NM_017935.4 | Human | Nucleic acid | Transcript variant 1 |
| BANK1 | NM_001083 907.2 | Human | Nucleic acid | Transcript variant 2 |
| BANK1 | NP_060405.4 | Human | Polypeptide | Isoform 1 |
| BANK1 | NP_001077 376.2 | Human | Polypeptide | Isoform 2 |
| BANK1 | NP_001120 979.2 | Human | Polypeptide | Isoform 3 |

In one embodiment, the kit of the present invention comprises one or more agents for detecting the expression of at least three genes/biomolecules listed herein.

As used herein, at least three genes/biomolecules refers to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, or more biomolecules.

In another embodiment, the kit comprises one or more agents for detecting the expression of at least two genes/biomolecules selected independently from the genes/biomolecules in Group 1, Group 2, and Group 3:
Group 1: SLC12A7, GZMB, TAF6L, and derivatives thereof;
Group 2: NFIB, METRN, ROPN1B, TTK, CCND1, and derivatives thereof;
Group 3: PTTG1, H2AFZ, WDR45L, DEK, MCM2, USP1, CDT1, TMEM97, RER1, MCM6, LZTFL1, and derivatives thereof.

As used herein, "selected independently" means that selection of a biomolecule need not impact selection of another biomolecule.

In another embodiment, the kit comprises one or more agents for detecting the expression of at least two biomolecules selected independently from the biomolecules in Group 4, Group 5, and Group 6:
Group 4: SLC12A7, GZMB, C11orf17, TAF6L, CCL5, XCL1, XCL2, and derivatives thereof;
Group 5: NFIB, ROPN1B, TTK, MELK, CTSL2, METRN, and derivatives thereof;
Group 6: TPX2, PTTG1, MCM2, MCM6, AURKA, CDKN2C, BRP44, H2AFZ, PNP, SMC4, DEK, TMEM97, NR4A2, C3orf37, LZTFL1, MTPAP, CDC25B, ABCF1, and derivatives thereof.

In another embodiment, the kit comprises one or more agents for detecting the expression of at least two biomolecules selected independently from the biomolecules in Group 7 and Group 8:
Group 7: NFIB, MTAP, SNAPC3, RANBP9, COIL, FAM86B1, ITGA6, S100P, RANBP1, PRSS16, SMARCA2, STK24, and derivatives thereof;
Group 8: TSPYL5, SRI, and derivatives thereof.

In another embodiment, the kit comprises one or more agents for detecting the expression of at least two biomolecules selected independently from the biomolecules in Group 9 and Group 10:
Group 9: LRP12, CENPF, TUBD1, KIAA1324, TTK, and derivatives thereof;
Group 10: DBF4, DEK, CDC25B, CCNA2, DLGAP5, MCM2, CDKN2C, FHL1, SIRT3, GTSE1, PCNA, CCNE2, and derivatives thereof.

In another embodiment, the kit comprises one or more agents for detecting the expression of at least two biomolecules selected independently from the biomolecules in Group 11 and Group 12:
Group 11: CHD3, CAP1, GPM6B, GUSBP3, and derivatives thereof;
Group 12: CDKN2C, GNAI3, LMO4, PSRC1, USP1, STK38, and derivatives thereof.

In another embodiment, the kit comprises one or more agents for detecting the expression of at least two biomolecules selected independently from the biomolecules in Group 13 and Group 14:
Group 13: NFIB, ROPN1B, and derivatives thereof;
Group 14: TPX2, BAT2L1, PMP22, PTTG1, NME5, CENPA, BANK1, and derivatives thereof.

In one embodiment, the at least two biomolecules selected comprise at least two biomolecules selected from different groups of biomolecules. For example, one biomolecule may be selected from Group 1 and another biomolecule may be selected from Group 2.

In another embodiment, the at least two biomolecules selected comprise at least two biomolecules selected from the same group of biomolecules. For example, one biomolecule may be selected from Group 1 and another biomolecule may also be selected from Group 1.

In another embodiment, the kit comprises one or more agents for detecting each of the biomolecules in one of said groups of biomolecules. For example, agents for detecting biomolecules may detect all biomolecules from Group 1.

In another embodiment, the kit comprises one or more agents for detecting each of the biomolecules in at least two of said groups of biomolecules. For example, agents for detecting biomolecules may detect all biomolecules from Group 1 and Group 2. Moreover, agents for detecting biomolecules may detect all biomolecules from Group 1, Group 2, and Group 3.

In another embodiment, the kit comprises one or more agents for detecting each of the biomolecules in each of said groups of biomolecules. For example, agents for detecting biomolecules may detect all biomolecules in Group 1, Group 2, and Group 3. In another example, agents for detecting biomolecules may detect all biomolecules in Group 13 and Group 14.

In one embodiment, the above one or more agents are selected from the following: a DNA array chip, a RNA array chip, an oligonucleotide array chip, a protein array chip, an antibody, an antigen binding fragment, a plurality of probes, and a set of primers.

Array chips of the present invention may comprise, for example, nucleic acids or proteins bound or otherwise associated with specific regions on said chips. Specific regions of an array chip typically correspond to a given species, such as a gene, mRNA, cDNA, nucleic acid probe, or protein probe. Arrays of the present invention may be of any size, for example, a 2×2 array or a 100×100 array.

Antigen binding fragments of the present invention include, but are not limited to, antibody fragments such as scFvs or Fabs, and receptors, such as cell surface receptors, and receptor fragments thereof.

Primers of the present invention include, but are not limited to, primers used in polymerase chain reaction (PCR) applications and primers used in reverse transcriptase (RT)-PCR applications.

In one embodiment, the gene expression is selected from the following: mRNA expression, protein expression, non-coding RNA expression, and miRNA expression.

The kits of the present invention may further include suitable storage containers, e.g., ampules, vials, tubes, etc., for each detection agent and other reagents, e.g., buffers, balanced salt solutions, etc., for use in utilizing the detection agent(s) on samples. The detection agent(s) and other reagents may be present in the kits in any convenient form, such as, e.g., in a solution or in a powder form. The kits may further include a packaging container, optionally having one or more partitions for housing the detection agents and other optional reagents.

In another embodiment, the present invention provides a method for predicting the efficacy of a chemotherapy regimen for a subject. The method comprises: (a) determining, from a sample derived from the subject, the expression of at least one gene/biomolecule predictive of the efficacy of a chemotherapy regimen; (b) applying a model to the expression of said biomolecule(s) to calculate a predicted probability of pathological complete response (pCR) to a chemotherapy regimen; (c) classifying the predicted probability of pathological complete response (pCR) into a set of probability intervals (PIs) associated with the chemotherapy regimen; (d) determining a quantitative measure of chemotherapy outcome for the chemotherapy regimen, wherein the quantitative measure of chemotherapy outcome is predictive of the efficacy of the chemotherapy regimen for the subject.

In one embodiment, "predicting the efficacy of a chemotherapy regimen" is performed before administration of chemotherapy and may optimize a subject's therapeutic outcome. Such predictions may assist a medical professional in determining whether to administer a given chemotherapy regimen to a subject. In another embodiment, "predicting the efficacy of a chemotherapy regimen" is performed after administration of chemotherapy to assess whether a particular course of treatment was appropriate initially and/or if a change in treatment should be made because of, for example, changing genetic factors in a subject's tumor.

As used herein and henceforth, "subjects" and "chemotherapy regimens" are as defined above.

In one embodiment, step (a), comprising determining from a sample derived from the subject, the expression of at least one biomolecule predictive of the efficacy of a chemotherapy regimen, may involve the use any number of assays, including hybridization assays, amplification-based assays, immunoassays, or immunohistochemical assays.

Hybridization assays include, but are not limited to, dot blotting, RNase protection, Northern blotting, microarrays, fluorescence in situ hybridization (FISH), and combinations thereof. Amplification-based assays include, but are not limited to, polymerase chain reaction (PCR), reverse transcriptase-PCR (RT-PCR), and combinations thereof. Immunoassays include, but are not limited to, immunocytochemistry, immunohistochemistry, enzyme-linked immunosorbent assay (ELISA), Memory Lymphocyte Immunostimulation Assay (MELISA), cloned enzyme donor immunoassay (CEDIA), and combinations thereof. Immunohistochemical assays include, but are not limited to, immunofluorescence assays, such as direct fluorescent antibody assays, indirect fluorescent antibody (IFA) assays, anticomplement immunofluorescence assays, avidin-biotin immunofluorescence assays, and fluorescence-activated cell sorting (FACS). These assays are well known to those of skill in the art.

As used herein, a "sample" is any biological specimen obtained from a subject. Samples of the present invention include, but are not limited to, whole blood, plasma, serum, saliva, urine, stool, sputum, tears, any other bodily fluid, tissue samples such as biopsies, and cellular extracts thereof.

In one embodiment, determining the expression of at least one biomolecule from various groups disclosed above may involve determining the expression of one biomolecule or more than one biomolecule from a given group. At least one biomolecule may refer to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, or more biomolecules. Furthermore, it is envisioned that determining the expression of additional biomolecules not listed in the groups disclosed herein, that may or may not have additional predictive value to the biomolecules disclosed herein, is within the scope of the present invention.

In one embodiment, "applying a model" to an expression disclosed above may be performed on a computer or system disclosed herein. Statistical models of the present invention, alternatively referred to as "learning statistical classifier systems" herein, may include, but are not limited to, random forest models, classification and regression tree models, boosting, Bayesian networks, Markov random field, linear and generalized linear models, boosted tree models, neural networks, support vector machines, general chi-squared automatic interaction detector models, interactive tree models, multiadaptive regression spline, machine learning classifiers, and combinations thereof. These statistical models are well known to those of skill in the art.

Models of the present invention may be evaluated in terms of, for example, a "quantitative measure of model performance," as used herein, such as accuracy, precision, recall, and/or f1-score. In one embodiment, models of the present invention are evaluated in terms of f1-score. F1-score is defined herein as 2×[(precision×recall)/(precision+recall)], wherein precision and recall are statistical terms well known to those of skill in the art. In one embodiment of the present invention, multiple statistical models are developed based on several variables, including clinical variables, such as tumor size, age, ER status, PR status, HER2 status, lymph node status, t_stage, and n_stage and genetic variables, such as the expression of any of the biomolecules disclosed herein. In one embodiment, statistical models of the present invention are developed by assessing the f1-scores of the various models as new variables are incorporated into the models. For example, a model incorporating only clinical variables will return a certain f1-score. A new model incorporating clinical variables and a single genetic variable will return another f1-score that can be compared to the first f1-score. Higher f1-scores generally are indicative of models with more predictive power.

In one embodiment, statistical models are those that yield a local maximum f1-score. In another embodiment, useful statistical models are those that yield a first local maximum f1-score. Herein, a "local maximum" refers to a score that resulted from a first statistical model wherein other statistical models incorporating variables additional to those incorporated in the first statistical model and other statistical models incorporating a subset of variables incorporated in the first statistical model yield lower f1-scores than the first statistical model. A local maximum f1-score can be the f1-score gathered from a first statistical model wherein statistical models having 1, 2, 3, 4, 5, 6, 7, 8, 9, 10, or more variables additional to those incorporated in the first statistical model and statistical models having 1, 2, 3, 4, 5, 6, 7, 8, 9, 10, or fewer variables from the set of variables included in the first statistical model yield lower f1-scores than the first statistical model. In one embodiment, a local maximum f1-score of the present invention is yielded from a first statistical model, wherein statistical models having 3 variables additional to those of the first statistical model or statistical models having a subset of variables that is 3 variables less than the set of variables from the first statistical model yield lower f1-scores than the first statistical model. As variables are added to a given model, the first local maximum f1-score will be achieved. Additional variables may provide a model producing a second local maximum f1-score, however, in one embodiment of the present invention models producing a first local maximum f1-score are utilized.

In another embodiment, statistical models of the present invention are associated with chemotherapy regimens of the present invention. For example, the regimen "anthracycline without paclitaxel or docetaxel" may be associated with a first statistical model and the regimen "anthracycline and paclitaxel without docetaxel" may be associated with a second statistical model.

In one embodiment, statistical models of the present invention produce a predicted probability of pathological complete response (pCR) to a chemotherapy regimen. pCR has previously been defined (Kaufmann, et al., 2006, Kuerer, et al., 1999, von Minckwitz, et al., 2012). In the context of the present invention, a given statistical model should output a single predicted probability of pCR for a given patient administered the chemotherapy regimen associated with said statistical model. Likewise, a different statistical model, associated with a different chemotherapy regimen, may output a different predicted probability of pCR for the same patient. Thus, a patient may be assigned multiple predicted probabilities of pCR derived from multiple statistical models associated with multiple chemotherapy regimens.

In one embodiment, the predicted probability of pathological complete response (pCR) is classified into a set of probability intervals associated with a chemotherapy regimen. In the context of the present invention, a statistical model may be applied to expression data derived from groups of patients to yield probability intervals associated with said statistical model. For example, given a data set of expression data gathered from patients exposed to a first chemotherapy regimen, a statistical model can be applied to the expression data from each patient to yield a predicted probability of pCR for each patient. These predicted probabilities of pCR can be grouped into any number of probability intervals wherein the number of predicted probabilities of pCR in each probability interval is roughly equivalent (i.e. within 1, 2, 3, 4, 5, 6, 7, 8, 9, or 10 or more predicted probabilities of pCR of each other). Probability intervals may be defined as a range of values between, and including, a lower limit and upper limit. For example, the interval [0,1] would include all values between 0 and 1, including 0 and 1. In one embodiment, the predicted probabilities of pCR are grouped into 5 probability intervals.

Given the probability intervals determined for a group of patients, the method of the present embodiment involves classifying a subject's predicted probability of pCR into one of the aforementioned probability intervals.

In one embodiment, a subject with multiple predicted probabilities of pCR associated with multiple chemotherapy regimens may have their predicted probabilities of pCR classified into multiple probability intervals, each probability interval being chosen from a set of probability intervals associated with a particular chemotherapy regimen.

In one embodiment, a quantitative measure of chemotherapy outcome is determined for a given chemotherapy regimen. In one embodiment, the quantitative measure of chemotherapy outcome is a pCR score. A pCR score is distinct from a predicted probability of pCR. A pCR score is defined as the estimated probability of having pCR for a particular regimen for a patient whose predicted probability of pCR was classified into a particular probability interval. In the context of the present embodiment, pCR scores may be associated with probability intervals before or after a subject's predicted probability of pCR is classified into a probability interval. As used herein, the pCR score is calculated as the ratio of the number of patients sorted into a given probability interval who were observed to have a pCR to the total number of patients sorted into the probability interval. This ratio is also referred to herein as the positive predicted value (PPV). Thus, when a subject's predicted probability of pCR for a given chemotherapy regimen is classified into a probability interval, the pCR score associated with said probability interval is determined as the pCR score for a given chemotherapy regimen for said subject.

In one embodiment, a subject with multiple predicted probabilities of pCR associated with multiple chemotherapy regimens may have their predicted probabilities of pCR classified into multiple probability intervals, each probability interval being chosen from a set of probability intervals associated with a particular chemotherapy regimen. Likewise, each probability interval is associated with a pCR score, and the subject is thus associated with the pCR scores corresponding to the intervals for which the subject's predicted probabilities of pCR are classified into.

In one embodiment, the efficacy of a chemotherapy regimen is predicted for a subject. Based on a quantitative measure of chemotherapy outcome, such as pCR score, a subject or medical professional can predict the likelihood of the subject achieving pCR as a result of administration of the chemotherapy regimen associated with said pCR score. In the event that a subject has multiple pCR scores associated with multiple chemotherapy regimens, the chemotherapy regimen associated with the highest pCR score is predicted to be the most effective chemotherapy regimen for said subject out of those chemotherapy regimens compared.

In another embodiment, the present invention provides a method for predicting the efficacy of a chemotherapy regimen for a subject. The method comprises: (a) determining, from a sample derived from the subject, the expression of at least two genes/biomolecules selected from the following: SLC12A7, GZMB, TAF6L, NFIB, METRN, ROPN1B, TTK, CCND1, PTTG1, H2AFZ, WDR45L, DEK, MCM2, USP1, CDT1, TMEM97, RER1, MCM6, LZTFL1, C11orf17, CCL5, XCL1, XCL2, MELK, CTSL2, TPX2, AURKA, CDKN2C, BRP44, PNP, SMC4, NR4A2, C3orf37, MTPAP, CDC25B, ABCF1, MTAP, SNAPC3, RANBP9, COIL, FAM86B1, ITGA6, S100P, RANBP1, PRSS16, SMARCA2, STK24, TSPYL5, SRI, LRP12, CENPF, TUBD1, KIAA1324, DBF4, CCNA2, DLGAP5, FHL1, SIRT3, GTSE1, PCNA, CCNE2, CHD3, CAP1, GPM6B, GUSBP3, GNAI3, LMO4, PSRC1, USP1, STK38, BAT2L1, PMP22, NME5, CENPA, BANK1, and derivatives thereof.

In another embodiment, there is provided a method for predicting the efficacy of a chemotherapy regimen for a subject, wherein the chemotherapy regimen comprises anthracycline without paclitaxel or docetaxel. The method comprises: (a) determining, from a sample derived from the subject, the expression of at least one gene/biomolecule selected from the group consisting of SLC12A7, GZMB, TAF6L, and derivatives thereof; (b) applying a model to the expression of said gene/biomolecule(s) to calculate a predicted probability of pathological complete response (pCR) to a chemotherapy regimen; (c) classifying the predicted probability of pathological complete response (pCR) into a set of probability intervals (PIs) associated with the chemotherapy regimen; (d) determining a quantitative measure of chemotherapy outcome for the chemotherapy regimen, wherein the quantitative measure of chemotherapy outcome is predictive of the efficacy of the chemotherapy regimen for the subject.

In another embodiment of the present invention, there is a method for predicting the efficacy of a chemotherapy regimen for a subject, wherein the chemotherapy regimen comprises anthracycline and paclitaxel without docetaxel. The method comprises:
a. determining, from a sample derived from the subject, the expression of at least one biomolecule selected from the group consisting of NFIB, METRN, ROPN1B, TTK, CCND1, and derivatives thereof;
b. applying a model to the expression said biomolecule(s) to calculate a predicted probability of pathological complete response to a chemotherapy regimen;
c. classifying the predicted probability of pathological complete response (pCR) into a set of probability intervals (PIs) associated with the chemotherapy regimen;
d. determining a quantitative measure of chemotherapy outcome for the chemotherapy regimen, wherein the quantitative measure of chemotherapy outcome is predictive of the efficacy of the chemotherapy regimen for the subject.

An additional embodiment of the present invention is a method for predicting the efficacy of a chemotherapy regimen for a subject, wherein the chemotherapy regimen comprises anthracycline with docetaxel and without paclitaxel. The method comprises:
a. determining, for a sample derived from the subject, the expression of at least one biomolecule selected from the group consisting of PTTG1, H2AFZ, WDR45L, DEK, MCM2, USP1, CDT1, TMEM97, RER1, MCM6, LZTFL1, and derivatives thereof;
b. applying a model to the expression of said biomolecule(s) to calculate a predicted probability of pathological complete response (pCR) to a chemotherapy regimen; classifying the predicted probability of pathological complete response (pCR) into a set of probability intervals (PIs) associated with the chemotherapy regimen;
c. determining a quantitative measure of chemotherapy outcome for the chemotherapy regimen, wherein the quantitative measure of chemotherapy outcome is predictive of the efficacy of the chemotherapy regimen for the subject.

As used herein, the regimen "anthracycline without paclitaxel or docetaxel" includes one or more anthracyclines and, optionally, any other compound or composition administered for therapeutic use except paclitaxel and analogs thereof and docetaxel and analogs thereof. Likewise, the regimen "anthracycline with paclitaxel and without docetaxel" includes one or more anthracyclines, paclitaxel and/or analogs thereof, and, optionally, any other compound or composition administered for therapeutic use except docetaxel and analogs thereof. Similarly, the regimen "anthracycline with docetaxel and without paclitaxel" includes one or more anthracyclines, docetaxel and/or analogs thereof, and, optionally, any other compound or composition administered for therapeutic use except paclitaxel and analogs thereof.

Another embodiment of the present invention is a method for predicting the efficacy of a chemotherapy regimen for a HER2-negative subject, wherein the chemotherapy regimen comprises anthracycline without paclitaxel or docetaxel. The method comprises:
a. determining, for a sample derived from the subject, the expression of at least one biomolecule selected from the group consisting of SLC12A7, GZMB, C11orf17, TAF6L, CCL5, XCL1, XCL2, and derivatives thereof;
b. applying a model to the expression of said biomolecule(s) to calculate a predicted probability of pathological complete response (pCR) to a chemotherapy regimen; classifying the predicted probability of pathological complete response (pCR) into a set of probability intervals (PIs) associated with the chemotherapy regimen;
c. determining a quantitative measure of chemotherapy outcome for the chemotherapy regimen, wherein the quantitative measure of chemotherapy outcome is predictive of the efficacy of the chemotherapy regimen for the subject.

A further embodiment of the present invention is a method for predicting the efficacy of a chemotherapy regimen for a HER2-negative subject, wherein the chemotherapy regimen comprises anthracycline with paclitaxel and without docetaxel. The method comprises:
a. determining, for a sample derived from the subject, the expression of at least one biomolecule selected from the group consisting of NFIB, ROPN1B, TTK, MELK, CTSL2, METRN, and derivatives thereof;
b. applying a model to the expression of said biomolecule(s) to calculate a predicted probability of pathological complete response (pCR) to a chemotherapy regimen;
c. classifying the predicted probability of pathological complete response (pCR) into a set of probability intervals (PIs) associated with the chemotherapy regimen;
d. determining a quantitative measure of chemotherapy outcome for the chemotherapy regimen, wherein the quantitative measure of chemotherapy outcome is predictive of the efficacy of the chemotherapy regimen for the subject.

An additional embodiment of the present invention is a method for predicting the efficacy of a chemotherapy regimen for a HER2-negative subject, wherein the chemotherapy regimen comprises anthracycline with docetaxel and without paclitaxel. The method comprises:

a. determining, for a sample derived from the subject, the expression of at least one biomolecule selected from the group consisting of TPX2, PTTG1, MCM2, MCM6, AURKA, CDKN2C, BRP44, H2AFZ, PNP, SMC4, DEK, TMEM97, NR4A2, C3orf37, LZTFL1, MTPAP, CDC25B, ABCF1, and derivatives thereof;
b. applying a model to the expression of said biomolecule(s) to calculate a predicted probability of pathological complete response (pCR) to a chemotherapy regimen;
c. classifying the predicted probability of pathological complete response (pCR) into a set of probability intervals (PIs) associated with the chemotherapy regimen;
d. determining a quantitative measure of chemotherapy outcome for the chemotherapy regimen, wherein the quantitative measure of chemotherapy outcome is predictive of the efficacy of the chemotherapy regimen for the subject.

The human epidermal growth factor receptor 2 (HER2) gene expresses a membrane tyrosine kinase which, when overexpressed in certain tumor tissues, grants certain biological functionalities to those tissues, including sensitivity to certain therapeutics. Levels of HER2 in cancer cells may be determined by, for example, immunohistochemistry (IHC) and fluorescence in situ hybridization (FISH). When FISH data is used, cancers are classified according to a score corresponding to HER2 levels detected. Cancers with a score of 0 are considered HER2-negative and exhibit no staining of HER2. Cancers scored as 1+ show weak or incomplete membrane staining in any proportion of tumor cells and are considered HER2-negative. 2+ cancers are classified as HER2-equivocal and show complete membrane staining, nonuniform or weak in intensity, in at least 10% of cells or intense complete membrane staining in 30% or less of tumor cells. HER-positive cancers are given scores of 3+ and are characterized by uniform intense membrane staining in 30% of invasive tumor cells. In the context of the present invention, criteria for determining if a subject is HER2-negative/positive, ER-negative/positive, or lymph node-negative/positive are well known to those in the art. Furthermore, certain criteria for determining a subject's HER2/ER/lymph node status may change over time as analytical techniques improve. The criteria listed herein is included for purposes of illustration only and is not meant to be limiting in any way.

Another embodiment of the present invention is a method for predicting the efficacy of a chemotherapy regimen for a HER2-negative, ER-negative subject, wherein the chemotherapy regimen comprises anthracycline with paclitaxel and without docetaxel. The method comprises:
a. determining, for a sample derived from the subject, the expression of at least one biomolecule selected from the group consisting of NFIB, MTAP, SNAPC3, RANBP9, COIL, FAM86B1, ITGA6, S100P, RANBP1, PRSS16, SMARCA2, STK24, and derivatives thereof;
b. applying a model to the expression of said biomolecule(s) to calculate a predicted probability of pathological complete response (pCR) to a chemotherapy regimen;
c. classifying the predicted probability of pathological complete response (pCR) into a set of probability intervals (PIs) associated with the chemotherapy regimen;
d. determining a quantitative measure of chemotherapy outcome for the chemotherapy regimen, wherein the quantitative measure of chemotherapy outcome is predictive of the efficacy of the chemotherapy regimen for the subject.

A further embodiment of the present invention is a method for predicting the efficacy of a chemotherapy regimen for a HER2-negative, ER-negative subject, wherein the chemotherapy regimen comprises anthracycline with docetaxel and without paclitaxel. The method comprises:
a. determining, for a sample derived from the subject, the expression of at least one biomolecule selected from the group consisting of TSPYL5, SRI, and derivatives thereof;
b. applying a model to the expression of said biomolecule(s) to calculate a predicted probability of pathological complete response (pCR) to a chemotherapy regimen;
c. classifying the predicted probability of pathological complete response (pCR) into a set of probability intervals (PIs) associated with the chemotherapy regimen;
d. determining a quantitative measure of chemotherapy outcome for the chemotherapy regimen, wherein the quantitative measure of chemotherapy outcome is predictive of the efficacy of the chemotherapy regimen for the subject.

An additional embodiment of the present invention is a method for predicting the efficacy of a chemotherapy regimen for a HER2-negative, ER-positive subject, wherein the chemotherapy regimen comprises anthracycline with paclitaxel and without docetaxel. The method comprises:
a. determining, for a sample derived from the subject, the expression of at least one biomolecule selected from the group consisting of LRP12, CENPF, TUBD1, KIAA1324, TTK, and derivatives thereof;
b. applying a model to the expression of said biomolecule(s) to calculate a predicted probability of pathological complete response (pCR) to a chemotherapy regimen;
c. classifying the predicted probability of pathological complete response (pCR) into a set of probability intervals (PIs) associated with the chemotherapy regimen;
d. determining a quantitative measure of chemotherapy outcome for the chemotherapy regimen, wherein the quantitative measure of chemotherapy outcome is predictive of the efficacy of the chemotherapy regimen for the subject.

Another embodiment of the present invention is a method for predicting the efficacy of a chemotherapy regimen for a HER2-negative, ER-positive subject, wherein the chemotherapy regimen comprises anthracycline with docetaxel and without paclitaxel. The method comprises:
a. determining, for a sample derived from the subject, the expression of at least one biomolecule selected from the group consisting of DBF4, DEK, CDC25B, CCNA2, DLGAP5, MCM2, CDKN2C, FHL1, SIRT3, GTSE1, PCNA, CCNE2, and derivatives thereof;
b. applying a model to the expression of said biomolecule(s) to calculate a predicted probability of pathological complete response (pCR) to a chemotherapy regimen;
c. classifying the predicted probability of pathological complete response (pCR) into a set of probability intervals (PIs) associated with the chemotherapy regimen;
d. determining a quantitative measure of chemotherapy outcome for the chemotherapy regimen, wherein the quantitative measure of chemotherapy outcome is predictive of the efficacy of the chemotherapy regimen for the subject.

A further embodiment of the present invention is a method for predicting the efficacy of a chemotherapy regimen for a HER2-negative, lymph node-negative subject, wherein the chemotherapy regimen comprises anthracycline with paclitaxel and without docetaxel. The method comprises:

a. determining, for a sample derived from the subject, the expression of at least one biomolecule selected from the group consisting of CHD3, CAP1, GPM6B, GUSBP3, and derivatives thereof;
b. applying a model to the expression of said biomolecule(s) to calculate a predicted probability of pathological complete response (pCR) to a chemotherapy regimen;
c. classifying the predicted probability of pathological complete response (pCR) into a set of probability intervals (PIs) associated with the chemotherapy regimen;
d. determining a quantitative measure of chemotherapy outcome for the chemotherapy regimen, wherein the quantitative measure of chemotherapy outcome is predictive of the efficacy of the chemotherapy regimen for the subject.

As used herein, estrogen receptor (ER) status can also be indicative of a subject's response to certain chemotherapies. Similar to HER2, subjects can be classified as ER-positive or ER-negative based on detection of certain levels of ER in a given tumor sample.

An additional embodiment of the present invention is a method for predicting the efficacy of a chemotherapy regimen for a HER2-negative, lymph node-negative subject, wherein the chemotherapy regimen comprises anthracycline with docetaxel and without paclitaxel. The method comprises:
a. determining, for a sample derived from the subject, the expression of at least one biomolecule selected from the group consisting of CDKN2C, GNAI3, LMO4, PSRC1, USP1, STK38, and derivatives thereof;
b. applying a model to the expression of said biomolecule(s) to calculate a predicted probability of pathological complete response (pCR) to a chemotherapy regimen;
c. classifying the predicted probability of pathological complete response (pCR) into a set of probability intervals (PIs) associated with the chemotherapy regimen;
d. determining a quantitative measure of chemotherapy outcome for the chemotherapy regimen, wherein the quantitative measure of chemotherapy outcome is predictive of the efficacy of the chemotherapy regimen for the subject.

Another embodiment of the present invention is a method for predicting the efficacy of a chemotherapy regimen for a HER2-negative, lymph node-positive subject, wherein the chemotherapy regimen comprises anthracycline with paclitaxel and without docetaxel. The method comprises:
a. determining, for a sample derived from the subject, the expression of at least one biomolecule selected from the group consisting of NFIB, ROPN1B, and derivatives thereof;
b. applying a model to the expression of said biomolecule(s) to calculate a predicted probability of pathological complete response (pCR) to a chemotherapy regimen;
c. classifying the predicted probability of pathological complete response (pCR) into a set of probability intervals (PIs) associated with the chemotherapy regimen;
d. determining a quantitative measure of chemotherapy outcome for the chemotherapy regimen, wherein the quantitative measure of chemotherapy outcome is predictive of the efficacy of the chemotherapy regimen for the subject.

A further embodiment of the present invention is a method for predicting the efficacy of a chemotherapy regimen for a HER2-negative, lymph node-positive subject, wherein the chemotherapy regimen comprises anthracycline with docetaxel and without paclitaxel. The method comprises:

a. determining, for a sample derived from the subject, the expression of at least one biomolecule selected from the group consisting of TPX2, BAT2L1, PMP22, PTTG1, NME5, CENPA, BANK1, and derivatives thereof;
b. applying a model to the expression of said biomolecule(s) to calculate a predicted probability of pathological complete response (pCR) to a chemotherapy regimen;
c. classifying the predicted probability of pathological complete response (pCR) into a set of probability intervals (PIs) associated with the chemotherapy regimen;
d. determining a quantitative measure of chemotherapy outcome for the chemotherapy regimen, wherein the quantitative measure of chemotherapy outcome is predictive of the efficacy of the chemotherapy regimen for the subject.

Cancers, including breast cancers, can be further classified as lymph node-negative or lymph node-positive based on the absence or presence of cancer cells in a subject's lymph node(s). Lymph node status is typically determined from a biopsy of the lymph node, wherein the presence of cancer may be assessed by, for example, a pathologist.

In some embodiments, a subject's HER2/ER/lymph node status may be determined before utilizing a method or kit of the present invention in an effort to inform a medical professional which method or kit of the present invention is likely to be the most effective for the subject.

In some embodiments, the expression is selected from the group consisting of mRNA expression, protein expression, non-coding RNA expression, and miRNA expression.

An additional embodiment of the present invention is a method for selecting a chemotherapy regimen for a subject. The method comprises determining, for a sample derived from the subject, the expression of at least two biomolecules selected from the group consisting of: SLC12A7, GZMB, TAF6L, NFIB, METRN, ROPN1B, TTK, CCND1, PTTG1, H2AFZ, WDR45L, DEK, MCM2, USP1, CDT1, TMEM97, RER1, MCM6, LZTFL1, C11orf17, CCL5, XCL1, XCL2, MELK, CTSL2, TPX2, AURKA, CDKN2C, BRP44, PNP, SMC4, NR4A2, C3orf37, MTPAP, CDC25B, ABCF1, MTAP, SNAPC3, RANBP9, COIL, FAM86B1, ITGA6, S100P, RANBP1, PRSS16, SMARCA2, STK24, TSPYL5, SRI, LRP12, CENPF, TUBD1, KIAA1324, DBF4, CCNA2, DLGAP5, FHL1, SIRT3, GTSE1, PCNA, CCNE2, CHD3, CAP1, GPM6B, GUSBP3, GNAI3, LMO4, PSRC1, USP1, STK38, BAT2L1, PMP22, NME5, CENPA, BANK1, and derivatives thereof.

Another embodiment of the present invention is a method for selecting a chemotherapy regimen for a subject. The method comprises:
a. determining, for a sample derived from the subject, the expression of a first set of biomolecule(s) predictive of the efficacy of a first chemotherapy regimen;
b. applying a first model to the expression of the first set of biomolecule(s) to calculate a first predicted probability of pathological complete response (pCR) to a first chemotherapy regimen;
c. classifying the first predicted probability of pathological complete response (pCR) into a first set of probability intervals (PIs) associated with the first chemotherapy regimen; and,
d. determining a first quantitative measure of chemotherapy outcome for the first chemotherapy regimen, wherein the first quantitative measure of chemotherapy outcome is predictive of the efficacy of the first chemotherapy regimen for the subject.

In one aspect of this embodiment, the method further comprises:
a. determining, for a sample derived from the subject, the expression of a second set of biomolecule(s) predictive of the efficacy of a second chemotherapy regimen;
b. applying a second model to the expression of the second set of biomolecule(s) to calculate a second predicted probability of pathological complete response (pCR) to a second chemotherapy regimen;
c. classifying the second predicted probability of pathological complete response (pCR) into a second set of probability intervals (PIs) associated with the second chemotherapy regimen; and,
d. determining a second quantitative measure of chemotherapy outcome for the second chemotherapy regimen, wherein the second quantitative measure of chemotherapy outcome is predictive of the efficacy of the second chemotherapy regimen for the subject.

Preferably, the method further comprises:
a. determining, for a sample derived from the subject, the expression of a third set of biomolecule(s) predictive of the efficacy of a third chemotherapy regimen;
b. applying a third model to the expression of the third set of biomolecule(s) to calculate a third predicted probability of pathological complete response (pCR) to a third chemotherapy regimen;
c. classifying the third predicted probability of pathological complete response (pCR) into a third set of probability intervals (PIs) associated with the third chemotherapy regimen; and,
d. determining a third quantitative measure of chemotherapy outcome for the third chemotherapy regimen, wherein the third quantitative measure of chemotherapy outcome is predictive of the efficacy of the third chemotherapy regimen for the subject.

In another aspect of this embodiment, the first set of biomolecule(s) is at least one biomolecule selected from the biomolecules in Groups 1-14:
Group 1: SLC12A7, GZMB, TAF6L, and derivatives thereof;
Group 2: NFIB, METRN, ROPN1B, TTK, CCND1, and derivatives thereof;
Group 3: PTTG1, H2AFZ, WDR45L, DEK, MCM2, USP1, CDT1, TMEM97, RER1, MCM6, LZTFL1, and derivatives thereof;
Group 4: SLC12A7, GZMB, C11orf17, TAF6L, CCL5, XCL1, XCL2, and derivatives thereof;
Group 5: NFIB, ROPN1B, TTK, MELK, CTSL2, METRN, and derivatives thereof;
Group 6: TPX2, PTTG1, MCM2, MCM6, AURKA, CDKN2C, BRP44, H2AFZ, PNP, SMC4, DEK, TMEM97, NR4A2, C3orf37, LZTFL1, MTPAP, CDC25B, ABCF1, and derivatives thereof;
Group 7: NFIB, MTAP, SNAPC3, RANBP9, COIL, FAM86B1, ITGA6, S100P, RANBP1, PRSS16, SMARCA2, STK24, and derivatives thereof;
Group 8: TSPYL5, SRI, and derivatives thereof;
Group 9: LRP12, CENPF, TUBD1, KIAA1324, TTK, and derivatives thereof;
Group 10: DBF4, DEK, CDC25B, CCNA2, DLGAP5, MCM2, CDKN2C, FHL1, SIRT3, GTSE1, PCNA, CCNE2, and derivatives thereof;
Group 11: CHD3, CAP1, GPM6B, GUSBP3, and derivatives thereof;
Group 12: CDKN2C, GNAI3, LMO4, PSRC1, USP1, STK38, and derivatives thereof;
Group 13: NFIB, ROPN1B, and derivatives thereof;
Group 14: TPX2, BAT2L1, PMP22, PTTG1, NME5, CENPA, BANK1, and derivatives thereof.

In one embodiment, the second set of biomolecule(s) is at least one biomolecule selected from the biomolecules in Groups 1-14:
Group 1: SLC12A7, GZMB, TAF6L, and derivatives thereof;
Group 2: NFIB, METRN, ROPN1B, TTK, CCND1, and derivatives thereof;
Group 3: PTTG1, H2AFZ, WDR45L, DEK, MCM2, USP1, CDT1, TMEM97, RER1, MCM6, LZTFL1, and derivatives thereof;
Group 4: SLC12A7, GZMB, C11orf17, TAF6L, CCL5, XCL1, XCL2, and derivatives thereof;
Group 5: NFIB, ROPN1B, TTK, MELK, CTSL2, METRN, and derivatives thereof;
Group 6: TPX2, PTTG1, MCM2, MCM6, AURKA, CDKN2C, BRP44, H2AFZ, PNP, SMC4, DEK, TMEM97, NR4A2, C3orf37, LZTFL1, MTPAP, CDC25B, ABCF1, and derivatives thereof;
Group 7: NFIB, MTAP, SNAPC3, RANBP9, COIL, FAM86B1, ITGA6, S100P, RANBP1, PRSS16, SMARCA2, STK24, and derivatives thereof;
Group 8: TSPYL5, SRI, and derivatives thereof;
Group 9: LRP12, CENPF, TUBD1, KIAA1324, TTK, and derivatives thereof;
Group 10: DBF4, DEK, CDC25B, CCNA2, DLGAP5, MCM2, CDKN2C, FHL1, SIRT3, GTSE1, PCNA, CCNE2, and derivatives thereof;
Group 11: CHD3, CAP1, GPM6B, GUSBP3, and derivatives thereof;
Group 12: CDKN2C, GNAI3, LMO4, PSRC1, USP1, STK38, and derivatives thereof;
Group 13: NFIB, ROPN1B, and derivatives thereof;
Group 14: TPX2, BAT2L1, PMP22, PTTG1, NME5, CENPA, BANK1, and derivatives thereof.

In one embodiment, the third set of biomolecule(s) is at least one biomolecule selected from the biomolecules in Groups 1-6: Group 1: SLC12A7, GZMB, TAF6L, and derivatives thereof;
Group 2: NFIB, METRN, ROPN1B, TTK, CCND1, and derivatives thereof;
Group 3: PTTG1, H2AFZ, WDR45L, DEK, MCM2, USP1, CDT1, TMEM97, RER1, MCM6, LZTFL1, and derivatives thereof;
Group 4: SLC12A7, GZMB, C11orf17, TAF6L, CCL5, XCL1, XCL2, and derivatives thereof;
Group 5: NFIB, ROPN1B, TTK, MELK, CTSL2, METRN, and derivatives thereof;
Group 6: TPX2, PTTG1, MCM2, MCM6, AURKA, CDKN2C, BRP44, H2AFZ, PNP, SMC4, DEK, TMEM97, NR4A2, C3orf37, LZTFL1, MTPAP, CDC25B, ABCF1, and derivatives thereof.

In some embodiments, the expression is selected from the group consisting of mRNA expression, protein expression, non-coding RNA expression, and miRNA expression.

In some embodiments, a method for selecting a chemotherapy regimen for a subject may involve the use of biomolecules from a single set of biomolecules. Biomolecules from a single set of biomolecules may be useful to, for example, generate a quantitative measure of chemotherapy outcome that can assist, for example, a medical professional in determining whether a given chemotherapy regimen is likely to be effective for a patient. In some embodiments, a method for selecting a chemotherapy regimen for a subject may involve the use of biomolecules from two or more sets of biomolecules, including three sets of biomolecules. Biomolecules from multiple sets of biomolecules may be useful to, for example, generate quantitative measures of chemotherapy outcome for multiple chemotherapy regimens that can be compared to determine which chemotherapy regimen, out of those examined, is predicted to be the most effective for a given patient.

A further embodiment of the present invention is a method for selecting a biomarker predictive of the efficacy of a chemotherapy regimen. The method comprises:
a. screening a set of biomolecules using a random sampling screening (RSS) procedure to identify at least one genetic predictor;
b. generating a model incorporating at least one variable representing the genetic predictor(s), wherein the model outputs a quantitative measure of model performance;
c. determining a quantitative measure of model performance for said model;
d. at least once, repeating steps (b)-(c) to generate additional model(s) and corresponding quantitative measure(s) of model performance for said model(s);
e. selecting a biomarker from the set of biomolecules, the selected biomarker represented by one of the variables incorporated into one of the generated models having a locally optimal quantitative measure of model performance.

In one aspect of this embodiment, the method further comprises the initial step of determining a set of biomolecules that are differentially expressed in a first cohort of subjects exhibiting pathological complete response (pCR) upon administration of said chemotherapy regimen and a second cohort of subjects exhibiting residual disease (RD) upon administration of said chemotherapy regimen.

As used herein, a "biomarker" is any diagnostic marker, such as a biochemical marker, serological marker, genetic marker, or other clinical characteristic that can be used to predict the efficacy of a chemotherapy regimen. Biomarkers of the present invention include biomolecules and derivatives thereof of the present invention, such as, but not limited to, genes and gene fragments, and mRNA transcripts and protein products thereof. Biomarkers of the present invention may also include DNA modifications such as epigenetic modifications and modifications to the copy number of a given gene or gene fragment, post-transcriptionally modified RNA, and post-translationally modified proteins.

In some embodiments, "selecting a biomarker predictive of the efficacy of a chemotherapy regimen" includes selecting a biomolecule from any biomolecule present in or secreted by a cell of a given subject and is not meant to be limiting in any way.

In some embodiments, "screening" means using certain criteria to select one or more biomolecules from a given set of biomolecules.

As used herein, the terms "differential expression", "differentially expressed", and grammatical variations thereof refer to changes in the production levels of certain mRNA(s) and/or protein(s) in certain cells relative to other cells. Differential expression includes upregulation and downregulation of biomolecule(s). In some embodiments, "differentially expressed" biomolecules include biomolecules that are expressed at statistically significant disparate levels in subjects exhibiting pathological complete response (pCR) and subjects exhibiting residual disease (RD). Statistical significance can be measured using any measure of statistical significance, including those well known to one of skill in the art. Herein, statistical significance is preferably determined using a t-test, more preferably, a Welch two-sample t-test.

T-tests generate p-values as a measure of statistical significance. P-values less than or equal to 0.05 generally indicate statistical significance, but an appropriate p-value can be readily ascertained by one of skill in the art. Preferably, differentially expressed biomolecules of the present invention are associated with p-values of 0.05 or lower, including 0.01 or lower, 0.001 or lower, and 0.0001 or lower.

As used herein, residual disease (RD) has been previously defined (Kaufmann, et al., 2006, Kuerer, et al., 1999, von Minckwitz, et al., 2012).

In some embodiments, the set of differentially expressed biomolecules is screened using a random sampling screening (RSS) procedure to identify at least one genetic predictor. An example of a RSS procedure, as used herein, involves the following steps:
a. Randomly drawing a sample of probes $C_0$ from $S_0$;
b. Performing area under the curve random forest (AUCRF) or an alternative machine learning method on $C_0$ to produce a set of probes $R_0^{(x)}$, wherein x=1 unless defined otherwise in subsequent steps;
c. Adding the probes in $R_0^{(x)}$, to set of probes Sy, wherein y=1 unless defined otherwise in subsequent steps;
d. Repeating steps (a)-(c), wherein for each iteration of step b, x is increased by 1; and,
e. Repeating steps (a)-(d), wherein Sy is used in place of $S_0$, x is reset to 1 in the first iteration of step (b), and for each iteration of step c, y is increased by 1.

As used above, "probes" is synonymous with "biomolecules" as described above. Furthermore, S0 is defined by the set of differentially expressed biomolecules discussed above.

In some embodiments, a sample of probes C0 is limited only by the number of probes in $S_0$. Preferably, the sample of probes $C_0$ contains the minimum of the number of probes in $S_0/4$, or 500.

In some embodiments, step (d) of the RSS procedure is performed dozens of times. Preferably, step (d) of the RSS procedure is performed hundreds of times. More preferably, step (d) of the RSS procedure is performed 1000 times.

In some embodiments, step (e) of the RSS procedure is performed until the number of probes in Sy is equal to the number of probes in Sy−1 or is less than 50. The resulting probes in Sy, "genetic predictors," are then optionally used as input for AUCRF in order to rank the genetic predictors in terms of importance. As used herein, "genetic predictors" are biomolecules, preferably genes, that remain after a RSS procedure has been applied to the set of differentially expressed biomolecules.

In some embodiments, "generating at least one model incorporating at least one variable representing the genetic predictor(s), wherein the model outputs a quantitative measure of model performance" is performed as described above. Briefly, statistical models incorporating at least one variable representing at least one genetic predictor (i.e. a gene) may be generated by initially evaluating, for example, the f1-score of, for example, a random forest model incorporating only clinical variables. This first model can be evaluated by generating a quantitative measure of model performance for the first model. Then, additional variables, including at least one variable representing at least one genetic predictor, may be added to the model, producing additional models associated with additional quantitative measures of model performance. Preferably, if f1-score is used as a quantitative measure of model performance, a model associated with a high f1-score will be preferred over a model associated with a low f1-score.

In some embodiments, the at least one variable means at least one genetic predictor. For example, a variable in which expression of a genetic predictor is used as input. Other variables of the present invention include clinical variables such as, for example, age and weight of a subject.

As used herein, "determining a quantitative measure of model performance" is a procedure well known to those in the art and generally involves calculating a numerical representation of the quality of a model, such as accuracy, precision, recall, or combinations thereof of a given model.

In the current embodiment for selecting a biomarker predictive of the efficacy of a chemotherapy regimen, steps (b)-(c) may be repeated at least once to generate additional model(s) and corresponding quantitative measure(s) of model performance for said model(s), as described above. It is envisioned that steps (b)-(c) may be repeated any number of times to generate any number of models and corresponding quantitative measure(s) of model performance for said model(s). Preferably, repetition of these steps will end when a model is generated that yields a local maximum quantitative measure of model performance, as described above. More preferably, the local maximum quantitative measure of model performance is a first local maximum quantitative measure of model performance, as described above.

In some embodiments, "selecting a biomarker from the set of biomolecules, the selected biomarker represented by one of the variables incorporated into one of the generated models having a locally optimal quantitative measure of model performance" means that, from a model yielding a locally optimal quantitative measure of model performance, any of the biomarkers represented by any of the variables in said model may be selected. Furthermore, if a model yielding a locally optimal quantitative measure of model performance includes multiple variables representing multiple biomolecules, then multiple biomarkers may be selected from said biomolecules. As used herein, the term "optimal" as it relates to quantitative measures of model performance means a maximum or minimum value, depending on the quantitative measure of model performance used. For example, when using f1-scores, higher values are preferred over lower values. Likewise, an optimal quantitative measure of model performance when said measure is an f1-score is a maximum value.

An additional embodiment of the present invention is a system for selecting a chemotherapy regimen for a subject. The system comprises:

a. a data acquisition module configured to produce a data set from a sample derived from the subject, the data set comprising a diagnostic marker profile, wherein the diagnostic marker profile indicates the expression of at least one biomolecule predictive of the efficacy of a chemotherapy regimen selected from the group consisting of (i) anthracycline without paclitaxel or docetaxel, (ii) anthracycline with paclitaxel and without docetaxel, and (iii) anthracycline with docetaxel and without paclitaxel;
b. a data processing module configured to process the data set by applying a learning statistical classifier system to the data set to produce a statistically derived prediction of the efficacy of a chemotherapy regimen for the subject; and,
c. a display module configured to display the statistically derived prediction.

In some embodiments, the data acquisition module configured to produce a data set from a sample derived from the subject may be a computer system configured to, for example, collect data from an assay of the present invention used to determine expression of biomolecules of the present invention. For example, a computer system may be configured to collect data from, for example, a microarray containing detection agents specific for the biomolecules of the present invention. The data acquisition module may further be capable of transforming or otherwise sorting said collected data to output a data set comprising a diagnostic marker profile. It is envisioned that a data acquisition module of the present invention may be configured to collect data from an established database, without needing to acquire data from a particular assay. A diagnostic marker profile of the present invention may include, but is not limited to, data representing the expression of at least one biomolecule predictive of the efficacy of a chemotherapy regimen of the present invention in a sample of the present invention. In some embodiments, the diagnostic marker profile contains a subset of the data collected from an assay of the present invention.

In some embodiments, the data processing module is configured to process the data set by applying a learning statistical classifier system to the data set to product a statistically derived prediction of the efficacy of a chemotherapy regimen for the subject may be a computer system. The computer system may be the same computer system as the data acquisition module or a separate, distinct computer system.

In some embodiments, the learning statistical classifier system is a model, preferably a statistical model, disclosed above. As used herein, a statistical model includes any of a variety of mathematical algorithms used to determine relationships between independent variables (predictors) and response variables(s). In the present invention, variables may be clinical variables, such as a subject's age or weight, or genetic variables, such as the expression of a biomolecule predictive of the efficacy of a chemotherapy regimen in a sample derived from a subject. A statistical model of the present invention is not limited to any particular number of variables. Statistical models of the present invention can include one or more variables.

In some embodiments, learning statistical classifier systems include a machine learning technique capable of adapting to data sets and making decisions based upon such data sets. In some embodiments, one learning statistical classifier system is used. In some embodiments, combinations of learning statistical classifier systems are used. The learning statistical classifier systems described herein can be trained and tested using samples or data collected from samples of, for example, healthy subjects, subjects exhibiting pathological complete response (pCR) after administration of a chemotherapy regimen, and subjects exhibiting residual disease (RD) after administration of a chemotherapy regimen. Training and testing learning statistical classifier systems of the present invention is well known to those of skill in the art.

In some embodiments, the statistically derived prediction of the efficacy of a chemotherapy regimen for the subject may be a quantitative measure of chemotherapy outcome, such as a pCR score.

In some embodiments, a display module may be a screen capable of displaying visual information. Preferred display modules of the present invention include, but are not limited to, computer monitors, televisions, tablet displays, and smartphone displays.

In some embodiments, the expression is selected from the group consisting of mRNA expression, protein expression, non-coding RNA expression, and miRNA expression.

Figure 11:
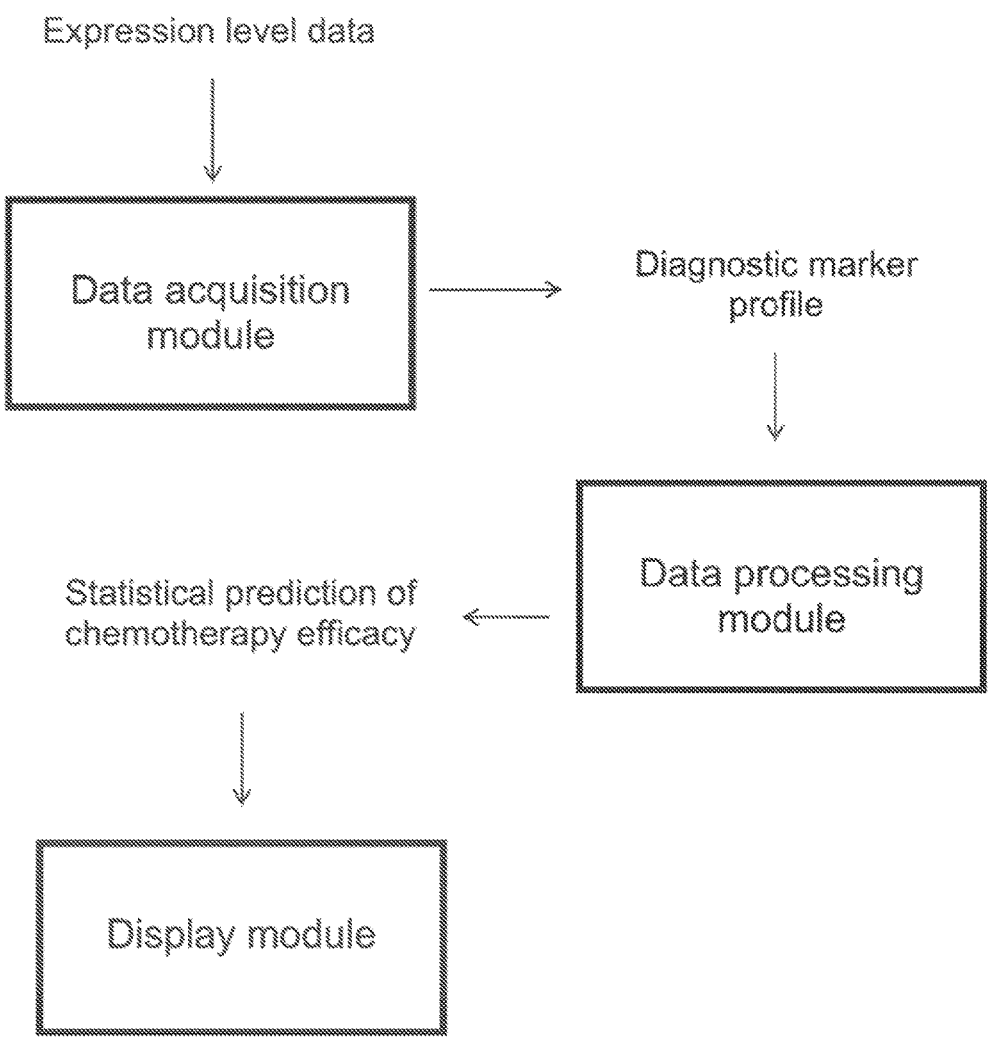
FIG. 11 shows a flowchart depicting a system of the present invention for selecting a chemotherapy regimen for a subject.

A representative system of the present invention is illustrated by way of a flowchart in FIG. 11.

In one embodiment, there is provided a method for treating a subject having breast cancer, comprising: (i) requesting an analysis of the expression of at least one gene selected from the group consisting of SLC12A7, GZMB, and TAF6L in a sample derived from the subject, thereby calculating a predicted probability of pathological complete response; and (ii) treating the subject with a chemotherapy regimen consisting of anthracycline based on a quantitative measure of chemotherapy outcome, said quantitative measure of chemotherapy outcome is derived from said predicted probability of pathological complete response.

In one embodiment, there is provided a method for treating a subject having breast cancer, comprising: (i) requesting an analysis of the expression of at least one gene selected from the group consisting of NFIB, METRN, ROPN1B, TTK, and CCND1 in a sample derived from the subject, thereby calculating a predicted probability of pathological complete response; and (ii) treating the subject with a chemotherapy regimen comprising anthracycline and paclitaxel based on a quantitative measure of chemotherapy outcome, said quantitative measure of chemotherapy outcome is derived from said predicted probability of pathological complete response.

In one embodiment, there is provided a method for treating a subject having breast cancer, comprising: (i) requesting an analysis of the expression of at least one gene selected from the group consisting of PTTG1, H2AFZ, WDR45L, DEK, MCM2, USP1, CDT1, TMEM97, RER1, MCM6, and LZTFL1 in a sample derived from the subject, thereby calculating a predicted probability of pathological complete response; and (ii) treating the subject with a chemotherapy regimen comprising anthracycline and docetaxel based on a quantitative measure of chemotherapy outcome, said quantitative measure of chemotherapy outcome is derived from said predicted probability of pathological complete response.

In one embodiment, there is provided a method for treating a subject having breast cancer, comprising: (a) requesting an analysis of the expression of (i) at least one gene selected from the group consisting of SLC12A7, GZMB, and TAF6L in a sample derived from the subject, thereby calculating a first predicted probability of pathological complete response, and (ii) at least one gene selected from the group consisting of NFIB, METRN, ROPN1B, TTK, and CCND1 in a sample derived from the subject, thereby calculating a second predicted probability of pathological complete response; and (b) treating the subject with a chemotherapy regimen consisting of anthracycline or comprising anthracycline and paclitaxel based on a quantitative measure of chemotherapy outcome, said quantitative measure of chemotherapy outcome is derived from said predicted probability of pathological complete response.

In one embodiment, there is provided a method for treating a subject having breast cancer, comprising: (a) requesting an analysis of the expression of (i) at least one gene selected from the group consisting of SLC12A7, GZMB, and TAF6L in a sample derived from the subject, thereby calculating a first predicted probability of pathological complete response, and (ii) at least one gene selected from the group consisting of PTTG1, H2AFZ, WDR45L, DEK, MCM2, USP1, CDT1, TMEM97, RER1, MCM6, and LZTFL1 in a sample derived from the subject, thereby calculating a second predicted probability of pathological complete response; and (b) treating the subject with a chemotherapy regimen consisting of anthracycline or comprising anthracycline and docetaxel based on a quantitative measure of chemotherapy outcome, said quantitative measure of chemotherapy outcome is derived from said predicted probability of pathological complete response.

In one embodiment, there is provided a method for treating a subject having breast cancer, comprising: (a) requesting an analysis of the expression of (i) at least one gene selected from the group consisting of NFIB, METRN, ROPN1B, TTK, and CCND1 in a sample derived from the subject, thereby calculating a first predicted probability of pathological complete response, and (ii) at least one gene selected from the group consisting of PTTG1, H2AFZ, WDR45L, DEK, MCM2, USP1, CDT1, TMEM97, RER1, MCM6, and LZTFL1 in a sample derived from the subject, thereby calculating a second predicted probability of pathological complete response; and (b) treating the subject with a chemotherapy regimen comprising anthracycline and paclitaxel or comprising anthracycline and docetaxel based on a quantitative measure of chemotherapy outcome, said quantitative measure of chemotherapy outcome is derived from said predicted probability of pathological complete response.

In one embodiment, there is provided a method for treating a subject having breast cancer, comprising: (a) requesting an analysis of the expression of (i) at least one gene selected from the group consisting of SLC12A7, GZMB, and TAF6L in a sample derived from the subject, thereby calculating a first predicted probability of pathological complete response, and (ii) at least one gene selected from the group consisting of NFIB, METRN, ROPN1B, TTK, and CCND1 in a sample derived from the subject, thereby calculating a second predicted probability of pathological complete response, and (iii) at least one gene selected from the group consisting of PTTG1, H2AFZ, WDR45L, DEK, MCM2, USP1, CDT1, TMEM97, RER1, MCM6, and LZTFL1 in a sample derived from the subject, thereby calculating a third predicted probability of pathological complete response; and (b) treating the subject with a chemotherapy regimen based on a quantitative measure of chemotherapy outcome, said quantitative measure of chemotherapy outcome is derived from said predicted probability of pathological complete response, wherein said chemotherapy regimen consists of anthracycline; or comprises anthracycline and paclitaxel; or comprises anthracycline and docetaxel.

In one embodiment, there is provided a method for treating a HER2-negative subject having breast cancer, comprising: (i) requesting an analysis of the expression of at least one gene selected from the group consisting of SLC12A7, GZMB, C11orf17, TAF6L, CCL5, XCL1, and XCL2 in a sample derived from the subject, thereby calculating a predicted probability of pathological complete response; and (ii) treating the subject with a chemotherapy regimen consisting of anthracycline based on a quantitative measure of chemotherapy outcome, said quantitative measure of chemotherapy outcome is derived from said predicted probability of pathological complete response.

In one embodiment, there is provided a method for treating a HER2-negative subject having breast cancer, comprising: (i) requesting an analysis of the expression of at least one gene selected from the group consisting of NFIB, ROPN1B, TTK, MELK, CTSL2, and METRN in a sample derived from the subject, thereby calculating a predicted probability of pathological complete response; and (ii) treating the subject with a chemotherapy regimen comprising anthracycline and paclitaxel based on a quantitative measure of chemotherapy outcome, said quantitative measure of chemotherapy outcome is derived from said predicted probability of pathological complete response.

In one embodiment, there is provided a method for treating a HER2-negative subject having breast cancer, comprising: (i) requesting an analysis of the expression of at least one gene selected from the group consisting of TPX2, PTTG1, MCM2, MCM6, AURKA, CDKN2C, BRP44, H2AFZ, PNP, SMC4, DEK, TMEM97, NR4A2, C3orf37, LZTFL1, MTPAP, CDC25B, and ABCF1 in a sample derived from the subject, thereby calculating a predicted probability of pathological complete response; and (ii) treating the subject with a chemotherapy regimen comprising anthracycline and docetaxel based on a quantitative measure of chemotherapy outcome, said quantitative measure of chemotherapy outcome is derived from said predicted probability of pathological complete response.

In one embodiment, there is provided a method for treating a HER2-negative, ER-negative subject having breast cancer, comprising: (i) requesting an analysis of the expression of at least one gene selected from the group consisting of NFIB, MTAP, SNAPC3, RANBP9, COIL, FAM86B1, ITGA6, S100P, RANBP1, PRSS16, SMARCA2, and STK24 in a sample derived from the subject, thereby calculating a predicted probability of pathological complete response; and (ii) treating the subject with a chemotherapy regimen comprising anthracycline and paclitaxel based on a quantitative measure of chemotherapy outcome, said quantitative measure of chemotherapy outcome is derived from said predicted probability of pathological complete response.

In one embodiment, there is provided a method for treating a HER2-negative, ER-negative subject having breast cancer, comprising: (i) requesting an analysis of the expression of at least one gene selected from the group consisting of TSPYL5 and SRI in a sample derived from the subject, thereby calculating a predicted probability of pathological complete response; and (ii) treating the subject with a chemotherapy regimen comprising anthracycline and docetaxel based on a quantitative measure of chemotherapy outcome, said quantitative measure of chemotherapy outcome is derived from said predicted probability of pathological complete response.

In one embodiment, there is provided a method for treating a HER2-negative, ER-positive subject having breast cancer, comprising: (i) requesting an analysis of the expression of at least one gene selected from the group consisting of LRP12, CENPF, TUBD1, KIAA1324, and TTK in a sample derived from the subject, thereby calculating a predicted probability of pathological complete response; and (ii) treating the subject with a chemotherapy regimen comprising anthracycline and paclitaxel based on a quantitative measure of chemotherapy outcome, said quantitative measure of chemotherapy outcome is derived from said predicted probability of pathological complete response.

In one embodiment, there is provided a method for treating a HER2-negative, ER-positive subject having breast cancer, comprising: (i) requesting an analysis of the expression of at least one gene selected from the group consisting of DBF4, DEK, CDC25B, CCNA2, DLGAP5, MCM2, CDKN2C, FHL1, SIRT3, GTSE1, PCNA, and CCNE2 in a sample derived from the subject, thereby calculating a predicted probability of pathological complete response; and (ii) treating the subject with a chemotherapy regimen comprising anthracycline and docetaxel based on a quantitative measure of chemotherapy outcome, said quantitative measure of chemotherapy outcome is derived from said predicted probability of pathological complete response.

In one embodiment, there is provided a method for treating a HER2-negative, lymph node-negative subject having breast cancer, comprising: (i) requesting an analysis of the expression of at least one gene selected from the group consisting of CHD3, CAP1, GPM6B, and GUSBP3 in a sample derived from the subject, thereby calculating a predicted probability of pathological complete response; and (ii) treating the subject with a chemotherapy regimen comprising anthracycline and paclitaxel based on a quantitative measure of chemotherapy outcome, said quantitative measure of chemotherapy outcome is derived from said predicted probability of pathological complete response.

In one embodiment, there is provided a method for treating a HER2-negative, lymph node-negative subject having breast cancer, comprising: (i) requesting an analysis of the expression of at least one gene selected from the group consisting of CDKN2C, GNAI3, LMO4, PSRC1, USP1, and STK38 in a sample derived from the subject, thereby calculating a predicted probability of pathological complete response; and (ii) treating the subject with a chemotherapy regimen comprising anthracycline and docetaxel based on a quantitative measure of chemotherapy outcome, said quantitative measure of chemotherapy outcome is derived from said predicted probability of pathological complete response.

In one embodiment, there is provided a method for treating a HER2-negative, lymph node-positive subject having breast cancer, comprising: (i) requesting an analysis of the expression of at least one gene selected from the group consisting of NFIB and ROPN1B in a sample derived from the subject, thereby calculating a predicted probability of pathological complete response; and (ii) treating the subject with a chemotherapy regimen comprising anthracycline and paclitaxel based on a quantitative measure of chemotherapy outcome, said quantitative measure of chemotherapy outcome is derived from said predicted probability of pathological complete response.

In one embodiment, there is provided a method for treating a HER2-negative, lymph node-positive subject having breast cancer, comprising: (i) requesting an analysis of the expression of at least one gene selected from the group consisting of TPX2, BAT2L1, PMP22, PTTG1, NME5, CENPA, and BANK1 in a sample derived from the subject, thereby calculating a predicted probability of pathological complete response; and (ii) treating the subject with a chemotherapy regimen comprising anthracycline and docetaxel based on a quantitative measure of chemotherapy outcome, said quantitative measure of chemotherapy outcome is derived from said predicted probability of pathological complete response.

In one embodiment, the gene expressions in the above methods can be mRNA expression, protein expression, non-coding RNA expression, or miRNA expression.

In one embodiment, the gene expression can be detected by a DNA array chip, a RNA array chip, an oligonucleotide array chip, a protein array chip, one or more antibody, one or more antigen binding fragment, a plurality of probes, or a set of primers.

In one embodiment, there is provided a kit for selecting a chemotherapy regimen for a subject having breast cancer, said kit comprises one or more components for detecting the expression of at least one gene selected from the group consisting of SLC12A7, GZMB, TAF6L, NFIB, METRN, ROPN1B, TTK, CCND1, PTTG1, H2AFZ, WDR45L, DEK, MCM2, USP1, CDT1, TMEM97, RER1, MCM6, LZTFL1, C11orf17, CCL5, XCL1, XCL2, MELK, CTSL2, TPX2, AURKA, CDKN2C, BRP44, PNP, SMC4, NR4A2, C3orf37, MTPAP, CDC25B, ABCF1, MTAP, SNAPC3, RANBP9, COIL, FAM86B1, ITGA6, S100P, RANBP1, PRSS16, SMARCA2, STK24, TSPYL5, SRI, LRP12, CENPF, TUBD1, KIAA1324, DBF4, CCNA2, DLGAP5, FHL1, SIRT3, GTSE1, PCNA, CCNE2, CHD3, CAP1, GPM6B, GUSBP3, GNAI3, LMO4, PSRC1, USP1, STK38, BAT2L1, PMP22, NME5, CENPA, and BANK1.

In one embodiment, the genes in the above kit comprise SLC12A7, GZMB, and TAF6L.

In one embodiment, the genes in the above kit comprise NFIB, METRN, ROPN1B, TTK, and CCND1.

In one embodiment, the genes in the above kit comprise PTTG1, H2AFZ, WDR45L, DEK, MCM2, USP1, CDT1, TMEM97, RER1, MCM6, and LZTFL1.

In one embodiment, the genes in the above kit comprise SLC12A7, GZMB, TAF6L, NFIB, METRN, ROPN1B, TTK, and CCND1.

In one embodiment, the genes in the above kit comprise SLC12A7, GZMB, TAF6L, PTTG1, H2AFZ, WDR45L, DEK, MCM2, USP1, CDT1, TMEM97, RER1, MCM6, and LZTFL1.

In one embodiment, the genes in the above kit comprise NFIB, METRN, ROPN1B, TTK, CCND1, PTTG1, H2AFZ, WDR45L, DEK, MCM2, USP1, CDT1, TMEM97, RER1, MCM6, and LZTFL1.

In one embodiment, the genes in the above kit comprise SLC12A7, GZMB, TAF6L, NFIB, METRN, ROPN1B, TTK, CCND1, PTTG1, H2AFZ, WDR45L, DEK, MCM2, USP1, CDT1, TMEM97, RER1, MCM6, and LZTFL1.

In one embodiment, the genes in the above kit comprise SLC12A7, GZMB, C11orf17, TAF6L, CCL5, XCL1, and XCL2.

In one embodiment, the genes in the above kit comprise NFIB, ROPN1B, TTK, MELK, CTSL2, and METRN.

In one embodiment, the genes in the above kit comprise TPX2, PTTG1, MCM2, MCM6, AURKA, CDKN2C, BRP44, H2AFZ, PNP, SMC4, DEK, TMEM97, NR4A2, C3orf37, LZTFL1, MTPAP, CDC25B, and ABCF1.

In one embodiment, the genes in the above kit comprise NFIB, MTAP, SNAPC3, RANBP9, COIL, FAM86B1, ITGA6, S100P, RANBP1, PRSS16, SMARCA2, and STK24.

In one embodiment, the genes in the above kit comprise TSPYL5 and SRI.

In one embodiment, the genes in the above kit comprise LRP12, CENPF, TUBD1, KIAA1324, and TTK.

In one embodiment, the genes in the above kit comprise DBF4, DEK, CDC25B, CCNA2, DLGAP5, MCM2, CDKN2C, FHL1, SIRT3, GTSE1, PCNA, and CCNE2.

In one embodiment, the genes in the above kit comprise CHD3, CAP1, GPM6B, and GUSBP3.

In one embodiment, the genes in the above kit comprise CDKN2C, GNAI3, LMO4, PSRC1, USP1, and STK38.

In one embodiment, the genes in the above kit comprise NFIB and ROPN1B.

In one embodiment, the genes in the above kit comprise TPX2, BAT2L1, PMP22, PTTG1, NME5, CENPA, and BANK1.

In one embodiment, the one or more components in the above kits can be a DNA array chip, a RNA array chip, an oligonucleotide array chip, a protein array chip, one or more antibody, one or more antigen binding fragment, a plurality of probes, or a set of primers.

In one embodiment, the present invention provides a method for treating a subject having breast cancer, comprising: (a) requesting an analysis in a sample derived from the subject one or more of the following: (i) the expression of at least one gene selected from the group consisting of SLC12A7, GZMB, and TAF6L; (ii) the expression of at least one gene selected from the group consisting of NFIB, METRN, ROPN1B, TTK, and CCND1; and (iii) the expression of at least one gene selected from the group consisting of PTTG1, H2AFZ, WDR45L, DEK, MCM2, USP1, CDT1, TMEM97, RER1, MCM6, and LZTFL1; (b) calculating one or more predicted probability of pathological complete response based on the gene expression results from (a); and (c) treating the subject with a chemotherapy regimen based on a quantitative measure of chemotherapy outcome derived from said predicted probability of pathological complete response, said chemotherapy regimen comprises (i) anthracycline without paclitaxel or docetaxel, or (ii) anthracycline and paclitaxel, or (iii) anthracycline and docetaxel.

In one embodiment, gene expression can be mRNA expression, protein expression, non-coding RNA expression, or miRNA expression. In one embodiment, the gene expression is detected by a DNA array chip, a RNA array chip, an oligonucleotide array chip, a protein array chip, one or more antibody, one or more antigen binding fragment, a plurality of probes, a set of primers, next generation sequencing (NGS) technology, or third generation sequencing technology.

In one embodiment, the present invention provides a method for treating a HER2-negative subject having breast cancer, comprising: (a) requesting an analysis in a sample derived from the subject one or more of the following: (i) the expression of at least one gene selected from the group consisting of SLC12A7, GZMB, C11orf17, TAF6L, CCL5, XCL1, and XCL2; (ii) the expression of at least one gene selected from the group consisting of CAP1, CENPF, CHD3, COIL, CTSL2, FAM86B1, GPM6B, GUSBP3, ITGA6, KIAA1324, LRP12, MELK, METRN, MTAP, NFIB, PRSS16, RANBP1, RANBP9, ROPN1B, S100P, SMARCA2, SNAPC3, STK24, TTK, and TUBD1; and (iii) the expression of at least one gene selected from the group consisting of ABCF1, AURKA, BANK1, BAT2L1, BRP44, C3orf37, CCNA2, CCNE2, CDC25B, CDKN2C, CENPA, DBF4, DEK, DLGAP5, FHL1, GNAI3, GTSE1, H2AFZ, LMO4, LZTFL1, MCM2, MCM6, MTPAP, NME5, NR4A2, PCNA, PNP, PMP22, PSRC1, PTTG1, SIRT3, SMC4, SRI, STK38, TMEM97, TPX2, TSPYL5 and USP1; (b) calculating one or more predicted probability of pathological complete response based on the gene expression results from (a); and (c) treating the subject with a chemotherapy regimen based on a quantitative measure of chemotherapy outcome derived from said predicted probability of pathological complete response, said chemotherapy regimen comprises (i) anthracycline without paclitaxel or docetaxel, or (ii) anthracycline and paclitaxel, or (iii) anthracycline and docetaxel. In one embodiment, the gene expression can be mRNA expression, protein expression, non-coding RNA expression, or miRNA expression. In one embodiment, the gene expression is detected by a DNA array chip, a RNA array chip, an oligonucleotide array chip, a protein array chip, one or more antibody, one or more antigen binding fragment, a plurality of probes, a set of primers, next generation sequencing (NGS) technology, or third generation sequencing technology.

In one embodiment, when the subject is HER2-negative, ER-negative, the method comprises requesting an analysis in a sample derived from the subject one or more of the following: the expression of at least one gene selected from the group consisting of NFIB, MTAP, SNAPC3, RANBP9, COIL, FAM86B1, ITGA6, S100P, RANBP1, PRSS16, SMARCA2, and STK24; and the expression of at least one gene selected from the group consisting of TSPYL5 and SRI.

In one embodiment, when the subject is HER2-negative, ER-positive, the method comprises requesting an analysis in a sample derived from the subject one or more of the following: the expression of at least one gene selected from the group consisting of LRP12, CENPF, TUBD1, KIAA1324, and TTK; and the expression of at least one gene selected from the group consisting of DBF4, DEK, CDC25B, CCNA2, DLGAP5, MCM2, CDKN2C, FHL1, SIRT3, GTSE1, PCNA, and CCNE2.

In one embodiment, when the subject is HER2-negative, lymph node-negative, the method comprises requesting an analysis in a sample derived from the subject one or more of the following: the expression of at least one gene selected from the group consisting of CHD3, CAP1, GPM6B, and GUSBP3; and the expression of at least one gene selected from the group consisting of CDKN2C, GNAI3, LMO4, PSRC1, USP1, and STK38.

In one embodiment, when the subject is HER2-negative, lymph node-positive, the method comprises requesting an analysis in a sample derived from the subject one or more of the following: the expression of at least one gene selected from the group consisting of NFIB and ROPN1B; and the expression of at least one gene selected from the group consisting of TPX2, BAT2L1, PMP22, PTTG1, NME5, CENPA, and BANK1.

The present invention also provides a kit for selecting a chemotherapy regimen for a subject having breast cancer, said kit comprises one or more agents for detecting the expression of at least one gene selected from the group consisting of SLC12A7, GZMB, TAF6L, NFIB, METRN, ROPN1B, TTK, CCND1, PTTG1, H2AFZ, WDR45L, DEK, MCM2, USP1, CDT1, TMEM97, RER1, MCM6, LZTFL1, C11orf17, CCL5, XCL1, XCL2, MELK, CTSL2, TPX2, AURKA, CDKN2C, BRP44, PNP, SMC4, NR4A2, C3orf37, MTPAP, CDC25B, ABCF1, MTAP, SNAPC3, RANBP9, COIL, FAM86B1, ITGA6, S100P, RANBP1, PRSS16, SMARCA2, STK24, TSPYL5, SRI, LRP12, CENPF, TUBD1, KIAA1324, DBF4, CCNA2, DLGAP5, FHL1, SIRT3, GTSE1, PCNA, CCNE2, CHD3, CAP1, GPM6B, GUSBP3, GNAI3, LMO4, PSRC1, USP1, STK38, BAT2L1, PMP22, NME5, CENPA, and BANK1. In one embodiment, the gene expression is detected by a DNA array chip, a RNA array chip, an oligonucleotide array chip, a protein array chip, one or more antibody, one or more antigen binding fragment, a plurality of probes, a set of primers, next generation sequencing (NGS) technology, or third generation sequencing technology.

Additional Definitions

In some embodiments of the present invention, the subject has cancer. Cancers of the present invention include, but are not limited to, adrenocortical carcinoma, anal tumor/cancer, bladder tumor/cancer, bone tumor/cancer (such as osteosarcoma), brain tumor, breast tumor/cancer, carcinoid tumor, carcinoma, cervical tumor/cancer, colon tumor/cancer, endometrial tumor/cancer, esophageal tumor/cancer, extrahepatic bile duct tumor/cancer, Ewing family of tumors, extracranial germ cell tumor, eye tumor/cancer, gallbladder tumor/cancer, gastric tumor/cancer, germ cell tumor, gestational trophoblastic tumor, head and neck tumor/cancer, hypopharyngeal tumor/cancer, islet cell carcinoma, kidney tumor/cancer, laryngeal tumor/cancer, leukemia, lip and oral cavity tumor/cancer, liver tumor/cancer, lung tumor/cancer, lymphoma, malignant mesothelioma, Merkel cell carcinoma, mycosis fungoides, myelodysplastic syndrome, myeloproliferative disorders, nasopharyngeal tumor/cancer, neuroblastoma, oral tumor/cancer, oropharyngeal tumor/cancer, osteosarcoma, ovarian epithelial tumor/cancer, ovarian germ cell tumor, pancreatic tumor/cancer, paranasal sinus and nasal cavity tumor/cancer, parathyroid tumor/cancer, penile tumor/cancer, pituitary tumor/cancer, plasma cell neoplasm, prostate tumor/cancer, rhabdomyosarcoma, rectal tumor/cancer, renal cell tumor/cancer, transitional cell tumor/cancer of the renal pelvis and ureter, salivary gland tumor/cancer, Sezary syndrome, skin tumors (such as cutaneous t-cell lymphoma, Kaposi's sarcoma, mast cell tumor, and melanoma), small intestine tumor/cancer, soft tissue sarcoma, stomach tumor/cancer, testicular tumor/cancer, thymoma, thyroid tumor/cancer, urethral tumor/cancer, uterine tumor/cancer, vaginal tumor/cancer, vulvar tumor/cancer, and Wilms' tumor. In preferred embodiments, the subject has breast cancer.

In some embodiments of the present invention, the detection agents comprise nucleic acids. "Nucleic acid" or "oligonucleotide" or "polynucleotide" used herein mean at least two nucleotides covalently linked together. Many variants of a nucleic acid may be used for the same purpose as a given nucleic acid. Thus, a nucleic acid also encompasses substantially identical nucleic acids and complements thereof.

Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be synthesized as a single stranded molecule or expressed in a cell (in vitro or in vivo) using a synthetic gene. Nucleic acids may be obtained by chemical synthesis methods or by recombinant methods.

The nucleic acid may also be a RNA such as a mRNA, tRNA, short hairpin RNA (shRNA), short interfering RNA (siRNA), double-stranded RNA (dsRNA), transcriptional gene silencing RNA (ptgsRNA), Piwi-interacting RNA, pri-miRNA, pre-miRNA, micro-RNA (miRNA), or anti-miRNA, as described, e.g., in U.S. patent application Ser. Nos. 11/429,720, 11/384,049, 11/418,870, and 11/429,720 and Published International Application Nos. WO 2005/116250 and WO 2006/126040.

siRNA gene-targeting may be carried out by transient siRNA transfer into cells, achieved by such classic methods as lipid-mediated transfection (such as encapsulation in liposome, complexing with cationic lipids, cholesterol, and/or condensing polymers, electroporation, or microinjection). siRNA gene-targeting may also be carried out by administration of siRNA conjugated with antibodies or siRNA complexed with a fusion protein comprising a cell-penetrating peptide conjugated to a double-stranded (ds) RNA-binding domain (DRBD) that binds to the siRNA (see, e.g., U.S. Patent Application Publication No. 2009/0093026).

An shRNA molecule has two sequence regions that are reversely complementary to one another and can form a double strand with one another in an intramolecular manner. shRNA gene-targeting may be carried out by using a vector introduced into cells, such as viral vectors (lentiviral vectors, adenoviral vectors, or adeno-associated viral vectors for example). The design and synthesis of siRNA and shRNA molecules are known in the art, and may be commercially purchased from, e.g., Gene Link (Hawthorne, N.Y.), Invitrogen Corp. (Carlsbad, Calif.), Thermo Fisher Scientific, and Dharmacon Products (Lafayette, Colo.).

The nucleic acid may also be an aptamer, an intramer, or a spiegelmer. The term "aptamer" refers to a nucleic acid or oligonucleotide molecule that binds to a specific molecular target. Aptamers are derived from an in vitro evolutionary process (e.g., SELEX (Systematic Evolution of Ligands by EXponential Enrichment), disclosed in U.S. Pat. No. 5,270,163), which selects for target-specific aptamer sequences from large combinatorial libraries. Aptamer compositions may be double-stranded or single-stranded, and may include deoxyribonucleotides, ribonucleotides, nucleotide derivatives, or other nucleotide-like molecules. The nucleotide components of an aptamer may have modified sugar groups (e.g., the 2'-OH group of a ribonucleotide may be replaced by 2'-F or 2'-NH$_2$), which may improve a desired property, e.g., resistance to nucleases or longer lifetime in blood. Aptamers may be conjugated to other molecules, e.g., a high molecular weight carrier to slow clearance of the aptamer from the circulatory system. Aptamers may be specifically cross-linked to their cognate ligands, e.g., by photo-activation of a cross-linker (Brody, E. N. and L. Gold (2000) J. Biotechnol. 74:5-13).

The term "intramer" refers to an aptamer which is expressed in vivo. For example, a vaccinia virus-based RNA expression system has been used to express specific RNA aptamers at high levels in the cytoplasm of leukocytes (Blind, M. et al. (1999) Proc. Natl. Acad. Sci. USA 96:3606-3610).

The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those disclosed in U.S. Pat. Nos. 5,235,033 and 5,034,506. Nucleic acids containing one or more non-naturally occurring or modified nucleotides are also included within the definition of nucleic acid. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5- bromo uridine; adenosines and guanosines modified at the 8-position, e.g. 8-bromo guanosine; deaza nucleotides, e.g. 7-deazaadenosine; O- and N-alkylated nucleotides, e.g. N6-methyl adenosine are suitable. The 2'-OH-group may be replaced by a group selected from H, OR, R, halo, SH, SR, NH$_2$, NHR, NR$_2$ or CN, wherein R is C$_1$-C$_6$ alkyl, alkenyl or alkynyl and halo is F, Cl, Br or I. Modified nucleotides also include nucleotides conjugated with cholesterol through, e.g., a hydroxyprolinol linkage as disclosed in Krutzfeldt et al., Nature (Oct. 30, 2005), Soutschek et al., Nature 432:173-178 (2004), and U.S. Patent Application Publication No. 20050107325. Modified nucleotides and nucleic acids may also include locked nucleic acids (LNA), as disclosed in U.S. Patent Application Publication No. 20020115080. Additional modified nucleotides and nucleic acids are disclosed in U.S. Patent Application Publication No. 20050182005. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

In some embodiments, the detection agents are proteins. The terms "peptide," "polypeptide," and "protein" are used interchangeably herein. In the present invention, these terms mean a linked sequence of amino acids, which may be natural, synthetic, or a modification, or combination of natural and synthetic. The term includes antibodies, antibody mimetics, domain antibodies, lipocalins, targeted proteases, and polypeptide mimetics. The term also includes vaccines containing a peptide or peptide fragment intended to raise antibodies against the peptide or peptide fragment.

In some embodiments, the detection agents are antibodies. As used herein, an "antibody" and "antigen-binding fragments thereof" encompass naturally occurring immunoglobulins (e.g., IgM, IgG, IgD, IgA, IgE, etc.) as well as non-naturally occurring immunoglobulins, including, for example, single chain antibodies, chimeric antibodies (e.g., humanized murine antibodies), heteroconjugate antibodies (e.g., bispecific antibodies), and Fab', F(ab')2, Fab, Fv, and rIgG. See also, e.g., Pierce Catalog and Handbook, 1994-1995 (Pierce Chemical Co., Rockford, Ill.); Kuby, et al., 1998. As used herein, "antigen-binding fragments" mean that a portion of the full length antibody that retains the ability to recognize the antigen, as well as various combinations of such portions.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

Full length antibodies can be proteolytically digested down to several discrete, functional antibody fragments, which retain the ability to recognize the antigen. For example, the enzyme papain can be used to cleave a full length immunoglobulin into two Fab fragments and an Fc fragment. Thus, the Fab fragment is typically composed of two variable domains and two constant domains from the heavy and light chains. The Fv region is usually recognized as a component of the Fab region and typically comprises two variable domains, one from each of the heavy (V$_H$, "heavy chain variable region", as used herein) and light (V$_L$ "light chain variable region", as used herein) chains. The enzyme pepsin cleaves below the hinge region, so a F(ab')2 fragment and a pFc' fragment is formed. F(ab')2 fragments are intact antibodies that have been digested, removing the constant (Fc) region. Two Fab' fragments can then result from further digestion of F(ab')2 fragments. Examples of antigen-binding fragments include, but are not limited to, Fv, Fab, Fab', Fab'-SH, F(ab')2, diabodies, tribodies, scFvs, and single-domain antibodies (dAbs).

Typically, a full length antibody has at least one heavy and at least one light chain. Each heavy chain contains a variable domain ($V_H$) and typically three or more constant domains ($C_H1$, $C_H2$, $C_H3$, etc.), while each light chain contains a variable domain ($V_L$) and a constant domain $C_L$. Light and heavy chain variable regions contain four "framework" regions interrupted by three hypervariable regions, also called "complementarity-determining regions" or "CDRs". The extent of the framework regions and CDRs have been defined. See, e.g., Kabat et al., U.S. Dept. of Health and Human Services, Sequences of Proteins of Immunological Interest (1983) and Chothia et al., J. Mol. Biol. 196:901-917 (1987). The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody, whereas a $V_L$ CDR1 is the CDR1 from the variable domain of the light chain of the antibody.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256: 495 (1975), and as modified by the somatic hybridization method as set forth above; or may be made by other recombinant DNA methods (see, e.g., U.S. Pat. No. 4,816, 567).

Additional types of antibodies that may be part of the monoclonal antibodies of the present invention include, but are not limited to, chimeric, humanized, and human antibodies. For application in man, it is often desirable to reduce immunogenicity of antibodies originally derived from other species, like mouse. This can be done by construction of chimeric antibodies, or by a process called "humanization". In this context, a "chimeric antibody" is understood to be an antibody comprising a domain (e.g. a variable domain) derived from one species (e.g. mouse) fused to a domain (e.g. the constant domains) derived from a different species (e.g. human).

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the framework (FR) regions are those of a human immunoglobulin sequence. The humanized antibody optionally also will comprise at least a portion of an immunoglobulin constant region (Fc), typically that of a human immunoglobulin (Jones et al., Nature 321:522-525 (1986); Riechmann et al., Nature 332:323-329 (1988); and Presta, Curr. Op. Struct. Biol 2:593-596 (1992)). Humanization can be essentially performed following the method of Winter and co-workers (Jones et al., Nature 321:522-525 (1986); Riechmann et al., Nature 332:323-3'27 (1988); Verhoeyen et al., Science 239:1534-1536 (1988)), by substituting rodent CDRs or CDR sequences for the corresponding sequences of a human antibody.

Furthermore, technologies have been developed for creating antibodies based on sequences derived from the human genome, for example by phage display or using transgenic animals (WO 90/05144; D. Marks, H. R. Hoogenboom, T. P. Bonnert, J. McCafferty, A. D. Griffiths and G. Winter (1991) "By-passing immunisation. Human antibodies from V-gene libraries displayed on phage." J. Mol. Biol., 222, 581-597; Knappik et al., J. Mol. Biol. 296: 57-86, 2000; Carmen and L. Jermutus, "Concepts in antibody phage display". Briefings in Functional Genomics and Proteomics 2002 1(2):189-203; Lonberg N, Huszar D. "Human antibodies from transgenic mice". Int Rev Immunol. 1995; 13(1):65-93.; Bruggemann M, Taussig M J. "Production of human antibody repertoires in transgenic mice". Curr Opin Biotechnol. 1997 August; 8(4):455-8.). Such antibodies are "human antibodies" in the context of the present invention.

As used herein, "recombinant" antibody means any antibody whose production involves expression of a non-native DNA sequence encoding the desired antibody structure in an organism. In the present invention, recombinant antibodies include tandem scFv (taFv or $scFv_2$), diabody, $dAb_2/VHH_2$, knob-into-holes derivatives, SEED-IgG, heteroFc-scFv, Fab-scFv, scFv-Jun/Fos, Fab'-Jun/Fos, tribody, $DNL-F(ab)_3$, $scFv_3$-CH1/CL, Fab-$scFv_2$, IgG-scFab, IgG-scFv, scFv-IgG, $scFv_2$-Fc, $F(ab')_2$-$scFv_2$, scDB-Fc, scDb-CH3, Db-Fc, $scFv_2$-H/L, DVD-Ig, tandAb, scFv-dhlx-scFv, $dAb_2$-IgG, dAb-IgG, dAb-Fc-dAb, and combinations thereof.

Variable regions of antibodies are typically isolated as single-chain Fv (scFv) or Fab fragments. ScFv fragments are composed of $V_H$ and $V_L$ domains linked by a short 10-25 amino acid linker. Once isolated, scFv fragments can be genetically linked with a flexible peptide linker such as, for example, one or more repeats of Ala-Ala-Ala, Gly-Gly-Gly-Gly-Ser, etc. The resultant peptide, a tandem scFv (taFv or $scFv_2$) can be arranged in various ways, with $V_H$-$V_L$ or $V_L$-$V_H$ ordering for each scFv of the taFv. (Kontermann, R. E. In: Bispecific Antibodies. Kontermann R E (ed.), Springer Heidelberg Dordrecht London New York, pp. 1-28 (2011)).

As used herein, the term "epitope" refers to the portion of the antigen which is recognized by the antibody or antigen binding fragment. A single antigen (such as an antigenic polypeptide) may have more than one epitope. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. Epitopes formed from contiguous amino acids are typically retained on exposure to denaturing solvents, whereas epitopes formed by tertiary folding are typically lost on treatment with denaturing solvents.

The following examples are provided to further illustrate the methods of the present invention. These examples are illustrative only and are not intended to limit the scope of the invention in any way.

EXAMPLES

Example 1

Materials and Methods 1111 breast cancer tumor samples were collected from 7 data series in GEO database (Gene Expression Omnibus (Takada, et al., 2012, Albain, et al., 2010)) (Table 2). Samples were grouped into 3 treatment groups: A group (anthracycline only), TA group (paclitaxel and anthracycline), and TxA group (docetaxel and anthracycline). R (Liu, et al., 2012) package Affyio (Edgar, et al., 2002) was used to read and normalize the Affymetrix® data. The responses for all samples were coded as pathological complete response (pCR) or Residual Disease (RD).

2. Perform AUCRF (Calle, et al., 2011) using the set of probes in $C_0$ and record the resulting set of probes selected by AUCRF as $R_0^{(1)}$;
3. Repeat (1) and (2) 1000 times, record all the probes that appeared in $R_0^{(1)}, \ldots, R_0^{(1000)}$ as $S_1$;
4. Replace $S_0$ with $S_1$, redo (1), (2), and (3); in (3), instead of keeping all probes that appear, now keep only the ones with occurrence rate (the ratio of number of times being selected and number of total samples (1000)) over 50%;
5. Repeat (4) until some iteration n where the size of $S_n$ is either the same as $S_n-1$ or smaller than 50.

$S_n$ was the final set of candidates discovered by RSS. Next, AUCRF was run on $S_n$, and the probes in $S_n$ were ranked by their importance.

Given the fact that the datasets were unbalanced (more patients with RD than pCR), the f1-score along with positive precision and positive recall were used as measures of model performance instead of accuracy. F1-score is defined as 2 $\Box\Box$ precision $\Box\Box$ recall/(precision+recall). The f1-score was calculated from a 10-fold cross-validation, where the screening procedure was conducted as described earlier on each training fold independently to obtain the candidate sets: $S_{n1}, \ldots, S_{n10}$.

TABLE 2

GEO Data Sets Used and Number of Patients in Each Data Set *

| GEO Accession Number | Treatment | | | Total |
|---|---|---|---|---|
| | Anthracycline (A) | Paclitaxel and Anthracycline (TA) | Docetaxel and Anthracycline (TxA) | |
| GSE20194 (Popovici, et al., 2010) | 4 (0) | 257 (20.6%) | 8 (12.5%) | 269 (20.1%) |
| GSE20271 (Tabchy, et al., 2010) | 85 (8.2%) | 91 (20.9%) | — | 176 (14.8%) |
| GSE22093 (iwamoto, et al., 2011) | 50 (10%) | — | — | 50 (10%) |
| GSE23988 (Iwamoto, et al., 2011) | — | — | 61 (32.8%) | 61 (32.8%) |
| GSE25055 (Hatzis, et al., 2011) | — | 290 (18.3%) | — | 290 (18.3%) |
| GSE25065 (Hatzis, et al., 2011) | — | 92 (20.7%) | 88 (26.1%) | 180 (23.3%) |
| GSE42822 (Shen., et al., 2012) | — | — | 85 (42.4%) | 85 (42.4%) |
| Total | 139 (8.6%) | 730 (19.7%) | 242 (33.1%) | 1111 (21.2%) |

* Values in parentheses are the percentage of patients who have pCR among the patients in the corresponding group.

Model Building and Evaluation

A flowchart of the method used herein is shown in FIG. 1. First, a Welch two-sample t-test was conducted to find differentially expressed probes between pCR and RD response groups. Using a significance level of 0.05, only the set of probes more likely to be truly significant were selected. This set of candidates was called $S_0$.

Figure 2A:
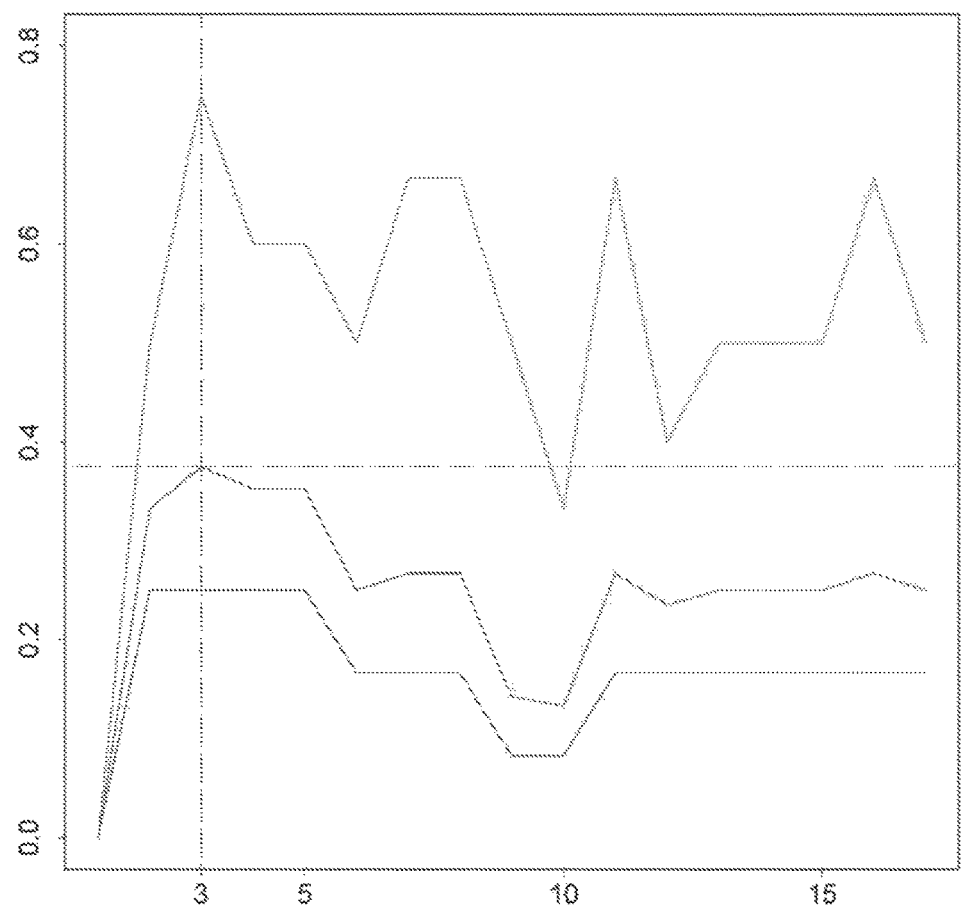
FIG. 2 shows model evaluation on 10-fold cross-validation. Three plots are shown corresponding to treatment with anthracycline (A) only (FIG. 2A), anthracycline and paclitaxel (TA) (FIG. 2B), and anthracycline and docetaxel (TxA) (FIG. 2C). The bottom lines in each figure represent positive recall, the middle lines in each figure represent f1-score, and the top lines in each figure represent positive precision. The suitable numbers of probes in each model were 3, 7, and 12, for A only, TA, and TxA treatments, respectively.
Figure 2B:
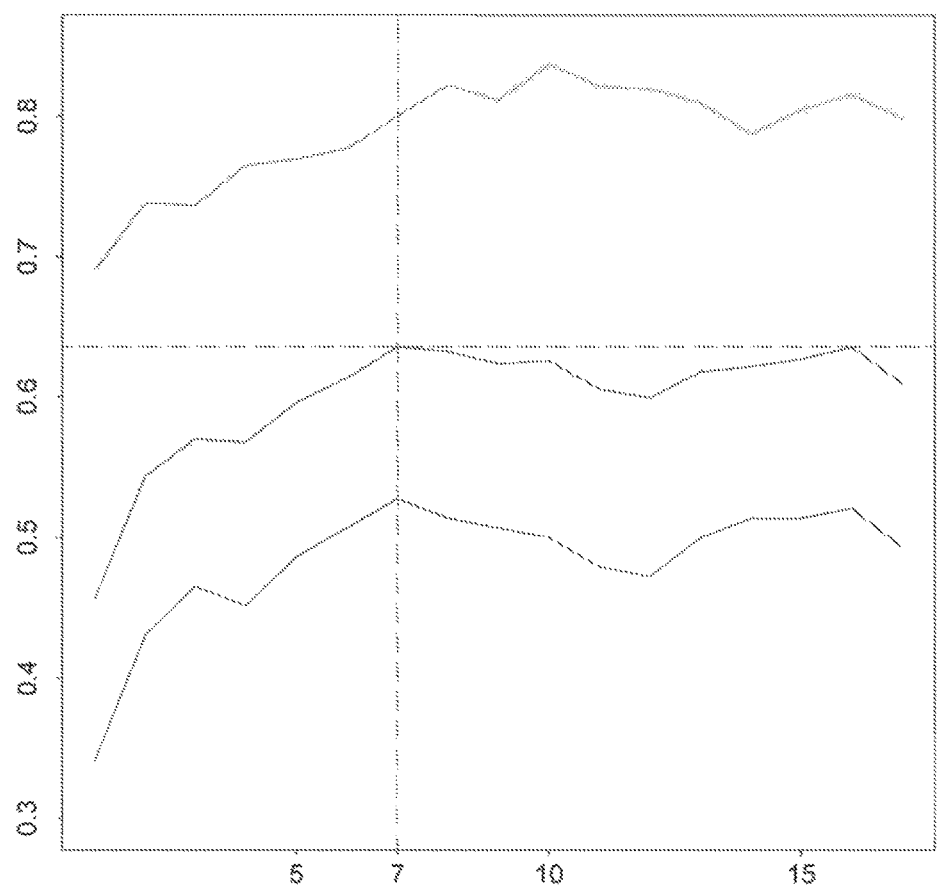
Figure 2C:
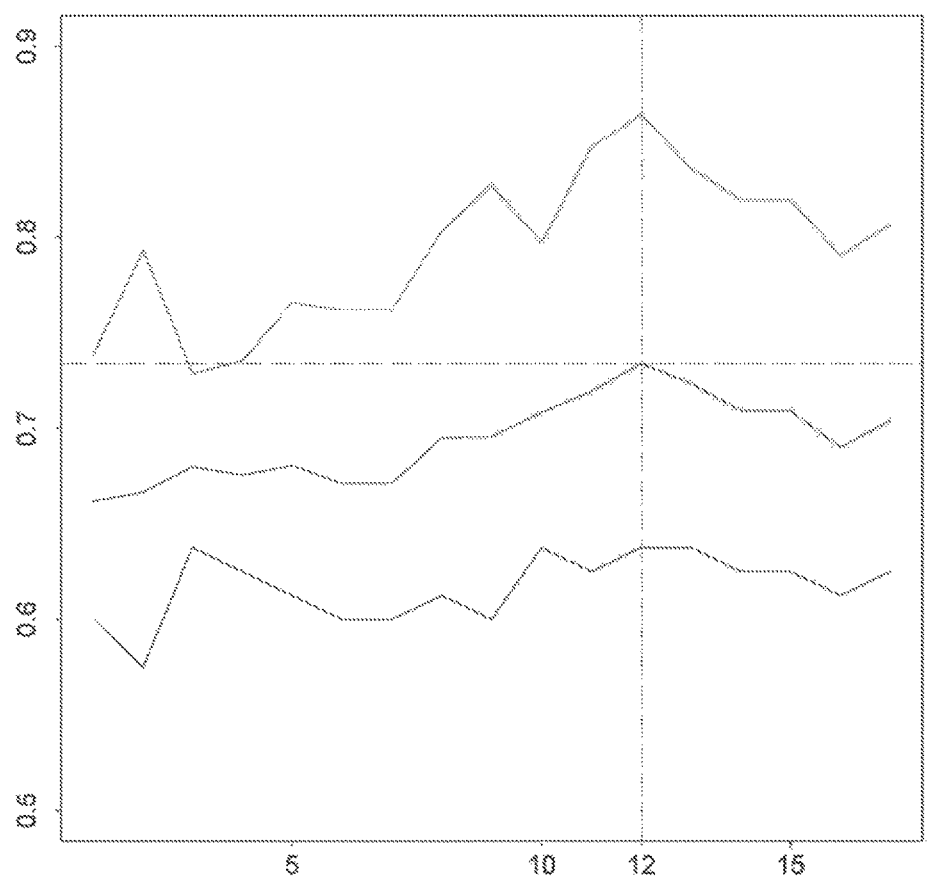
Figure 3A:
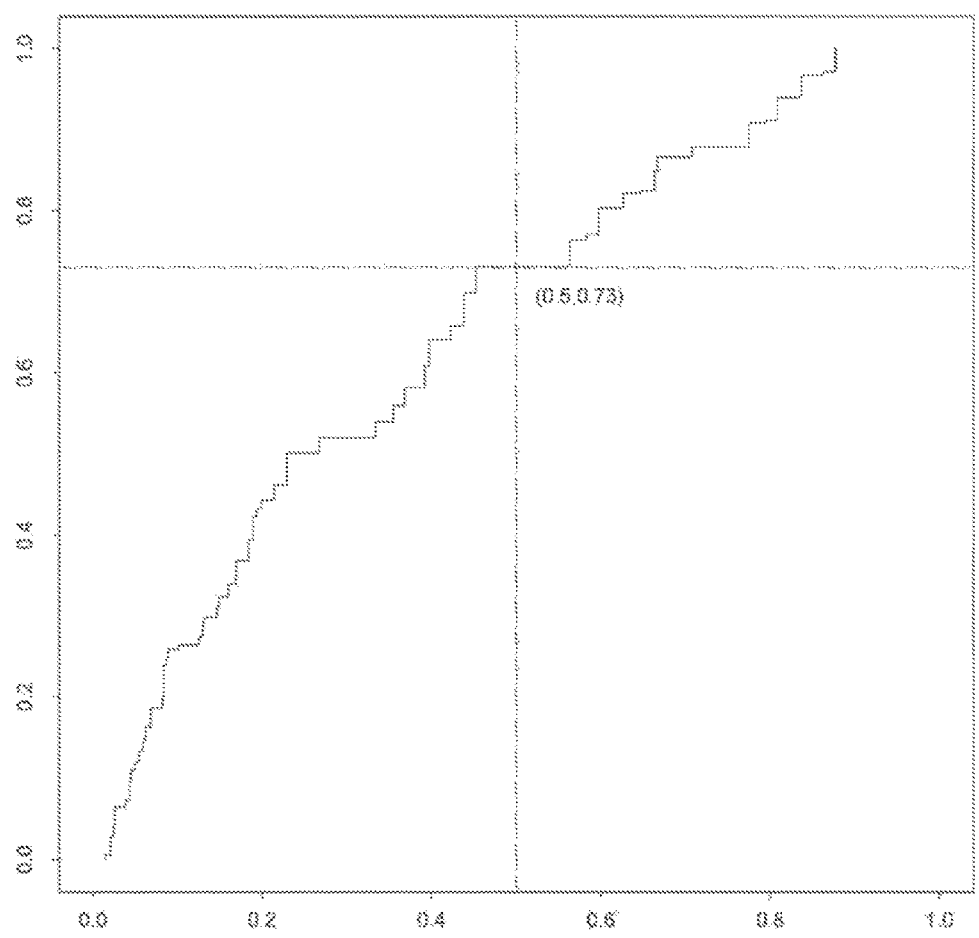
FIG. 3A shows a plot for all patients.
Figure 3B:
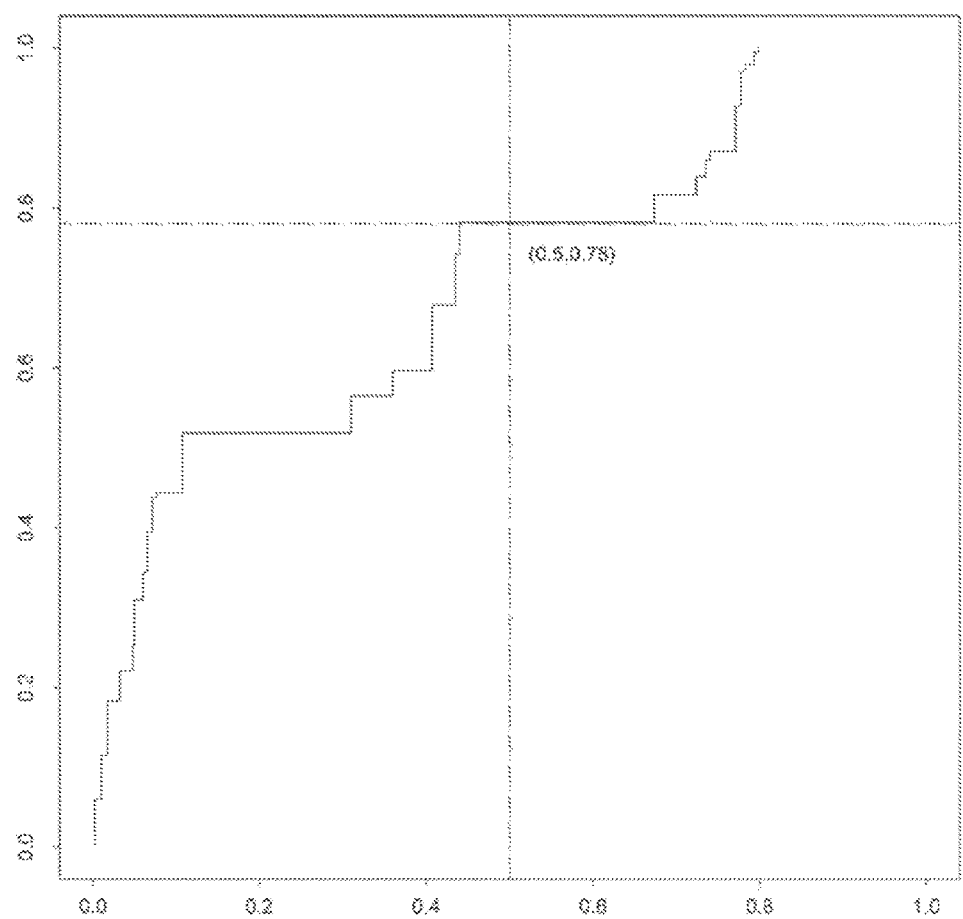
FIG. 3B shows a plot for HER2-negative, ER-negative patients. FIG.
Figure 3C:
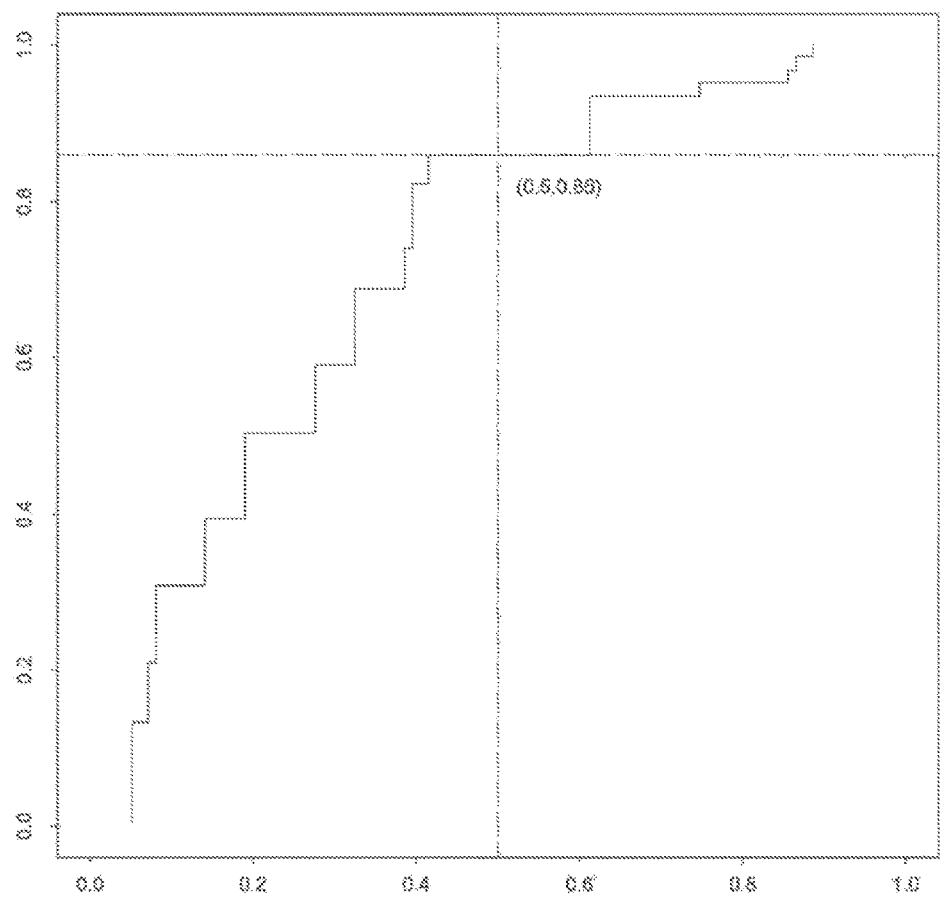
FIG. 3 shows plots of the empirical cumulative distribution of the absolute difference of pCR scores. In each plot, the horizontal axis represents the absolute difference of pCR scores and the vertical axis represents the proportion of patients.
FIG. 3D shows a plot of HER2-negative patients.
FIG. 3E shows a plot of HER2-negative, ER-positive patients.
FIG. 3F shows a plot of HER2-negative, Node-positive patients.
Figure 3D:
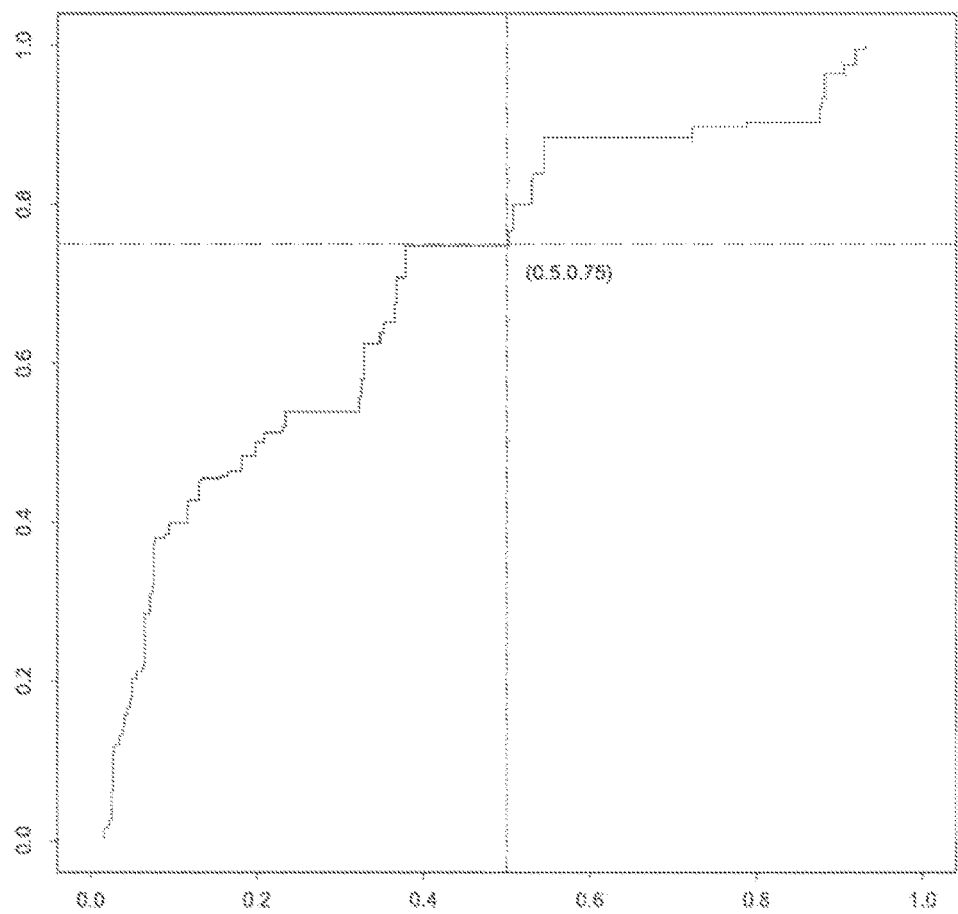
Figure 3E:
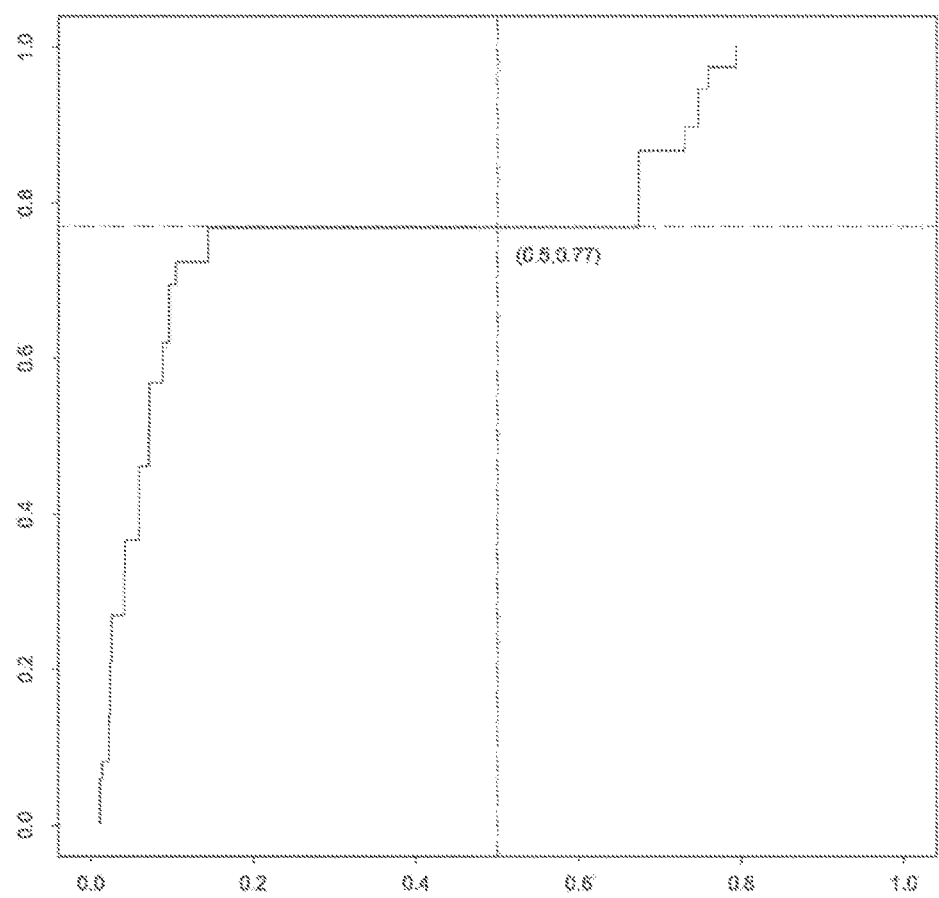
Figure 3F:
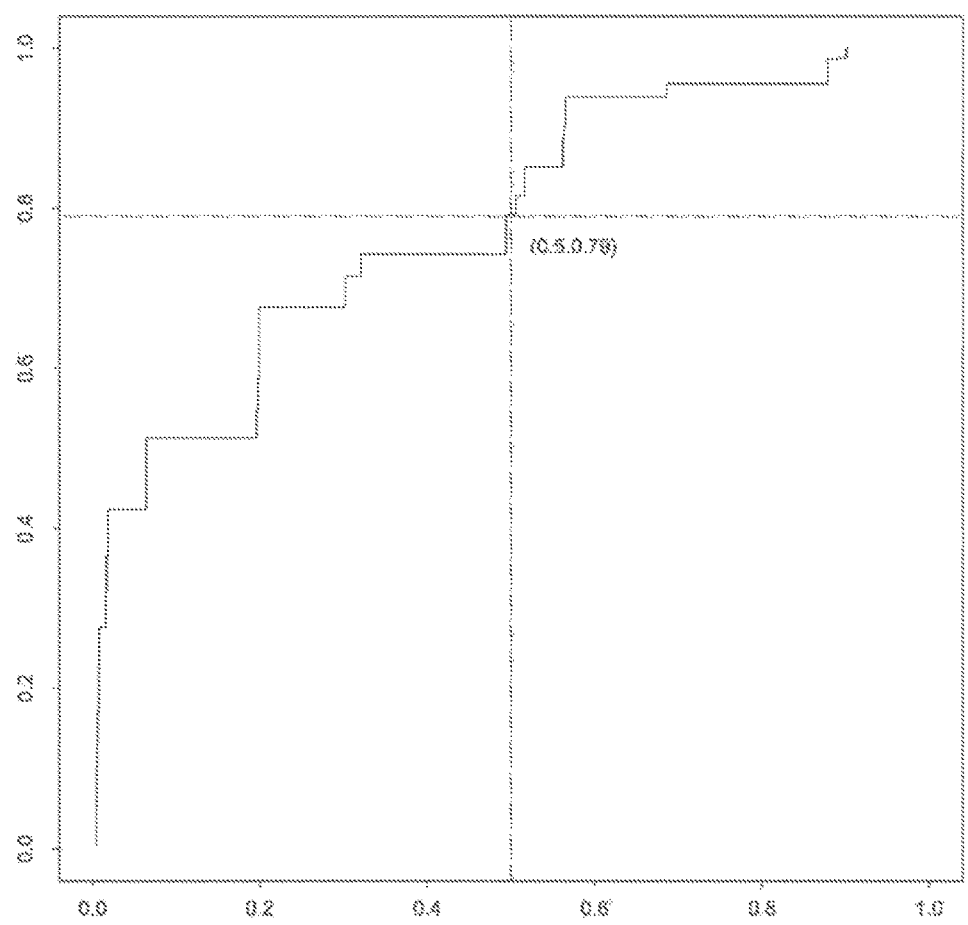
Figure 4A:
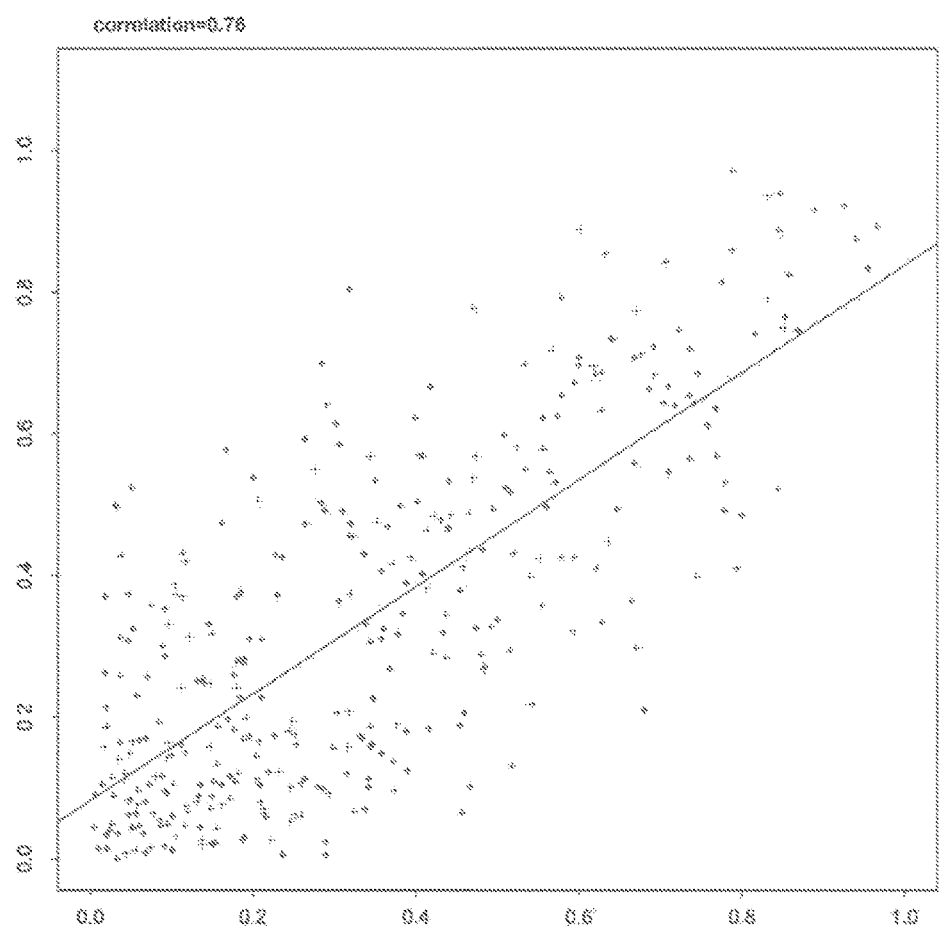
FIG. 4A shows a plot for the TA model for ER-negative patients.
Figure 4B:
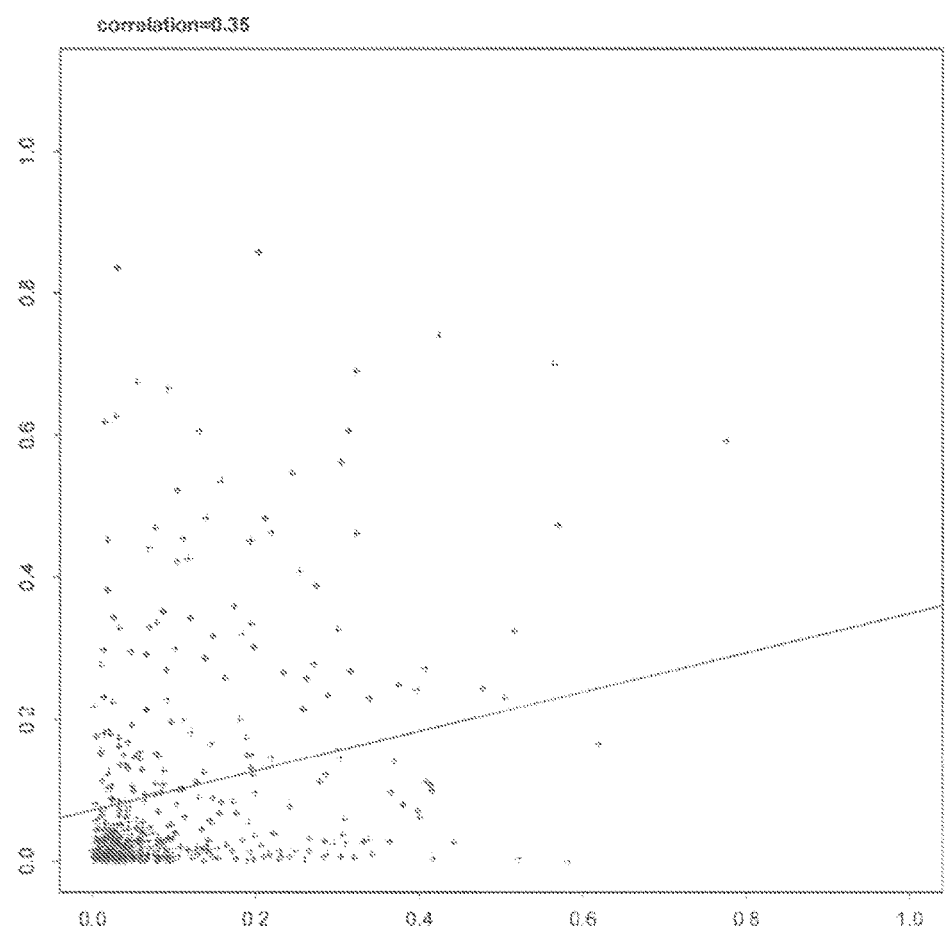
FIG. 4B shows a plot for the TA model for ER-positive patients.
Figure 4C:
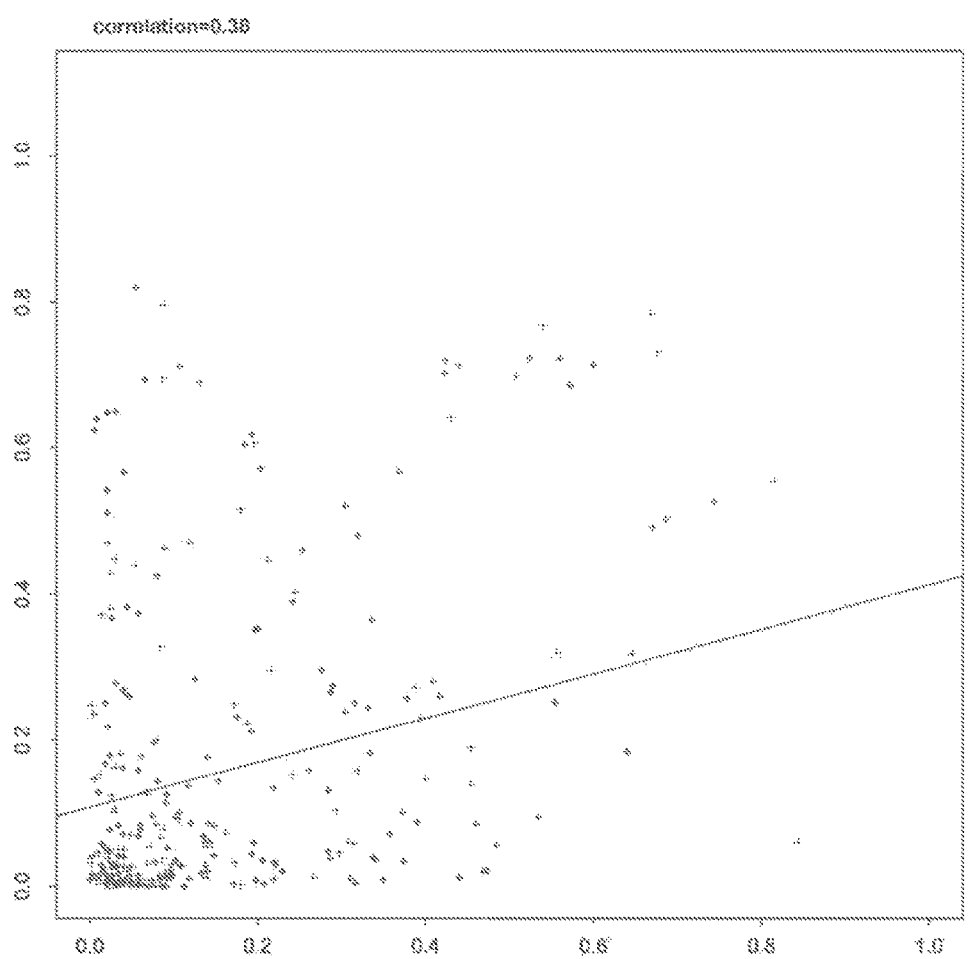
FIG. 4C shows a plot for the TA model for Node-negative patients.
Figure 4D:
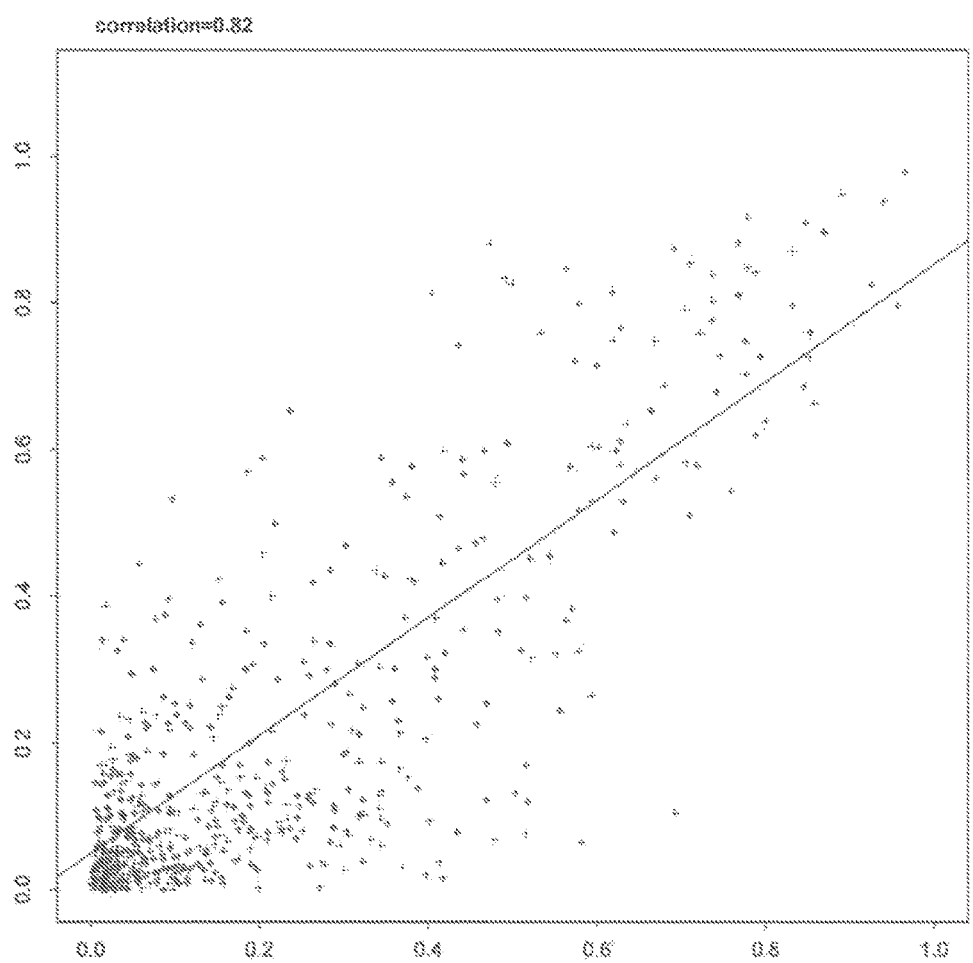
FIG. 4D shows a plot for the TA model for Node-positive patients.
Figure 4E:
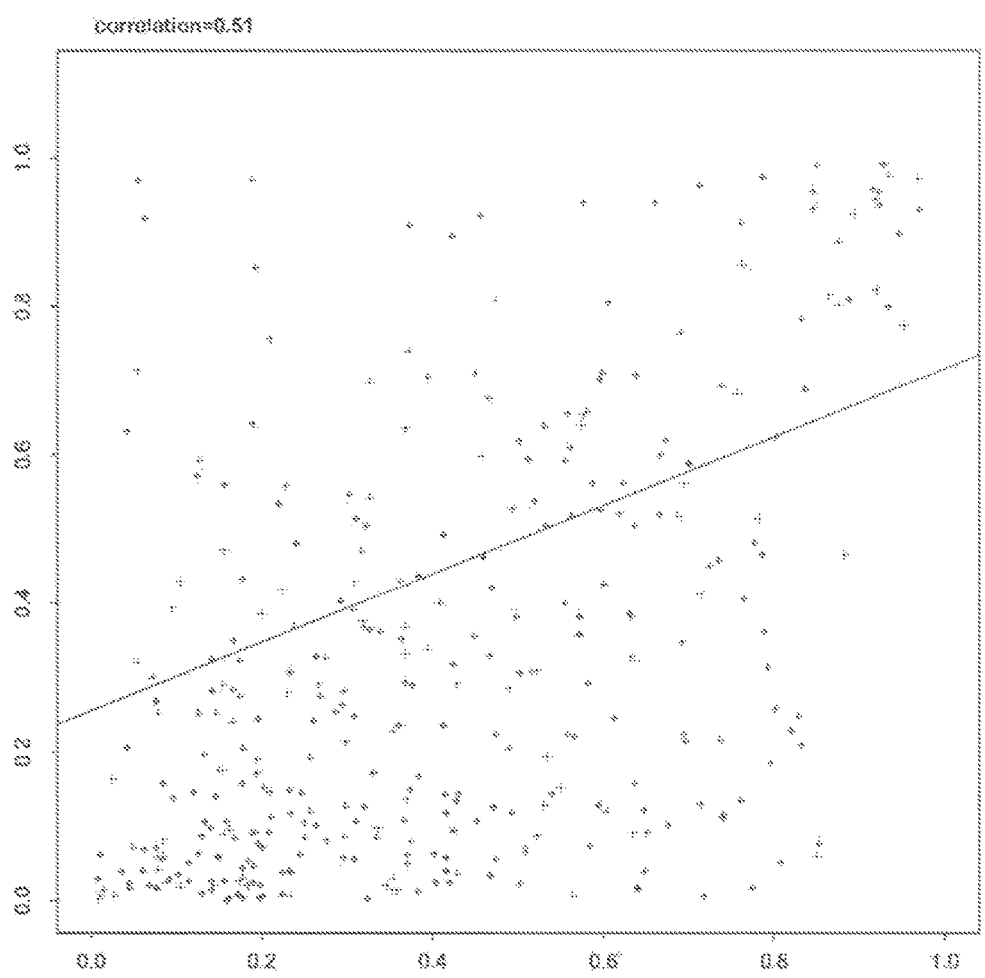
FIG. 4E shows a plot for the TxA model for ER-negative patients.
Figure 4F:
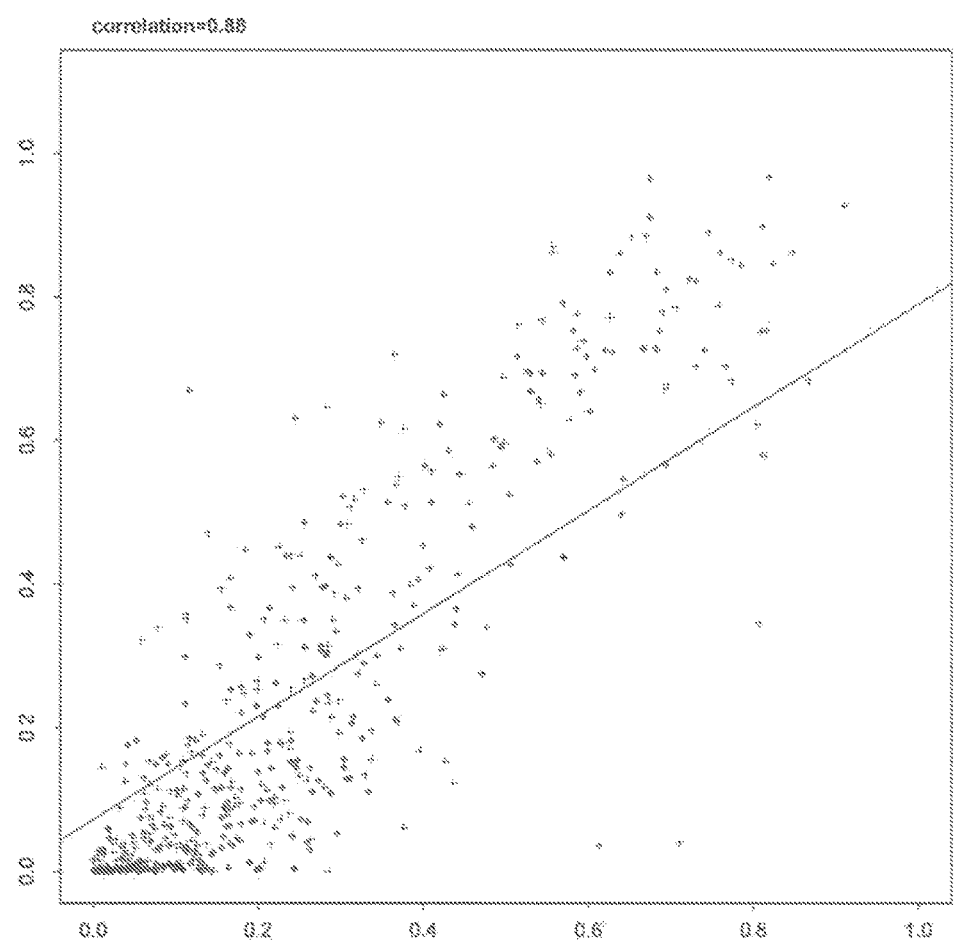
FIG. 4F shows a plot for the TxA model for ER-positive patients.
Figure 4G:
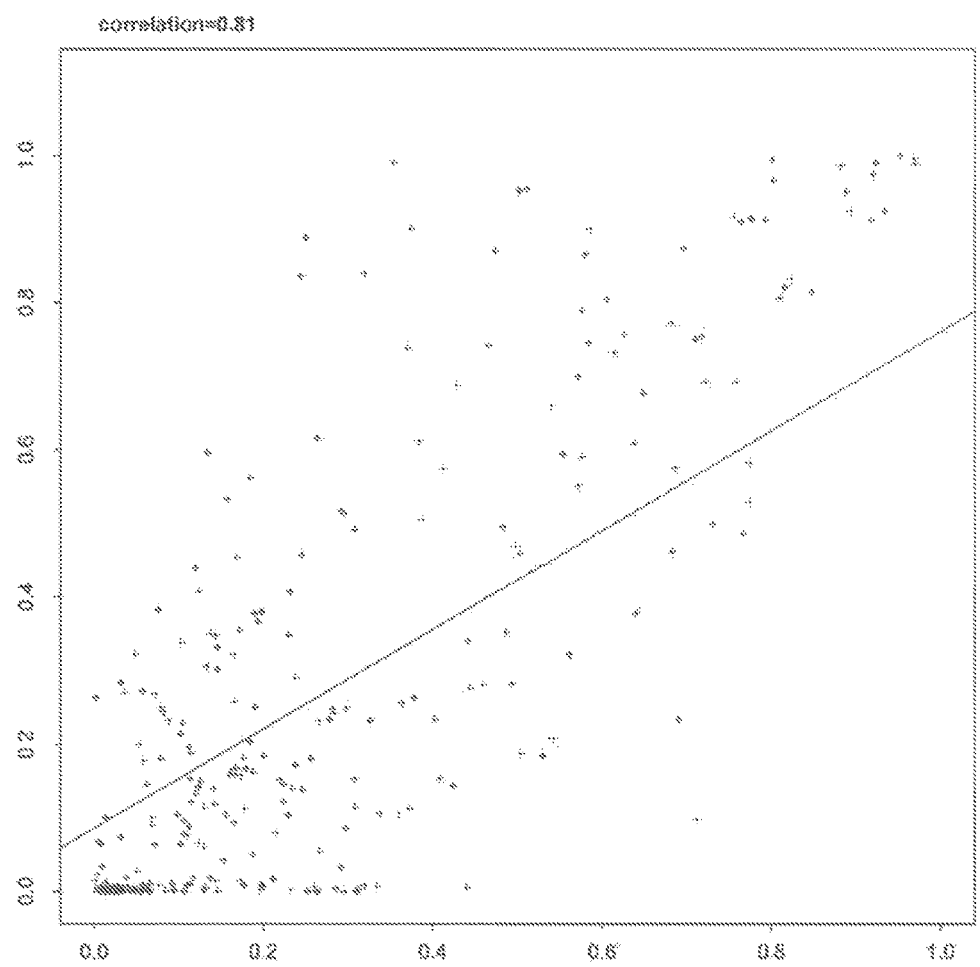
FIG. 4G shows a plot for the TxA model for Node-negative patients.
Figure 4H:
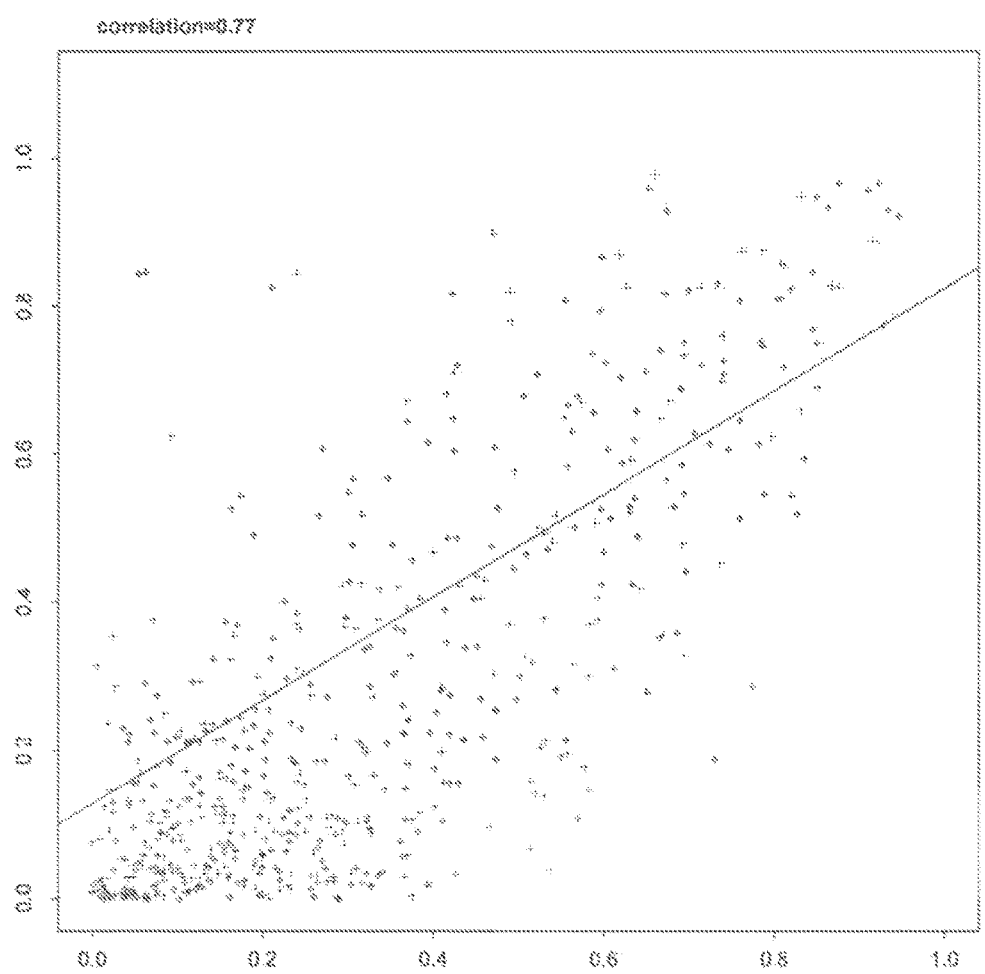
FIG. 4H shows a plot for the TxA model for Node-positive patients.

A Random Sampling Screening (RSS) procedure was then performed on $S_0$ to further narrow down the candidates to a much smaller set. RSS works as follows:
1. Randomly draw a sample of min $\{(S_0/4), 500\}$ probes from $S_0$, denote the sampled set of probes $C_0$;

To select significant probes to a model and evaluate the model, the probes were added one at a time (from highest ranked) to the clinical-variables-only model (which was a random Forest model built with only clinical variables: Age, ER-status, HER2-status, t_stage, and n_stage), then f1-score was recorded along the path. The optimal number of probes for the model was chosen to be the number of probes corresponding to the first local maximum (here, local is defined to be within +/−3 probes) of f1-score. (FIG. 2).

Except models with clinical variables only (clinical models) and clinical variables with genes (clinical-gene models), gene-only models (gene models) were also built for each treatment group by using the genes selected for clinical-gene models. This allows one to show the relative importance of the two types of variables.

Regimen Selection

Once the models were built for the three regimens, each patient had a predicted probability of pCR from the model, whose corresponding regimen was the regimen the patient actually received. To avoid over-fitting, the predicted probabilities were obtained using 10-fold cross-validation, meaning that the response of any patient was predicted using the model built without that patient's information. For each model the predicted probabilities of pCR were sorted and divided into 5 probability intervals (PIs), such that each interval contained roughly equal numbers of patients (with small adjustments to balance the probabilities covered by each interval) (for a concrete example, see Table 5). Precisions (or positive predicted values) were then computed for each interval by taking the ratio of the number of observed pCR in the interval and the total number of patients in the interval. This ratio, called the pCR score, is the estimated probability of having pCR for the particular regimen for a patient whose predicted probability of pCR falls into that particular PI. Each regimen had five pCR scores corresponding to the five PIs. A manual construction of PIs was also used and compared with the construction described above.

Next, the probabilities of being pCR were predicted for all the patients under each model. Again, for the patients used to build a model, their predicted probabilities were obtained from the 10-fold cross-validation. Each patient had three predicted probabilities of being pCR for the three models built using A group, TA group, and TxA group, respectively. Each probability was then mapped to one of the PIs for each model. The regimen whose mapped PI had the highest pCR score was the optimal regimen assigned to the patient. To take toxicities of the regimens into account, if the pCR score for A treatment was within +/−0.02 of the pCR score of the other two regimens, the patient was assigned to A treatment. Alternatively, assignment was also performed with the purpose of achieving the highest pCR score and a slightly higher expected rate of pCR was obtained. The expected number of pCR cases was computed as the sum of pCR scores of all the patients based on the regimens assigned to them.

Stratification of Patient Population

The patient population in the combined dataset was quite heterogeneous. The population was stratified in several ways to investigate how stratification would affect the outcome of the study. 10% of patients were HER2-positive in the study population. Currently, an effective targeted therapy is available for HER2-positive patients using trastuzumab. Most HER2-positive patients will receive the targeted therapy in the current clinical setting. It is worth mentioning that many HER2-positive patients are still given chemotherapy in addition to trastuzumab to increase the effectiveness of targeted therapy.

The study for HER2-negative patients follows the same protocol for the whole population and very similar results were obtained. There were not enough HER2-positive patients to perform this study on. HER2-negative patients were further stratified by their lymph node or ER status, which resulted in two stratifications: (1) node-positive and node-negative, and (2) ER-positive and ER-negative. All the patients in this stratification were HER2-negative. An issue with stratification is that one is left with smaller patient populations, which will inevitably limit one's ability to build quality predictive models. As a result, the further stratifications of HER2-negative patients were studied for patients who received either TA or TxA. The patients who received only anthracyclines (A group) were not included in these studies.

Comparison Between Paclitaxel (T) and Docetaxel (Tx)

Several clinical trials have shown the benefit of addition of taxanes to anthracycline-based regimens (Gajria, et al., 2010). Paclitaxel and docetaxel both belong to the taxane family of anti-cancer compounds, and they share major parts of their structures and mechanisms of action. However, they differ in several aspects including depolymerization inhibition activity and toxicity profiles (Verweij, et al., 1994). Paclitaxel and docetaxel, when administered as single agents, have similar efficacy to anthracyclines in patients naive to chemotherapy (Chan, et al., 1999, Sledge, et al., 2003). Several clinical trials also showed that the improvements in DFS (disease-free survival) and OS (overall survival) were similar for both paclitaxel and docetaxel (De Laurentiis, et al., 2008, Sparano, et al., 2008). In this study population, more patients who received docetaxel have pCR (33.1%) than those receiving paclitaxel (19.7%). Of course, that does not necessarily serve as strong evidence for docetaxel having higher efficacy than paclitaxel. A key question that still remains is: do patients react similarly to both drugs? Are there sub-populations who should receive one drug in preference to the other? As both paclitaxel and docetaxel are commonly used for breast cancer treatment, this is a question with significant clinical implications. Herein, the comparison between paclitaxel and docetaxel was done using a subpopulation of HER2-negative patients by stratifying the subpopulation using either lymph node or ER status, as described in the previous paragraph.

Example 2

Results for the Entire Population

Model Performance and Gene Signatures

The performance of the three types of models for the three types of regimens is shown in Table 3. Models with both clinical and genetic variables (clinical-gene models) generally perform better than models with only clinical variables (clinical models) and models with only genetic variables (gene models). Addition of genetic variables improved the performance for TA and TxA groups dramatically, while the three models did not show significant differences for A group. For TA and TxA groups, both gene models and clinical-gene models performed much better than clinical models, indicating genetic variables can be powerful predictors of chemotherapy responses. Based on this comparison, clinical-gene models were used in the rest of this study. The gene signatures that were responsible for the treatment responses of each regimen are shown in Table 4. The gene signatures consist of 3, 5, and 11 genes for A, TA, and TxA regimens, respectively.

TABLE 3

The Performance of the Three Models: Clinical Variables Only, Clinical-Gene Model with Both Clinical and Genetic Variables, and Gene Model with Genetic Variables Only*

| | Clinical model | | | Clinical-Gene model | | | Gene model | | |
|---|---|---|---|---|---|---|---|---|---|
| Regimens | F1-score | Precision | Recall | F1-score | Precision | Recall | F1-score | Precision | Recall |
| TA | 0.316 | 0.652 | 0.208 | 0.636 | 0.8 | 0.528 | 0.554 | 0.736 | 0.444 |
| TxA | 0.523 | 0.565 | 0.487 | 0.734 | 0.864 | 0.638 | 0.746 | 0.855 | 0.663 |
| A | 0.444 | 0.667 | 0.333 | 0.375 | 0.75 | 0.25 | 0.444 | 0.667 | 0.333 |

*A: anthracyclines only, TA: anthracyclines and paclitaxel, TxA: anthracyclines and docetaxel.

Values in bold are the highest values for each regimen.

TABLE 4

Genes Selected for the Three Regimens

| Probe Set | Symbol | Description | Chromosome | pCR Status* |
|---|---|---|---|---|
| | | Anthracycline (A) regimen | | |
| 218066_at | SLC12A7[42] | solute carrier family 12 (potassium/chloride transporter), member 7 | 5 | + |
| 210164_at | GZMB[43] | granzyme B (granzyme 2, cytotoxic T-lymphocyte- associated serine esterase 1) | 14 | + |
| 213211_s_at | TAF6L | TAF6-like RNA polymerase II, p300/CBP-associated factor (PCAF)- associated factor, 65 kDa | 11 | − |
| | | Paclitaxel and anthracycline (TA) regimen | | |
| 213033_s_at | NFIB | nuclear factor I/B | 9 | + |
| 219051_x_at | METRN | meteorin, glial cell differentiation regulator | 16 | − |
| 220425_x_at | ROPN1B | rhophilin associated tail protein 1B | 3 | + |
| 209289_at | NFIB | nuclear factor I/B | 9 | + |
| 204822_at | TTK | TTK protein kinase | 6 | + |
| 213032_at | NFIB | nuclear factor I/B | 9 | + |
| 208712_at | CCND1 | cyclin D1 | 11 | − |
| | | Docetaxel and anthracycline (TxA) regimen | | |
| 203554_x_at | PTTG1 | pituitary tumor-transforming 1 | 5 | + |
| 200853_at | H2AFZ | H2A histone family, member Z | 4 | + |
| 209076_s_at | WDR45L | WD repeating-containing protein 45- like | 17 | + |
| 200934_at | DEK | DEK oncogene | 6 | + |
| 213911_s_at | H2AFZ | H2A histone family, member Z | 4 | + |
| 202107_s_at | MCM2 | minichromosome maintenance complex component 2 | 3 | + |
| 202412_s_at | USP1 | ubiquitin specific peptidase 1 | 1 | + |
| 209832_s_at | CDT1 | chromatin licensing and DNA replication factor 1 | 16 | + |
| 212282_at | TMEM97 | transmembrane protein 97 | 17 | + |
| 213296_at | RER1 | RER1 retention in endoplasmic reticulum 1 homolog (*S. cerevisiae*) | 1 | − |
| 201930_at | MCM6 | minichromosome maintenance complex component 6 | 2 | + |
| 218437_s_at | LZTFL1 | leucine zipper transcription factor-like 1 | 3 | − |

*PCR status: "+": gene expression level higher in pCR cases; "−": gene expression level lower in pCR cases.

Personalized Regimen Selection

As mentioned in the Materials and Methods section, the predicted probabilities of each model were first sorted and then divided into 5 equally numerous intervals (Table 5). The probabilities covered by the intervals were skewed due to the fact that pCR rate of each regimen was lower than RD rate. This division allowed patients to be distributed evenly in each interval so that the estimated rate of pCR (pCR score) was reliable for most of the intervals. Table 6 shows that the models performed quite well when the predicted probability of pCR was very low. The first intervals in all three treatment groups had negative predictive value (NPV) of 97% or higher. Models for TA and TxA also performed well on the other end of the spectrum—when the predicted probabilities of pCR were high. In such cases, positive predictive values (PPVs) were also quite high, with 0.667 for TA and 0.878 for TxA group.

TABLE 5

Probability Intervals and pCR Scores for Three Treatment Groups

Anthracycline (A)

| | | | | | |
|---|---|---|---|---|---|
| Intervals | [0, 0.0052) | [0.0052, 0.016) | [0.016, 0.038) | [0.038, 0.115) | [0.115, 1] |
| # of patients | 28 | 25 | 29 | 29 | 28 |
| pCR score | 0 | 0.04 | 0.069 | 0.103 | 0.214 |
| 95% CI | (0, 0) | (−0.03, 0.113) | (−0.025, 0.163) | (−0.010, 0.217) | (0.062, 0.367) |
| # of patients assigned | 0 | 40 | 61 | 38 | 85 |

Paclitaxel and Anthracycline (TA)

| | | | | | |
|---|---|---|---|---|---|
| Intervals | [0, 0.024] | [0.024, 0.07] | [0.07, 0.17] | [0.17, 0.364] | [0.364, 1] |
| # of patients | 135 | 155 | 146 | 147 | 147 |
| pCR score | 0.015 | 0.045 | 0.082 | 0.170 | 0.667 |
| 95% CI | (−0.005, 0.034) | (0.01, 0.0789) | (0.038, 0.127) | (0.109, 0.231) | (0.59, 0.743) |
| # of patients assigned | 0 | 16 | 21 | 62 | 159 |

Docetaxel and Anthracycline (TxA)

| | | | | | |
|---|---|---|---|---|---|
| Intervals | [0, 0.0628] | [0.0628, 0.1676] | [0.1676, 0.3052] | [0.3052, 0.6024] | [0.6024, 1] |
| # of patients | 49 | 48 | 48 | 48 | 49 |
| pCR score | 0.020 | 0.083 | 0.229 | 0.438 | 0.878 |
| 95% CI | (−0.02, 0.06) | (0.005, 0.161) | (0.11, 0.348) | (0.298, 0.577) | (0.785, 0.97) |
| # of patients assigned | 16 | 78 | 140 | 220 | 175 |

Patients were then assigned to the optimal regimen using the method described in the Materials and Methods section. The expected number of pCR achieved using the predictive models and the personalized regimen selection approach (PERS) was 435.8 (Table 6, the first row), which was an 84% improvement compared to the observed number of pCR (236) based on the original assignments.

The results for different stratifications are also shown in Table 6. For the HER2-negative population, very similar results to those from the whole population were obtained, which is likely due to the fact that 90% of patients in the whole study population were 90% HER2-negative. The gene signatures obtained also shared a significant number of genes. Overall, expected rate of pCR can be substantially improved compared to those observed based on the original regimen assignments.

TABLE 6

Expected Number of pCR and Number of Patients Assigned to Each Regimen for the Study Using the Whole Population and Different Stratifications*

| | | Treatments | | | | | | | |
|---|---|---|---|---|---|---|---|---|---|
| Study population | Assignment strategy | Model performance for A[a] | # patients assigned to A[b] | Model performance for TA | # patients assigned to TA | Model performance for TxA | # patients assigned to TxA | # of pCR[c] | Rate of pCR (%) |
| All patients (1111) | Original | — | 139 | — | 730 | — | 242 | 236 | 21.2 |
| | PERS[d] | 0.375 (0.75) | 224 | 0.636 (0.8) | 258 | 0.734 (0.864) | 629 | 435.8 | 39.2 |
| HER2− (997) | Original | — | 130 | — | 661 | — | 206 | 191 | 19.2 |
| | PERS | 0.5 (1.0) | 242 | 0.611 (0.766) | 257 | 0.876 (0.914) | 498 | 339.3 | 34.0 |
| HER2− & ER− (349) | Original | — | — | — | 251 | — | 98 | 125 | 35.8 |
| | PERS | — | — | 0.731 (0.792) | 236 | 0.875 (0.897) | 113 | 160.3 | 45.9 |
| HER2− & ER+ (518) | Original | — | — | — | 410 | — | 108 | 54 | 10.4 |
| | PERS | — | — | 0.182 (0.333) | 282 | 0.857 (0.9) | 236 | 135.0 | 26.1 |
| HER2− & Node− (276) | Original | — | — | — | 200 | — | 76 | 51 | 18.5 |
| | PERS | — | — | 0.455 (0.667) | 142 | 0.933 (0.913) | 134 | 101.0 | 36.6 |

TABLE 6-continued

Expected Number of pCR and Number of Patients Assigned to Each Regimen for the Study
Using the Whole Population and Different Stratifications*

| Study population | Assignment strategy | Model performance for A[a] | # patients assigned to A[b] | Model performance for TA | # patients assigned to TA | Model performance for TxA | # patients assigned to TxA | # of pCR[c] | Rate of pCR (%) |
|---|---|---|---|---|---|---|---|---|---|
| HER2− & Node+ (591) | Original | — | — | — | 461 | — | 130 | 128 | 21.7 |
|  | PERS | — | — | 0.575 (0.667) | 280 | 0.85 (0.872) | 311 | 191.1 | 32.3 |

*HER2−: HER2-negative, ER−: ER-negative, ER+: ER-positive, Node−: node-negative, Node+: node-positive. The numbers in parenthesis in the first column are the number of patients in the corresponding study populations. A: anthracyclines regimen, TA: paclitaxel and anthracyclines regimen, TxA: docetaxel and anthracyclines regimen.
[a]F1-scores (precision or positive predicted value for patients with predicted probability >0.5) for clinical-gene-models.
[b]number of patients originally assigned to the regimen or assigned using PERS.
[c]Number of pCR cases observed in the original population or estimated number of pCR cases using PERS.
[d]Both pCR score and toxicity, if applicable, are used in regimen selection. Using pCR score only gives slightly higher rate of pCR.

Proportion of Patients Who May Benefit from Personalized Regimen Selection

The portion of patients who may benefit from personalized regimen selection given the currently available regimens was also examined. For each patient, the maximum absolute difference of pCR scores (MADPS) between any two regimens was first calculated. Each patient had three pCR scores corresponding to the three models (regimens), which gave three pairwise differences. The absolute value of the largest among the three is the MADPS for a patient. The magnitude of MADPS indicated how important personalized regimen selection was for the patient. A value close to zero meant the patient reacted to all the regimens similarly. A large value meant the patient reacted very differently for at least two regimens. FIGS. 3A-F show the cumulative distribution for MADPS for all the patients for all the studies with different stratifications. Overall, a substantial number of patients can benefit from personalized regimen selection. From FIG. 3A, there are around 40% of patients that have MADPS of 0.4. This observation is also consistent among different stratifications (around 20% of patients have MADPS of 0.5 for all stratifications).

Conclusions and Discussion

In this study, high-throughput gene expression data from a large number of breast cancer patients who received several types of neoadjuvant chemotherapy regimens was used to investigate whether personalized regimen selection can benefit breast cancer patients currently receiving these therapies. Patients were divided into three regimen groups: those who received only anthracycline drugs (A group), those who received both anthracycline drugs and paclitaxel (TA group), and those who received both anthracyline drugs and docetaxel (TxA group). A substantial number of patients responded differently to at least two regimens, indicating personalized regimen selection can be very beneficial for patients who choose one of these options. Also, the variable selection method can select a small number of genes that can effectively differentiate the patients who will have higher probability of pCR under certain regimens. A personalized regimen selection (PERS) strategy was designed and applied retrospectively to the patients in the data set. The pCR rate can be potentially improved from 21.2% to 39.3%, an 84% increase. 17.28% of patients were likely overtreated, meaning they received TA or TxA regimen, but if they had received A regimen they would have had at least the same probability of pCR. 9.63% of patients were undertreated, meaning that they received A regimen, but if they had received TA or TxA, they would have a better probability of pCR. Considering that the undertreated situations may be due to affordability issues, the current strategies in regimen selection tend to overtreat patients.

In addition to helping patients to choose the optimal regimen, in cases that no regimen gives a high probability of pCR, patients can also choose not to take these regimens or participate in alternative treatments such as clinical trials. PERS assigned 111 patients to the second and third probability intervals of A regimen; 37 patients to the second and third probability intervals of TA regimen; and 94 patients to the first two probability intervals of TxA regimen (Table 5). The negative predicted values (NPVs) were higher than 90% for all these intervals. This indicated that 21.8% of patients were likely be predicted to have a low chance of pCR and their actual chances were indeed low. Although it is still a personal decision on whether one of these chemotherapies should be received, providing such information can guide patients in their decision making. On the other hand, 175 (15.8%) patients were assigned to the fifth interval in TxA regimen with a positive predicted value (PPV) of 0.878. An additional 159 (14.3%) patients were assigned to the fifth interval in TA regimen with a high PPV of 0.667. Taken together, these predictions can be very useful in decision making for more than half of patients (and can still be useful for the rest of patients since they will also know their probability of pCR).

Comparison of the significant genes identified in this study (Table 4) with those found in a previous study (Hatzis, et al., 2011) showed no overlap between the two sets of genes. The dataset used in Hatzis, et al., 2011, consisting of 470 patients, is a subset of the current study population. Given the significant overlap between the two datasets, it is somewhat surprising to see that no single gene was found by both studies. The genes identified by the models built in different stratifications in our study were further examined. To our surprise, except the HER2-negative subpopulation, which shared 90% of the patients with the whole population, most of the models produced quite different sets of genes with only a rather small number of genes in common. The consistency among the predicted probabilities of pCR by different models was thus studied. FIGS. 4A-H shows the scatter plots for predicted probabilities of pCR between different models. Although the models picked different sets of genes, the predicted probabilities for pCR were highly correlated between most of the model pairs, except for those models with poor quality. It is understandable for poor quality models to show less correlation with other models. While the complex regulatory relationships among the genes may play a role here, the profound reasons for this phenomenon will be the subject of future studies.

One may notice that in the assignment for the whole study population, TxA was assigned to the most patients. This made sense because the pCR rate of TxA regimen was 33%, while it was only 8.6% for A and 19.7% for TA regimen. The model built for TxA regimen also had higher precision, which contributed to this outcome. In this study, the model performance of the A treatment was worse than the other two models. This was likely caused by the fact that both the total number of patients and the number of pCR cases in A group were much lower compared to the other two groups.

The patients in this dataset were quite heterogeneous even after removing all the HER2+patients. Combining patients with different characteristics may help to find markers common to all of them. Further stratifications will allow the study of whether consistent results will be obtained when studying different subpopulations separately. However, due to a limited number of patients in certain strata, a thorough comparison was not performed in this study. Stratification of HER2-negative patients, who have received TA or TxA regimen, by their node or ER status, has produced qualitatively similar results.

The intervals in Table 5 were highly skewed. For example, the fifth interval for A treatment covered the whole range of probabilities from 0.115 to 1, which does not seem very practical. A manual approach to make the probabilities covered by each interval less skewed while at the same time keeping enough patients in each interval to make the estimated pCR scores reliable was used to investigate how division of intervals affects the expected pCR. The intervals are shown in Table 7. The patients were re-assigned based on these intervals and the results are shown in Table 8. The expected number of pCR was only slightly higher than that achieved using intervals based on quintiles.

TABLE 7

Heuristically Broken Intervals and pCR Scores

Anthracycline (A)

| Intervals | [0, 0.02) | [0.02, 0.25) | [0.25, 1] | | |
|---|---|---|---|---|---|
| # of patients | 64 | 62 | 13 | | |
| pCR proportion | 0.031 | 0.081 | 0.385 | | |
| 95% CI | (−0.005, 0.067) | (0.024, 0.138) | (0.163, 0.607) | | |

Paclitaxel and Anthracycline (TA)

| Intervals | [0, 0.1) | [0.1, 0.2) | [0.2, 0.35) | [0.35, 0.5) | [0.5, 1] |
|---|---|---|---|---|---|
| # of patients | 349 | 118 | 109 | 64 | 90 |
| pCR proportion | 0.029 | 0.153 | 0.156 | 0.391 | 0.822 |
| 95% CI | (0.014, 0.043) | (0.098, 0.207) | (0.099, 0.213) | (0.290, 0.491) | (0.756, 0.889) |

Docetaxel and Anthracycline (TxA)

| Intervals | [0, 0.0628) | [0.0628, 0.1676) | [0.1676, 0.3052) | [0.3052, 0.6024) | [0.6024, 1] |
|---|---|---|---|---|---|
| # of patients | 49 | 48 | 48 | 48 | 49 |
| pCR proportion | 0.020 | 0.083 | 0.229 | 0.438 | 0.878 |

TABLE 7-continued

Heuristically Broken Intervals and pCR Scores

| 95% CI | (−0.013, 0.054) | (0.018, 0.149) | (0.129, 0.329) | (0.320, 0.555) | (0.801, 0.955) |
|---|---|---|---|---|---|

TABLE 8

Number of Patients Assigned to Each Treatment (for re-divided intervals)

| | Anthracycline (A) | Paclitaxel and Anthracycline (TA) | Docetaxel and Anthracycline (TxA) | # of pCR* |
|---|---|---|---|---|
| Original | 139 | 730 | 242 | 236 |
| Assignment based on pCR score only | 187 | 231 | 693 | 437.1829 |
| Assignment based on both pCR score and toxicity | 224 | 225 | 662 | 436.5223 |

*The original group is observed.

10-fold cross validation was used in this study. Most previous studies used separate training and testing data sets. In principle, 10-fold cross validation is less likely to over-fit compared to two separate training and testing data sets. Also, a relatively smaller number of significant genes were found in this study compared to previous studies, indicating that the current models will likely have higher generalizability than those from previous studies.

The approach used in this study can be readily applied to developing personalized regimen selection for other types of cancers, which will be the subject of future studies.

Example 3

Results for the HER2-Negative Subpopulation

The performance of the three types of models for the three types of regimens is shown in Table 9. The predicted probabilities of each model were first sorted and then divided into 5 equally numerous intervals (Table 10). A manual approach to make the probabilities covered by each interval less skewed while at the same time keeping enough patients in each interval to make the estimated pCR scores reliable was used to investigate how division of intervals affects the expected pCR. The intervals are shown in Table 11. The patients were assigned based on these intervals and the results are shown in Table 12. The expected number of pCR was only slightly higher than that achieved using intervals based on quintiles.

TABLE 9

Model Performance for the HER2-negative Subpopulation

| Group (# of probes) | Clinical variables | | | Genes and clinical variables | | | Genes | | |
|---|---|---|---|---|---|---|---|---|---|
| | f1-score | Precision | recall | f1-score | Precision | recall | f1-score | Precision | recall |
| Anthracycline (6) | 0.556 | 0.833 | 0.417 | 0.5 | 1 | 0.333 | 0.4 | 1 | 0.25 |
| Paclitaxel and Anthracycline (TA) (9) | 0.231 | 0.45 | 0.155 | 0.611 | 0.766 | 0.509 | 0.574 | 0.709 | 0.483 |
| Docetaxel and Anthracycline (TxA) (19) | 0.475 | 0.509 | 0.444 | 0.876 | 0.914 | 0.841 | 0.867 | 0.912 | 0.825 |

TABLE 10

Intervals and pCR Scores for the HER2-negative Subpopulation (broken by quintiles)

| Anthracycline (A) | | | | | |
|---|---|---|---|---|---|
| Interval | (0, 0.002) | (0.002, 0.014) | (0.014, 0.0468) | (0.0468, 0.2216) | (0.2216, 1) |
| Counts | 21 | 28 | 29 | 26 | 26 |
| PCR score | 0.048 | 0.071 | 0.034 | 0.077 | 0.231 |
| 95% CI | (0, 0.139) | (0, 0.167) | (0, 0.1) | (0, 0.179) | (0.069, 0.393) |
| Paclitaxel and Anthracycline (TA) | | | | | |
| Interval | (0, 0.028) | (0.028, 0.06) | (0.06, 0.138) | (0.138, 0.318) | (0.318, 1) |
| Counts | 123 | 138 | 134 | 133 | 133 |
| PCR score | 0.033 | 0.022 | 0.075 | 0.165 | 0.579 |
| 95% CI | (0.001, 0.064) | (0, 0.046) | (0.03, 0.119) | (0.102, 0.229) | (0.495, 0.663) |
| Docetaxel and Anthracycline (TxA) | | | | | |
| Interval | (0, 0.034) | (0.034, 0.126) | (0.126, 0.266) | (0.266, 0.638) | (0.638, 1) |
| Counts | 41 | 41 | 41 | 40 | 43 |
| PCR score | 0 | 0.098 | 0.049 | 0.4 | 0.95 |
| 95% CI | — | (0.007, 0.188) | (0, 0.115) | (0.248, 0.552) | (0.891, 1) |

TABLE 11

Heuristically Broken Intervals and pCR Scores for the HER2-negative Subpopulation

| Anthracycline (A) | | | | | | |
|---|---|---|---|---|---|---|
| Interval | (0, 0.02) | (0.02, 0.25) | (0.25, 1) | | | |
| Counts | 63 | 48 | 19 | | | |
| PCR score | 0.063 | 0.042 | 0.316 | | | |
| 95% CI | (0.003, 0.124) | (0, 0.098) | (0.107, 0.525) | | | |
| Paclitaxel and Anthracycline (TA) | | | | | | |
| Interval | (0, 0.025) | (0.025, 0.05) | (0.05, 0.1) | (0.1, 0.2) | (0.2, 0.4) | (0.4, 1) |
| Counts | 116 | 107 | 134 | 101 | 103 | 100 |
| PCR score | 0.034 | 0.009 | 0.067 | 0.099 | 0.252 | 0.660 |
| 95% CI | (0.001, 0.068) | (0, 0.028) | (0.025, 0.110) | (0.041, 0.157) | (0.169, 0.336) | (0.567, 0.753) |
| Docetaxel and Anthracycline (TxA) | | | | | | |
| Interval | (0, 0.034) | (0.034, 0.126) | (0.126, 0.266) | (0.266, 0.638) | (0.638, 1) | |
| Counts | 41 | 41 | 41 | 40 | 43 | |
| PCR score | 0 | 0.098 | 0.049 | 0.4 | 0.95 | |
| 95% CI | — | (0.007, 0.188) | (0, 0.115) | (0.248, 0.552) | (0.891, 1) | |

TABLE 12

Number of Patients Assigned to Each Treatment

| Treatment | Paclitaxel and Anthra-cycline (TA) | Docetaxel and Anthra-cycline (TxA) | Anthra-cycline (A) | # of pCR* |
|---|---|---|---|---|
| Original | 661 | 206 | 130 | 191 |
| Assignment based on pCR score only | 296 | 551 | 150 | 344.41 |
| Assignment based on both pCR score and toxicity | 254 | 513 | 230 | 343.98 |

*The original group is observed.

Example 4

Results for the ER-Positive Subpopulation

The performance of the three types of models for the three types of regimens is shown in Table 13. The predicted probabilities of each model were first sorted and then divided into 5 equally numerous intervals (Table 14). In Table 14 the first intervals of both models cover less than 1% of the range while the last interval covers over 60% of the range; therefore, the intervals of TA were further broken into 6 intervals instead of 5, and the new intervals are shown in Table 15. The NPV of both models for the lower predicted probability range were pretty good (over 90% for both model); however, the PPV of TA model in the higher predicted probability range is a little low (33.3%) which again could be caused by the low observed pCR rate. The assignment shows that the expected number of pCR could be increased by over 100% (Table 16). It also suggests that at least a quarter of the patients that were assigned to TA should be assigned to TxA. It is hard to tell if there is a significant preference between paclitaxel and docetaxel, as the assigned number of patients are quite close for both drugs. It is clear that the original assignment, where more patients were sorted to paclitaxel, yields a lower number of pCR.

TABLE 13

Model Performance for ER-positive Subpopulation

| Group (# of probes) | Clinical variables | | | Gene and clinical variables | | | Genes | | |
|---|---|---|---|---|---|---|---|---|---|
| | f1-score | Precision | recall | f1-score | Precision | recall | f1-score | Precision | recall |
| Paclitaxel and Anthracycline (TA) (6) | 0 | 0 | 0 | 0.182 | 0.333 | 0.125 | 0.174 | 0.286 | 0.125 |
| Docetaxel and Anthracycline (TxA) (12) | 0.222 | 0.6 | 0.136 | 0.857 | 0.9 | 0.818 | 0.837 | 0.857 | 0.818 |

TABLE 14

Intervals and pCR Scores for the ER-positive Subpopulation (broken by quintiles)

| Paclitaxel and Anthracycline (TA) | | | | | |
|---|---|---|---|---|---|
| Interval | (0, 0.006) | (0.006, 0.017) | (0.017, 0.034) | (0.034, 0.104) | (0.104, 1) |
| Counts | 79 | 85 | 79 | 84 | 83 |
| PCR score | 0.025 | 0.059 | 0.089 | 0.071 | 0.145 |
| 95% CI | (0, 0.060) | (0.009, 0.109) | (0.026, 0.151) | (0.016, 0.127) | (0.069, 0.220) |
| Docetaxel and Anthracycline (TxA) | | | | | |
| Interval | (0, 0.002) | (0.002, 0.026) | (0.026, 0.090) | (0.090, 0.395) | (0.395, 1) |
| Counts | 20 | 22 | 23 | 21 | 22 |
| PCR score | 0 | 0 | 0.130 | 0.048 | 0.818 |
| 95% CI | — | — | (0, 0.268) | (0, 0.139) | (0.657, 0.979) |

TABLE 15

Heuristically Broken Intervals and pCR Scores for the ER-positive Subpopulation

| Paclitaxel and Anthracycline (TA) | | | | | | |
|---|---|---|---|---|---|---|
| Interval | (0, 0.01) | (0.01, 0.04) | (0.04, 0.1) | (0.1, 0.3) | (0.3, 0.5) | (0.5, 1) |
| Counts | 109 | 150 | 66 | 51 | 22 | 12 |
| PCR score | 0.046 | 0.06 | 0.091 | 0.137 | 0.045 | 0.333 |

TABLE 15-continued

Heuristically Broken Intervals and pCR Scores for the ER-positive Subpopulation

| 95% CI | (0.007, 0.085) | (0.022, 0.098) | (0.022, 0.160) | (0.043, 0.232) | (0, 0.132) | (0.067, 0.6) |
|---|---|---|---|---|---|---|
| | | | Docetaxel and Anthracycline (TxA) | | | |
| Interval | (0, 0.002) | (0.002, 0.026) | (0.026, 0.090) | (0.090, 0.395) | (0.395, 1) | |
| Counts | 20 | 22 | 23 | 21 | 22 | |
| PCR score | 0 | 0 | 0.130 | 0.048 | 0.818 | |
| 95% CI | — | — | (0, 0.268) | (0, 0.139) | (0.657, 0.979) | |

TABLE 16

Number of Patients Assigned to Each Treatment

| Treatment | Paclitaxel and Anthracycline (TA) | Docetaxel and Anthracycline (TxA) | # of pCR* |
|---|---|---|---|
| Original | 410 | 108 | 54 |
| Assigned based on pCR score | 267 | 251 | 135.42 |

*The original group is observed.

Example 5

Results for the ER-Negative Subpopulation

Table 17 shows the performance of the models, and both of the models perform well. The PPV is 0.824 for the patients of TA and 0.895, 0.9 for those patients of TxA with high predicted probability, while the NPV is around 0.9 for lower predicted probability. The quintile intervals look evenly spaced in this subpopulation (Table 18) and the assignment suggests that although TxA is not preferred over TA, some patients still can benefit from switching from TA to TxA. Compared to the original assignment, at least 15 patients could potentially have better effects from treating with TxA, and the higher expected number of pCR (160.31>125, about 30% increasing) confirmed that personalized assignment improves the chance of a patient to have pCR. However, in this subpopulation paclitaxel is preferred over docetaxel since more patients are predicted to have a better chance of achieving pCR when assigned to TA.

TABLE 18

Intervals and pCR Scores for the ER-negative Subpopulation (broken by quintiles)

| | Paclitaxel and Anthracycline (TA) | | | | |
|---|---|---|---|---|---|
| Interval | (0, 0.084) | (0.084, 0.182) | (0.182, 0.358) | (0.358, 0.612) | (0.612, 1) |
| Counts | 49 | 51 | 50 | 50 | 51 |
| PCR score | 0.102 | 0.118 | 0.16 | 0.46 | 0.824 |
| 95% CI | (0.017, 0.187) | (0.029, 0.206) | (0.058, 0.262) | (0.322, 0.598) | (0.719, 0.928) |
| | Docetaxel and Anthracycline (TxA) | | | | |
| Interval | (0, 0.063) | (0.063, 0.276) | (0.276, 0.494) | (0.494, 0.86) | (0.86, 1) |
| Counts | 20 | 19 | 20 | 19 | 20 |
| PCR score | 0.1 | 0.053 | 0.15 | 0.895 | 0.9 |
| 95% CI | (0, 0.231) | (0, 0.153) | (0, 0.306) | (0.757, 1) | (0.769, 1) |

Example 6

Results for the Lymph Node-Positive Subpopulation

Both models perform fairly well (Table 19), and the NPVs of the lower predicted probability range are over 90% while the PPVs of the higher predicted probability range are as high as 92%. The intervals were re-broken for TA since the last interval of TA covers over 65% of the range and more than 90 patients fell into this range (Table 20). The new intervals and their corresponding pCR scores are shown in Table 21. The assignment (Table 22) shows that docetaxel in this population is preferred over paclitaxel, and the expected number of pCR increases by roughly 50% by personalized assignment treatment.

TABLE 17

Model Performance for the ER-negative Subpopulation

| Group (# of probes) | Clinical variables | | | Gene and clinical variables | | | Genes | | |
|---|---|---|---|---|---|---|---|---|---|
| | f1-score | Precision | recall | f1-score | Precision | recall | f1-score | Precision | recall |
| Paclitaxel and Anthracycline (TA) (14) | 0.286 | 0.429 | 0.214 | 0.731 | 0.792 | 0.679 | 0.714 | 0.786 | 0.655 |
| Docetaxel and Anthracycline (TxA) (2) | 0.607 | 0.562 | 0.659 | 0.875 | 0.897 | 0.854 | 0.723 | 0.714 | 0.732 |

TABLE 19

Model Performance for the Lymph Node-positive Subpopulation

| Group (# of probes) | Clinical variables | | | Gene and clinical variables | | | Genes | | |
|---|---|---|---|---|---|---|---|---|---|
| | f1-score | Precision | recall | f1-score | Precision | recall | f1-score | Precision | recall |
| Paclitaxel and Anthracycline (TA) (3) | 0.295 | 0.452 | 0.218 | 0.575 | 0.667 | 0.506 | 0.523 | 0.606 | 0.460 |
| Docetaxel and Anthracycline (TxA) (7) | 0.525 | 0.538 | 0.512 | 0.85 | 0.872 | 0.829 | 0.810 | 0.842 | 0.780 |

TABLE 20

Intervals and pCR Scores for the Lymph Node-positive Subpopulation

Paclitaxel and Anthracycline (TA)

| Interval | (0, 0.026) | (0.026, 0.062) | (0.062, 0.122) | (0.122, 0.324) | (0.324, 1) |
|---|---|---|---|---|---|
| Counts | 92 | 92 | 91 | 93 | 93 |
| PCR score | 0.033 | 0.022 | 0.044 | 0.237 | 0.602 |
| 95% CI | (0, 0.069) | (0, 0.052) | (0.002, 0.086) | (0.15, 0.323) | (0.503, 0.702) |

Docetaxel and Anthracycline (TxA)

| Interval | (0, 0.032) | (0.032, 0.116) | (0.116, 0.317) | (0.317, 0.722) | (0.722, 1) |
|---|---|---|---|---|---|
| Counts | 26 | 25 | 27 | 26 | 26 |
| PCR score | 0.038 | 0.04 | 0.037 | 0.538 | 0.923 |
| 95% CI | (0, 0.112) | (0, 0.117) | (0, 0.108) | (0.347, 0.73) | (0.821, 1) |

TABLE 21

Heuristically Broken Intervals and pCR Scores for the Lymph Node-positive Subpopulation Paclitaxel and Anthracycline (TA)

| Interval | (0, 0.04) | (0.04, 0.1) | (0.1, 0.3) | (0.3, 0.5) | (0.5, 1) |
|---|---|---|---|---|---|
| Counts | 138 | 105 | 115 | 37 | 66 |
| PCR score | 0.036 | 0.019 | 0.174 | 0.432 | 0.667 |
| 95% CI | (0.005, 0.067) | (0, 0.045) | (0.105, 0.243) | (0.273, 0.592) | (0.553, 0.780) |

Docetaxel and Anthracycline (TxA)

| Interval | (0, 0.032) | (0.032, 0.116) | (0.116, 0.317) | (0.317, 0.722) | (0.722, 1) |
|---|---|---|---|---|---|
| Counts | 26 | 25 | 27 | 26 | 26 |
| PCR score | 0.038 | 0.04 | 0.037 | 0.538 | 0.923 |
| 95% CI | (0, 0.112) | (0, 0.117) | (0, 0.108) | (0.347, 0.73) | (0.821, 1) |

TABLE 22

Number of Patients Assigned to Each Treatment

| Treatment | Paclitaxel and Anthracycline (TA) | Docetaxel and Anthracycline (TxA) | # of pCR* |
|---|---|---|---|
| Original | 461 | 130 | 128 |
| Assigned based on pCR score | 213 | 378 | 190.64 |

*The original group is observed.

Example 7

Results for the Lymph Node-Negative Subpopulation

Table 23 shows the overall performance of the models, and Tables 24 and 25 show that the predicted NPV of both models are high in the lower predicted probability range and the PPV of TxA is high in the higher predicted probability range. However, the last interval of TA covers a relatively long range, and the first three intervals of TxA are not necessarily separated. The new intervals and pCR scores are shown in Table 26. There is still a really high NPV in the lower predicted probability range, while both models have a high PPV in the higher predicted probability range. The assignment (Table 27) suggests that paclitaxel is slightly preferred in this subpopulation, but the expected number of pCR could be improved by switching at least 36 patients from paclitaxel to docetaxel. The switching increases the expected number of patients by about 85%.

TABLE 23

Model Performance for the Lymph Node-negative Subpopulation

| Group (# of probes) | Clinical variables | | | Gene and clinical variables | | | Genes | | |
|---|---|---|---|---|---|---|---|---|---|
| | f1-score | Precision | recall | f1-score | Precision | recall | f1-score | Precision | recall |
| Paclitaxel and Anthracycline (TA) (4) | 0 | 0 | 0 | 0.455 | 0.667 | 0.345 | 0.367 | 0.450 | 0.310 |
| Docetaxel and Anthracycline (TxA) (6) | 0.341 | 0.368 | 0.318 | 0.933 | 0.913 | 0.955 | 0.909 | 0.909 | 0.909 |

TABLE 24

Intervals and pCR Scores for the Lymph Node-negative Subpopulation (broken by quintiles)

Paclitaxel and Anthracycline (TA)

| Interval | (0, 0.01) | (0.01, 0.034) | (0.034, 0.084) | (0.084, 0.253) | (0.253, 1) |
|---|---|---|---|---|---|
| Counts | 42 | 37 | 39 | 42 | 40 |
| PCR score | 0.071 | 0.081 | 0.051 | 0.190 | 0.325 |
| 95% CI | (0, 0.149) | (0, 0.169) | (0, 0.121) | (0.072, 0.309) | (0.180, 0.470) |

Docetaxel and Anthracycline (TxA)

| Interval | (0, 0.002) | (0.002, 0.054) | (0.054, 0.168) | (0.168, 0.742) | (0.742, 1) |
|---|---|---|---|---|---|
| Counts | 13 | 17 | 15 | 15 | 16 |
| PCR score | 0 | 0 | 0 | 0.467 | 0.938 |
| 95% CI | — | — | — | (0.214, 0.719) | (0.819, 1) |

TABLE 25

Number of Patients Assigned to Each Treatment

| Treatment | Paclitaxel and Anthracycline (TA) | Docetaxel and Anthracycline (TxA) | # of pCR* |
|---|---|---|---|
| Original | 200 | 76 | 51 |
| Assigned based on pCR score | 142 | 134 | 100.97 |

*The original group is observed.

TABLE 26

Heuristically Broken Intervals and pCR Scores for the Lymph Node-negative Subpopulation Paclitaxel and Anthracycline (TA)

| Interval | (0, 0.05) | (0.05, 0.2) | (0.2, 0.5) | (0.5, 1) |
|---|---|---|---|---|
| Counts | 100 | 52 | 33 | 15 |
| PCR score | 0.06 | 0.173 | 0.121 | 0.667 |
| 95% CI | (0.013, 0.107) | (0.07, 0.276) | (0.010, 0.233) | (0.428, 0.905) |

Docetaxel and Anthracycline (TxA)

| Interval | (0, 0.2) | (0.2, 0.6) | (0.6, 1) |
|---|---|---|---|
| Counts | 47 | 10 | 18 |

TABLE 26-continued

Heuristically Broken Intervals and pCR Scores for the Lymph Node-negative Subpopulation

| PCR score | 0.021 | 0.3 | 0.944 |
|---|---|---|---|
| 95% CI | (0, 0.063) | (0.016, 0.584) | (0.839, 1) |

TABLE 27

Number of Patients Assigned to Each Treatment

| Treatment | Paclitaxel and Anthracycline (TA) | Docetaxel and Anthracycline (TxA) | # of pCR* |
|---|---|---|---|
| Original | 200 | 76 | 51 |
| Assigned based on pCR score | 164 | 112 | 94.47 |

*The original group is observed.

Example 8

Individual Probes and Pairs of Probes have Predictive Power

To reveal the prediction abilities of each individual probe (gene) or pair of probes (genes) in the identified set of probes (genes), each probe and each pair of probes in the set of identified probes was used to conduct a 10-fold cross-validation random forest. The f-score of the test portion is reported to show the prediction abilities. To show the superiority of the probes, the results were compared to the result obtained by a randomly selected set of probes which has the same size as the identified probes. 300 sets of probes for each regimen in each population were randomly selected. The mean f-score and its 95% confidence interval (CI) were calculated to show how well the identified probes could perform. The results are shown in FIGS. 5-10.

Tables 28-33 show the f-scores of models of the group consisting of all patients for: A regimen with single probes (Table 28, FIG. 5A), A regimen with pairs of probes (Table 29, FIG. 5B), TA regimen with single probes (Table 30, FIG. 5C), TA regimen with pairs of probes (Table 31, FIG. 5D), TxA regimen with single probes (Table 32, FIG. 5E), and TxA regimen with pairs of probes (Table 33, FIG. 5F).

TABLE 28

F-Scores for the Group Consisting of All Patients, A Regimen, Single Probes

| Gene | Probe | F-score |
|---|---|---|
| SLC12A7 | 218066_at | 0.556 |
| GZMB | 210164_at | 0.588 |
| TAF6L | 213211_s_at | 0.471 |

TABLE 29

F-Scores for the Group Consisting of All Patients, A Regimen, Pairs of Probes

| Gene 1 | Probe 1 | Gene 2 | Probe 2 | F-score |
|---|---|---|---|---|
| SLC12A7 | 218066_at | GZMB | 210164_at | 0.737 |
| SLC12A7 | 218066_at | TAF6L | 213211_s_at | 0.667 |
| GZMB | 210164_at | TAF6L | 213211_s_at | 0.737 |

TABLE 30

F-Scores for the Group Consisting of All Patients, TA Regimen, Single Probes

| Gene | Probe | F-score |
|---|---|---|
| NFIB | 213033_s_at | 0.498 |
| METRN | 219051_x_at | 0.450 |
| ROPN1B | 220425_x_at | 0.541 |
| NFIB | 209289_at | 0.498 |
| TTK | 204822_at | 0.466 |
| NFIB | 213032_at | 0.527 |
| CCND1 | 208712_at | 0.469 |

TABLE 31

F-Scores for the Group Consisting of All Patients, TA Regimen, Pairs of Probes

| Gene 1 | Probe 1 | Gene 2 | Probe 2 | F-score |
|---|---|---|---|---|
| NFIB | 213033_s_at | METRN | 219051_x_at | 0.521 |
| NFIB | 213033_s_at | ROPN1B | 220425_x_at | 0.586 |
| NFIB | 213033_s_at | NFIB | 209289_at | 0.542 |
| NFIB | 213033_s_at | TTK | 204822_at | 0.555 |
| NFIB | 213033_s_at | NFIB | 213032_at | 0.549 |
| NFIB | 213033_s_at | CCND1 | 208712_at | 0.547 |
| METRN | 219051_x_at | ROPN1B | 220425_x_at | 0.579 |
| METRN | 219051_x_at | NFIB | 209289_at | 0.578 |
| METRN | 219051_x_at | TTK | 204822_at | 0.526 |
| METRN | 219051_x_at | NFIB | 213032_at | 0.561 |
| METRN | 219051_x_at | CCND1 | 208712_at | 0.520 |
| ROPN1B | 220425_x_at | NFIB | 209289_at | 0.599 |
| ROPN1B | 220425_x_at | TTK | 204822_at | 0.626 |
| ROPN1B | 220425_x_at | NFIB | 213032_at | 0.627 |
| ROPN1B | 220425_x_at | CCND1 | 208712_at | 0.545 |
| NFIB | 209289_at | TTK | 204822_at | 0.564 |
| NFIB | 209289_at | NFIB | 213032_at | 0.567 |
| NFIB | 209289_at | CCND1 | 208712_at | 0.589 |
| TTK | 204822_at | NFIB | 213032_at | 0.583 |
| TTK | 204822_at | CCND1 | 208712_at | 0.528 |
| NFIB | 213032_at | CCND1 | 208712_at | 0.598 |

TABLE 32

F-Scores for the Group Consisting of All Patients, TxA Regimen, Single Probes

| Gene | Probe | F-score |
|---|---|---|
| PTTG1 | 203554_x_at | 0.648 |
| H2AFZ | 200853_at | 0.613 |
| WDR45L | 209076_s_at | 0.705 |
| DEK | 200934_at | 0.707 |
| H2AFZ | 213911_s_at | 0.587 |
| MCM2 | 202107_s_at | 0.605 |
| USP1 | 202412_s_at | 0.662 |
| CDT1 | 209832_s_at | 0.569 |
| TMEM97 | 212282_at | 0.715 |
| RER1 | 213296_at | 0.603 |
| MCM6 | 201930_at | 0.645 |
| LZTFL1 | 218437_s_at | 0.64 |

TABLE 33

F-Scores for the Group Consisting of All Patients, TxA Regimen, Pairs of Probes

| Gene 1 | Probe 1 | Gene 2 | Probe 2 | F-score |
|---|---|---|---|---|
| PTTG1 | 203554_x_at | H2AFZ | 200853_at | 0.690 |
| PTTG1 | 203554_x_at | WDR45L | 209076_s_at | 0.787 |
| PTTG1 | 203554_x_at | DEK | 200934_at | 0.735 |
| PTTG1 | 203554_x_at | H2AFZ | 213911_s_at | 0.713 |
| PTTG1 | 203554_x_at | MCM2 | 202107_s_at | 0.671 |
| PTTG1 | 203554_x_at | USP1 | 202412_s_at | 0.738 |
| PTTG1 | 203554_x_at | CDT1 | 209832_s_at | 0.699 |
| PTTG1 | 203554_x_at | TMEM97 | 212282_at | 0.768 |
| PTTG1 | 203554_x_at | RER1 | 213296_at | 0.721 |
| PTTG1 | 203554_x_at | MCM6 | 201930_at | 0.728 |
| PTTG1 | 203554_x_at | LZTFL1 | 218437_s_at | 0.735 |
| H2AFZ | 200853_at | WDR45L | 209076_s_at | 0.708 |
| H2AFZ | 200853_at | DEK | 200934_at | 0.706 |
| H2AFZ | 200853_at | H2AFZ | 213911_s_at | 0.662 |
| H2AFZ | 200853_at | MCM2 | 202107_s_at | 0.684 |
| H2AFZ | 200853_at | USP1 | 202412_s_at | 0.747 |
| H2AFZ | 200853_at | CDT1 | 209832_s_at | 0.653 |
| H2AFZ | 200853_at | TMEM97 | 212282_at | 0.769 |
| H2AFZ | 200853_at | RER1 | 213296_at | 0.698 |
| H2AFZ | 200853_at | MCM6 | 201930_at | 0.728 |
| H2AFZ | 200853_at | LZTFL1 | 218437_s_at | 0.707 |
| WDR45L | 209076_s_at | DEK | 200934_at | 0.709 |
| WDR45L | 209076_s_at | H2AFZ | 213911_s_at | 0.699 |
| WDR45L | 209076_s_at | MCM2 | 202107_s_at | 0.757 |
| WDR45L | 209076_s_at | USP1 | 202412_s_at | 0.814 |
| WDR45L | 209076_s_at | CDT1 | 209832_s_at | 0.676 |
| WDR45L | 209076_s_at | TMEM97 | 212282_at | 0.748 |
| WDR45L | 209076_s_at | RER1 | 213296_at | 0.691 |
| WDR45L | 209076_s_at | MCM6 | 201930_at | 0.713 |
| WDR45L | 209076_s_at | LZTFL1 | 218437_s_at | 0.747 |
| DEK | 200934_at | H2AFZ | 213911_s_at | 0.724 |
| DEK | 200934_at | MCM2 | 202107_s_at | 0.711 |
| DEK | 200934_at | USP1 | 202412_s_at | 0.743 |
| DEK | 200934_at | CDT1 | 209832_s_at | 0.714 |
| DEK | 200934_at | TMEM97 | 212282_at | 0.768 |
| DEK | 200934_at | RER1 | 213296_at | 0.737 |
| DEK | 200934_at | MCM6 | 201930_at | 0.731 |
| DEK | 200934_at | LZTFL1 | 218437_s_at | 0.703 |
| H2AFZ | 213911_s_at | MCM2 | 202107_s_at | 0.631 |
| H2AFZ | 213911_s_at | USP1 | 202412_s_at | 0.719 |
| H2AFZ | 213911_s_at | CDT1 | 209832_s_at | 0.667 |
| H2AFZ | 213911_s_at | TMEM97 | 212282_at | 0.732 |
| H2AFZ | 213911_s_at | RER1 | 213296_at | 0.699 |
| H2AFZ | 213911_s_at | MCM6 | 201930_at | 0.702 |
| H2AFZ | 213911_s_at | LZTFL1 | 218437_s_at | 0.667 |
| MCM2 | 202107_s_at | USP1 | 202412_s_at | 0.684 |
| MCM2 | 202107_s_at | CDT1 | 209832_s_at | 0.662 |
| MCM2 | 202107_s_at | TMEM97 | 212282_at | 0.733 |
| MCM2 | 202107_s_at | RER1 | 213296_at | 0.688 |
| MCM2 | 202107_s_at | MCM6 | 201930_at | 0.693 |
| MCM2 | 202107_s_at | LZTFL1 | 218437_s_at | 0.689 |
| USP1 | 202412_s_at | CDT1 | 209832_s_at | 0.716 |

TABLE 33-continued

F-Scores for the Group Consisting of All
Patients, TxA Regimen, Pairs of Probes

| Gene 1 | Probe 1 | Gene 2 | Probe 2 | F-score |
|---|---|---|---|---|
| USP1 | 202412_s_at | TMEM97 | 212282_at | 0.753 |
| USP1 | 202412_s_at | RER1 | 213296_at | 0.709 |
| USP1 | 202412_s_at | MCM6 | 201930_at | 0.736 |
| USP1 | 202412_s_at | LZTFL1 | 218437_s_at | 0.752 |
| CDT1 | 209832_s_at | TMEM97 | 212282_at | 0.747 |
| CDT1 | 209832_s_at | RER1 | 213296_at | 0.653 |
| CDT1 | 209832_s_at | MCM6 | 201930_at | 0.662 |
| CDT1 | 209832_s_at | LZTFL1 | 218437_s_at | 0.676 |
| TMEM97 | 212282_at | RER1 | 213296_at | 0.75 |
| TMEM97 | 212282_at | MCM6 | 201930_at | 0.747 |
| TMEM97 | 212282_at | LZTFL1 | 218437_s_at | 0.813 |
| RER1 | 213296_at | MCM6 | 201930_at | 0.735 |
| RER1 | 213296_at | LZTFL1 | 218437_s_at | 0.691 |
| MCM6 | 201930_at | LZTFL1 | 218437_s_at | 0.737 |

Figure 5A:
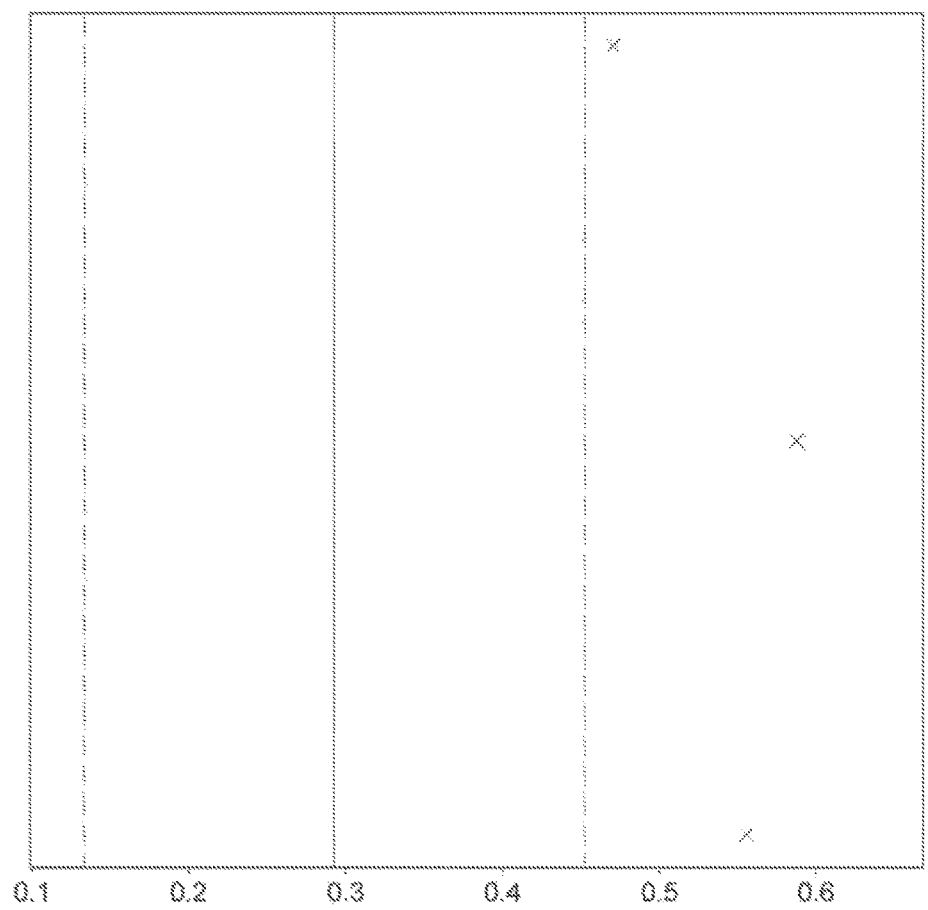
FIG. 5A shows the anthracycline (A) regimen with individual probes.
Figure 5B:
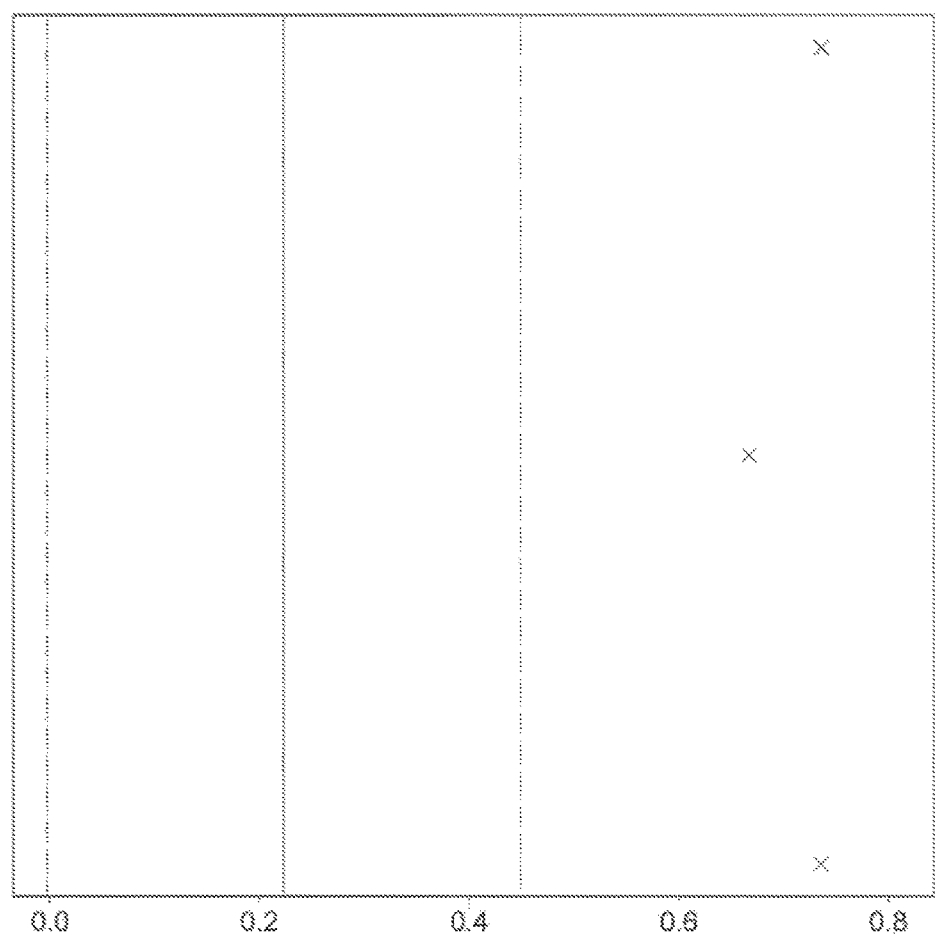
FIG. 5B shows the anthracycline (A) regimen with pairs of probes.
Figure 5C:
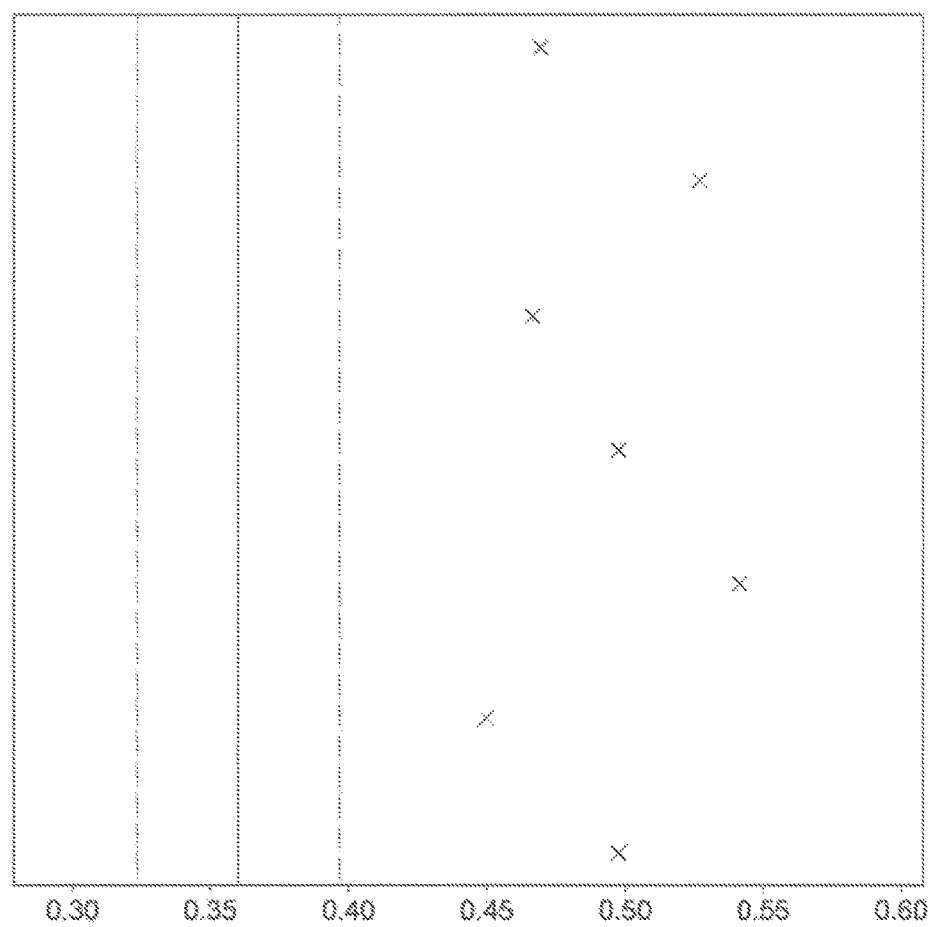
FIG. 5C shows the paclitaxel and anthracycline (TA) regimen with individual probes.
Figure 5D:
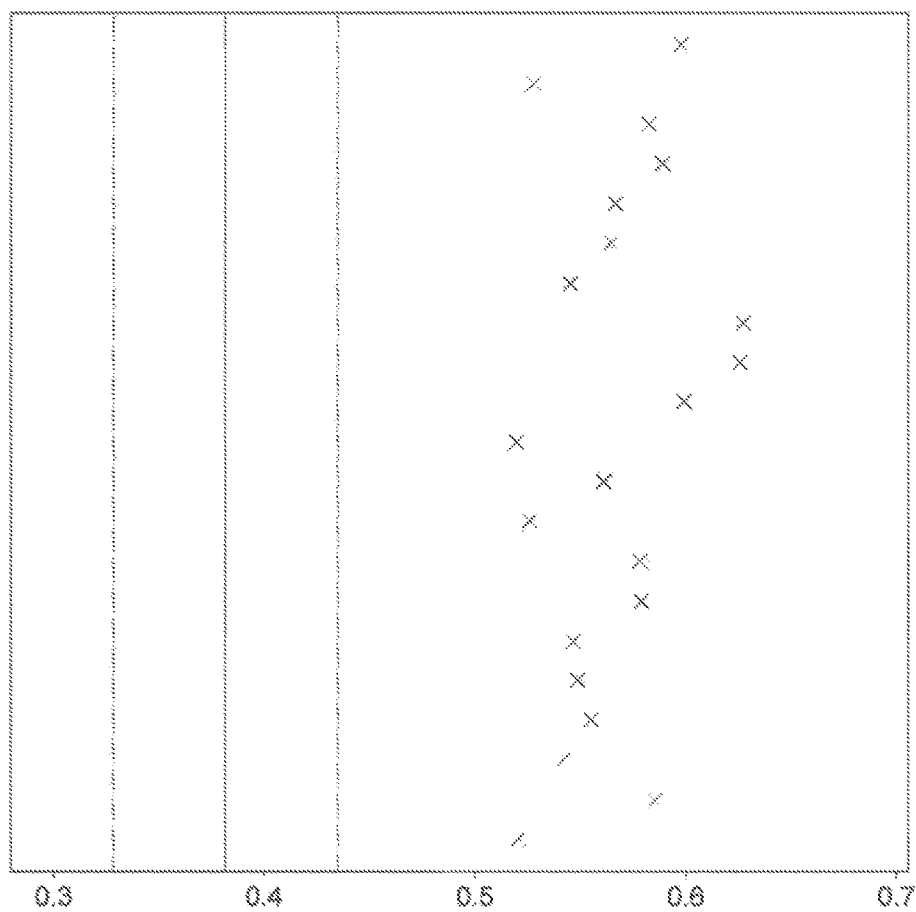
FIG. 5D shows the paclitaxel and anthracycline (TA) regimen with pairs of probes.
Figure 5E:
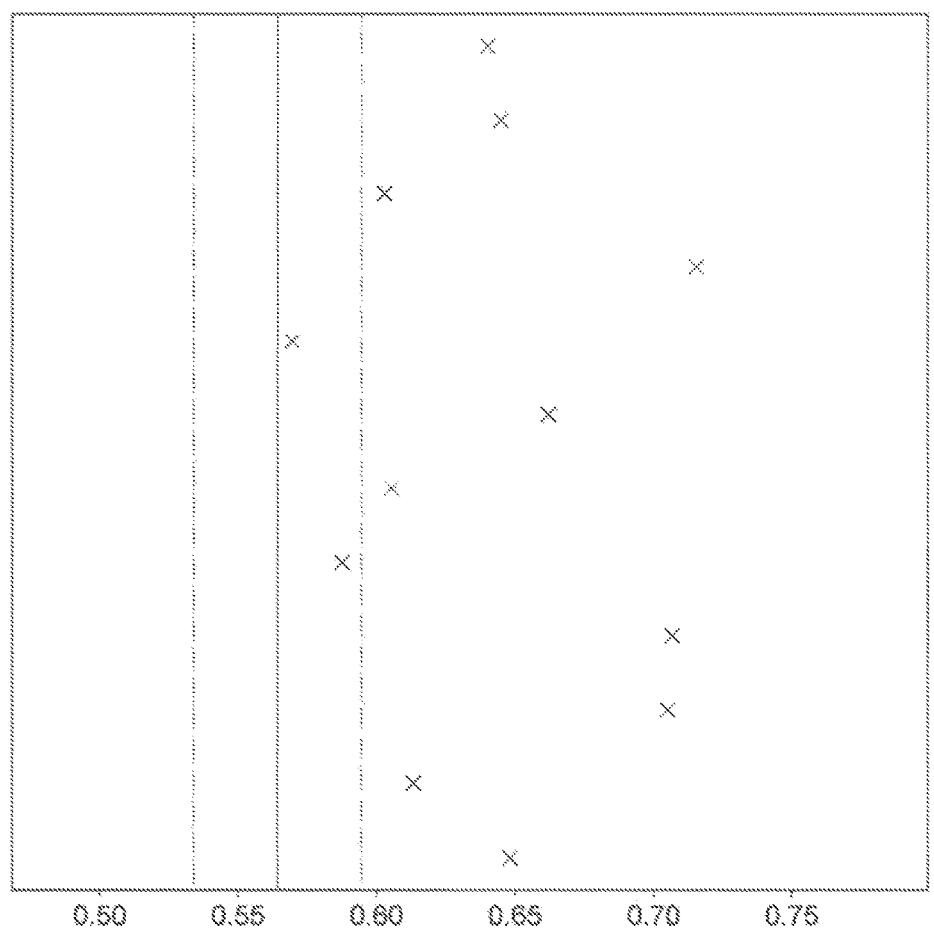
FIG. 5E shows the docetaxel and anthracycline (TxA) regimen with individual probes.
Figure 5F:
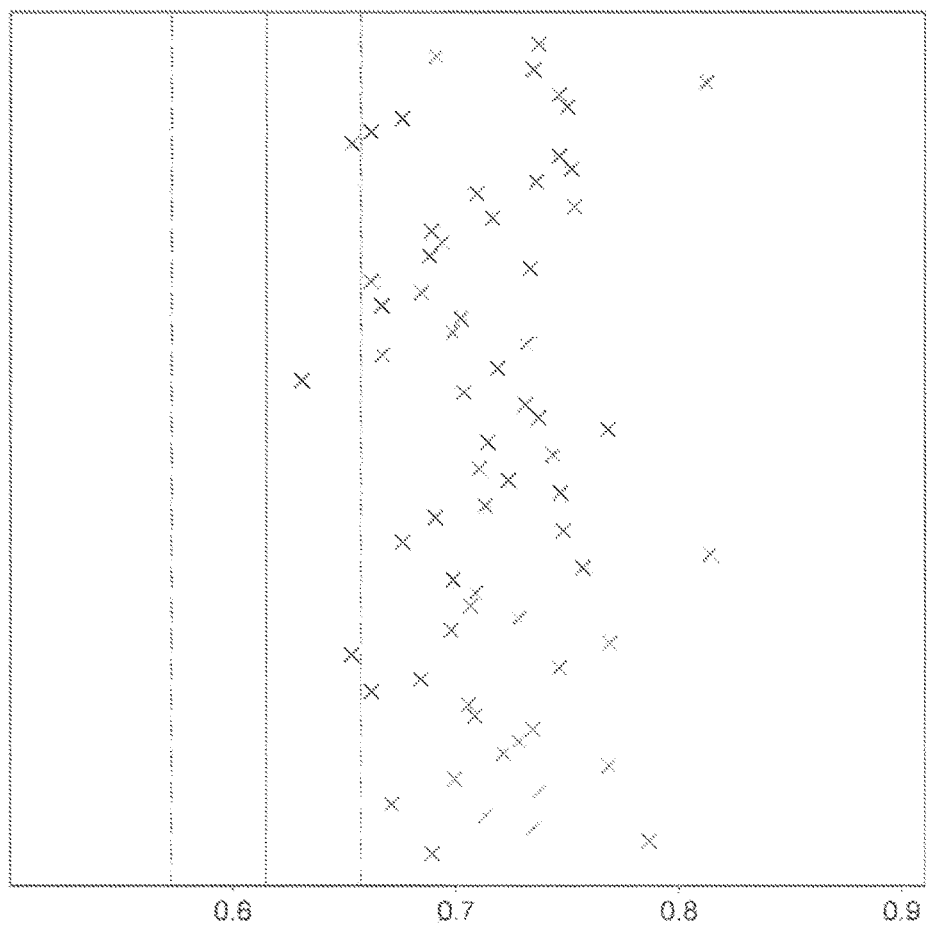
FIG. 5F shows the docetaxel and anthracycline (TxA) regimen with pairs of probes.

For the group of all patients, in regimen TxA, there were two probes sitting inside the 95% CI, which were H2AFZ (213911_s_at) and CDT1 (209832_s_at); and there were three pairs of probes sitting inside the 95% CI, they were: (1). H2AFZ (200853 at) and CDT1 (209832_s_at), (2). H2AFZ (213911_s_at) and MCM2 (202107_s_at), (3). CDT1 (209832_s_at) and RER1 (213296_at) (FIGS. 5C-D). However, none of the above was worse than the mean of the random sets. (FIGS. 5A-F).

Tables 34-39 show the f-scores of models of the group consisting of HER2-negative patients for: A regimen with single probes (Table 34, FIG. 6A), A regimen with pairs of probes (Table 35, FIG. 6B), TA regimen with single probes (Table 36, FIG. 6C), TA regimen with pairs of probes (Table 37, FIG. 6D), TxA regimen with single probes (Table 38, FIG. 6E), and TxA regimen with pairs of probes (Table 39, FIG. 6F).

TABLE 34

F-Scores for the Group Consisting of HER2-
Negative Patients, A Regimen, Single Probes

| Gene | Probe | F-score |
|---|---|---|
| SLC12A7 | 218066_at | 0.5 |
| GZMB | 210164_at | 0.556 |
| C11orf17 | 219953_s_at | 0.471 |
| TAF6L | 213211_s_at | 0.556 |
| CCL5 | 204655_at | 0.632 |
| XCL1 /// XCL2 | 214567_s_at | 0.556 |

TABLE 35

F-Scores for the Group Consisting of HER2-
Negative Patients, A Regimen, Pairs of Probes

| Gene 1 | Probe 1 | Gene 2 | Probe 2 | F-score |
|---|---|---|---|---|
| SLC12A7 | 218066_at | GZMB | 210164_at | 0.762 |
| SLC12A7 | 218066_at | C11orf17 | 219953_s_at | 0.556 |
| SLC12A7 | 218066_at | TAF6L | 213211_s_at | 0.7 |
| SLC12A7 | 218066_at | CCL5 | 204655_at | 0.5 |
| SLC12A7 | 218066_at | XCL1 /// XCL2 | 214567_s_at | 0.6 |
| GZMB | 210164_at | C11orf17 | 219953_s_at | 0.667 |
| GZMB | 210164_at | TAF6L | 213211_s_at | 0.737 |
| GZMB | 210164_at | CCL5 | 204655_at | 0.588 |
| GZMB | 210164_at | XCL1 /// XCL2 | 214567_s_at | 0.588 |
| C11orf17 | 219953_s_at | TAF6L | 213211_s_at | 0.4 |
| C11orf17 | 219953_s_at | CCL5 | 204655_at | 0.444 |
| C11orf17 | 219953_s_at | XCL1 /// XCL2 | 214567_s_at | 0.667 |
| TAF6L | 213211_s_at | CCL5 | 204655_at | 0.667 |

TABLE 35-continued

F-Scores for the Group Consisting of HER2-
Negative Patients, A Regimen, Pairs of Probes

| Gene 1 | Probe 1 | Gene 2 | Probe 2 | F-score |
|---|---|---|---|---|
| TAF6L | 213211_s_at | XCL1 /// XCL2 | 214567_s_at | 0.667 |
| CCL5 | 204655_at | XCL1 /// XCL2 | 214567_s_at | 0.632 |

TABLE 36

F-Scores for the Group Consisting of HER2-Negative
Patients, TA Regimen, Single Probes

| Gene | Probe | F-score |
|---|---|---|
| NFIB | 213033_s_at | 0.505 |
| NFIB | 209289_at | 0.462 |
| ROPN1B | 220425_x_at | 0.567 |
| NFIB | 213032_at | 0.511 |
| TTK | 204822_at | 0.441 |
| NFIB | 211467_s_at | 0.420 |
| MELK | 204825_at | 0.449 |
| CTSL2 | 210074_at | 0.536 |
| METRN | 219051_x_at | 0.424 |

TABLE 37

F-Scores for the Group Consisting of HER2-Negative
Patients, TA Regimen, Pairs of Probes

| Gene 1 | Probe 1 | Gene 2 | Probe 2 | F-score |
|---|---|---|---|---|
| NFIB | 213033_s_at | NFIB | 209289_at | 0.519 |
| NFIB | 213033_s_at | ROPN1B | 220425_x_at | 0.561 |
| NFIB | 213033_s_at | NFIB | 213032_at | 0.511 |
| NFIB | 213033_s_at | TTK | 204822_at | 0.529 |
| NFIB | 213033_s_at | NFIB | 211467_s_at | 0.521 |
| NFIB | 213033_s_at | MELK | 204825_at | 0.511 |
| NFIB | 213033_s_at | CTSL2 | 210074_at | 0.545 |
| NFIB | 213033_s_at | METRN | 219051_x_at | 0.503 |
| NFIB | 209289_at | ROPN1B | 220425_x_at | 0.579 |
| NFIB | 209289_at | NFIB | 213032_at | 0.527 |
| NFIB | 209289_at | TTK | 204822_at | 0.545 |
| NFIB | 209289_at | NFIB | 211467_s_at | 0.467 |
| NFIB | 209289_at | MELK | 204825_at | 0.544 |
| NFIB | 209289_at | CTSL2 | 210074_at | 0.566 |
| NFIB | 209289_at | METRN | 219051_x_at | 0.541 |
| ROPN1B | 220425_x_at | NFIB | 213032_at | 0.626 |
| ROPN1B | 220425_x_at | TTK | 204822_at | 0.602 |
| ROPN1B | 220425_x_at | NFIB | 211467_s_at | 0.558 |
| ROPN1B | 220425_x_at | MELK | 204825_at | 0.598 |
| ROPN1B | 220425_x_at | CTSL2 | 210074_at | 0.621 |
| ROPN1B | 220425_x_at | METRN | 219051_x_at | 0.516 |
| NFIB | 213032_at | TTK | 204822_at | 0.589 |
| NFIB | 213032_at | NFIB | 211467_s_at | 0.545 |
| NFIB | 213032_at | MELK | 204825_at | 0.545 |
| NFIB | 213032_at | CTSL2 | 210074_at | 0.582 |
| NFIB | 213032_at | METRN | 219051_x_at | 0.581 |
| TTK | 204822_at | NFIB | 211467_s_at | 0.503 |
| TTK | 204822_at | MELK | 204825_at | 0.453 |
| TTK | 204822_at | CTSL2 | 210074_at | 0.560 |
| TTK | 204822_at | METRN | 219051_x_at | 0.489 |
| NFIB | 211467_s_at | MELK | 204825_at | 0.511 |
| NFIB | 211467_s_at | CTSL2 | 210074_at | 0.551 |
| NFIB | 211467_s_at | METRN | 219051_x_at | 0.489 |
| MELK | 204825_at | CTSL2 | 210074_at | 0.578 |
| MELK | 204825_at | METRN | 219051_x_at | 0.448 |
| CTSL2 | 210074_at | METRN | 219051_x_at | 0.541 |

TABLE 38

F-Scores for the Group Consisting of HER2-Negative Patients, TxA Regimen, Single Probes

| Gene | Probe | F-score |
|---|---|---|
| TPX2 | 210052_s_at | 0.752 |
| PTTG1 | 203554_x_at | 0.783 |
| MCM2 | 202107_s_at | 0.695 |
| MCM6 | 201930_at | 0.786 |
| AURKA | 204092_s_at | 0.656 |
| CDKN2C | 204159_at | 0.826 |
| BRP44 | 202427_s_at | 0.733 |
| H2AFZ | 200853_at | 0.744 |
| PNP | 201695_s_at | 0.797 |
| SMC4 | 201664_at | 0.708 |
| DEK | 200934_at | 0.790 |
| TMEM97 | 212282_at | 0.707 |
| AURKA | 208079_s_at | 0.754 |
| NR4A2 | 216248_s_at | 0.649 |
| C3orf37 | 201678_s_at | 0.723 |
| LZTFL1 | 218437_s_at | 0.704 |
| MTPAP | 218947_s_at | 0.718 |
| CDC25B | 201853_s_at | 0.8 |
| ABCF1 | 200045_at | 0.693 |

TABLE 39

F-Scores for the Group Consisting of HER2-Negative Patients, TxA Regimen, Pairs of Probes

| Gene 1 | Probe 1 | Gene 2 | Probe 2 | f-score |
|---|---|---|---|---|
| TPX2 | 210052_s_at | PTTG1 | 203554_x_at | 0.821 |
| TPX2 | 210052_s_at | MCM2 | 202107_s_at | 0.821 |
| TPX2 | 210052_s_at | MCM6 | 201930_at | 0.807 |
| TPX2 | 210052_s_at | AURKA | 204092_s_at | 0.748 |
| TPX2 | 210052_s_at | CDKN2C | 204159_at | 0.85 |
| TPX2 | 210052_s_at | BRP44 | 202427_s_at | 0.821 |
| TPX2 | 210052_s_at | H2AFZ | 200853_at | 0.783 |
| TPX2 | 210052_s_at | PNP | 201695_s_at | 0.810 |
| TPX2 | 210052_s_at | SMC4 | 201664_at | 0.825 |
| TPX2 | 210052_s_at | DEK | 200934_at | 0.862 |
| TPX2 | 210052_s_at | TMEM97 | 212282_at | 0.807 |
| TPX2 | 210052_s_at | AURKA | 208079_s_at | 0.780 |
| TPX2 | 210052_s_at | NR4A2 | 216248_s_at | 0.817 |
| TPX2 | 210052_s_at | C3orf37 | 201678_s_at | 0.776 |
| TPX2 | 210052_s_at | LZTFL1 | 218437_s_at | 0.803 |
| TPX2 | 210052_s_at | MTPAP | 218947_s_at | 0.772 |
| TPX2 | 210052_s_at | CDC25B | 201853_s_at | 0.869 |
| TPX2 | 210052_s_at | ABCF1 | 200045_at | 0.752 |
| PTTG1 | 203554_x_at | MCM2 | 202107_s_at | 0.783 |
| PTTG1 | 203554_x_at | MCM6 | 201930_at | 0.807 |
| PTTG1 | 203554_x_at | AURKA | 204092_s_at | 0.760 |
| PTTG1 | 203554_x_at | CDKN2C | 204159_at | 0.869 |
| PTTG1 | 203554_x_at | BRP44 | 202427_s_at | 0.833 |
| PTTG1 | 203554_x_at | H2AFZ | 200853_at | 0.793 |
| PTTG1 | 203554_x_at | PNP | 201695_s_at | 0.862 |
| PTTG1 | 203554_x_at | SMC4 | 201664_at | 0.85 |
| PTTG1 | 203554_x_at | DEK | 200934_at | 0.829 |
| PTTG1 | 203554_x_at | TMEM97 | 212282_at | 0.839 |
| PTTG1 | 203554_x_at | AURKA | 208079_s_at | 0.836 |
| PTTG1 | 203554_x_at | NR4A2 | 216248_s_at | 0.833 |
| PTTG1 | 203554_x_at | C3orf37 | 201678_s_at | 0.777 |
| PTTG1 | 203554_x_at | LZTFL1 | 218437_s_at | 0.846 |
| PTTG1 | 203554_x_at | MTPAP | 218947_s_at | 0.847 |
| PTTG1 | 203554_x_at | CDC25B | 201853_s_at | 0.843 |
| PTTG1 | 203554_x_at | ABCF1 | 200045_at | 0.8 |
| MCM2 | 202107_s_at | MCM6 | 201930_at | 0.793 |
| MCM2 | 202107_s_at | AURKA | 204092_s_at | 0.745 |
| MCM2 | 202107_s_at | CDKN2C | 204159_at | 0.793 |
| MCM2 | 202107_s_at | BRP44 | 202427_s_at | 0.783 |
| MCM2 | 202107_s_at | H2AFZ | 200853_at | 0.733 |
| MCM2 | 202107_s_at | PNP | 201695_s_at | 0.748 |
| MCM2 | 202107_s_at | SMC4 | 201664_at | 0.814 |
| MCM2 | 202107_s_at | DEK | 200934_at | 0.797 |
| MCM2 | 202107_s_at | TMEM97 | 212282_at | 0.793 |
| MCM2 | 202107_s_at | AURKA | 208079_s_at | 0.737 |
| MCM2 | 202107_s_at | NR4A2 | 216248_s_at | 0.793 |
| MCM2 | 202107_s_at | C3orf37 | 201678_s_at | 0.773 |
| MCM2 | 202107_s_at | LZTFL1 | 218437_s_at | 0.739 |
| MCM2 | 202107_s_at | MTPAP | 218947_s_at | 0.759 |
| MCM2 | 202107_s_at | CDC25B | 201853_s_at | 0.813 |
| MCM2 | 202107_s_at | ABCF1 | 200045_at | 0.729 |
| MCM6 | 201930_at | AURKA | 204092_s_at | 0.748 |
| MCM6 | 201930_at | CDKN2C | 204159_at | 0.85 |
| MCM6 | 201930_at | BRP44 | 202427_s_at | 0.810 |
| MCM6 | 201930_at | H2AFZ | 200853_at | 0.797 |
| MCM6 | 201930_at | PNP | 201695_s_at | 0.847 |
| MCM6 | 201930_at | SMC4 | 201664_at | 0.833 |
| MCM6 | 201930_at | DEK | 200934_at | 0.817 |
| MCM6 | 201930_at | TMEM97 | 212282_at | 0.824 |
| MCM6 | 201930_at | AURKA | 208079_s_at | 0.75 |
| MCM6 | 201930_at | NR4A2 | 216248_s_at | 0.790 |
| MCM6 | 201930_at | C3orf37 | 201678_s_at | 0.826 |
| MCM6 | 201930_at | LZTFL1 | 218437_s_at | 0.817 |
| MCM6 | 201930_at | MTPAP | 218947_s_at | 0.767 |
| MCM6 | 201930_at | CDC25B | 201853_s_at | 0.867 |
| MCM6 | 201930_at | ABCF1 | 200045_at | 0.803 |
| AURKA | 204092_s_at | CDKN2C | 204159_at | 0.8 |
| AURKA | 204092_s_at | BRP44 | 202427_s_at | 0.726 |
| AURKA | 204092_s_at | H2AFZ | 200853_at | 0.75 |
| AURKA | 204092_s_at | PNP | 201695_s_at | 0.773 |
| AURKA | 204092_s_at | SMC4 | 201664_at | 0.786 |
| AURKA | 204092_s_at | DEK | 200934_at | 0.729 |
| AURKA | 204092_s_at | TMEM97 | 212282_at | 0.724 |
| AURKA | 204092_s_at | AURKA | 208079_s_at | 0.724 |
| AURKA | 204092_s_at | NR4A2 | 216248_s_at | 0.807 |
| AURKA | 204092_s_at | C3orf37 | 201678_s_at | 0.726 |
| AURKA | 204092_s_at | LZTFL1 | 218437_s_at | 0.742 |
| AURKA | 204092_s_at | MTPAP | 218947_s_at | 0.691 |
| AURKA | 204092_s_at | CDC25B | 201853_s_at | 0.836 |
| AURKA | 204092_s_at | ABCF1 | 200045_at | 0.703 |
| CDKN2C | 204159_at | BRP44 | 202427_s_at | 0.814 |
| CDKN2C | 204159_at | H2AFZ | 200853_at | 0.829 |
| CDKN2C | 204159_at | PNP | 201695_s_at | 0.773 |
| CDKN2C | 204159_at | SMC4 | 201664_at | 0.845 |
| CDKN2C | 204159_at | DEK | 200934_at | 0.826 |
| CDKN2C | 204159_at | TMEM97 | 212282_at | 0.842 |
| CDKN2C | 204159_at | AURKA | 208079_s_at | 0.840 |
| CDKN2C | 204159_at | NR4A2 | 216248_s_at | 0.852 |
| CDKN2C | 204159_at | C3orf37 | 201678_s_at | 0.803 |
| CDKN2C | 204159_at | LZTFL1 | 218437_s_at | 0.867 |
| CDKN2C | 204159_at | MTPAP | 218947_s_at | 0.783 |
| CDKN2C | 204159_at | CDC25B | 201853_s_at | 0.867 |
| CDKN2C | 204159_at | ABCF1 | 200045_at | 0.817 |
| BRP44 | 202427_s_at | H2AFZ | 200853_at | 0.783 |
| BRP44 | 202427_s_at | PNP | 201695_s_at | 0.803 |
| BRP44 | 202427_s_at | SMC4 | 201664_at | 0.848 |
| BRP44 | 202427_s_at | DEK | 200934_at | 0.817 |
| BRP44 | 202427_s_at | TMEM97 | 212282_at | 0.777 |
| BRP44 | 202427_s_at | AURKA | 208079_s_at | 0.772 |
| BRP44 | 202427_s_at | NR4A2 | 216248_s_at | 0.797 |
| BRP44 | 202427_s_at | C3orf37 | 201678_s_at | 0.759 |
| BRP44 | 202427_s_at | LZTFL1 | 218437_s_at | 0.772 |
| BRP44 | 202427_s_at | MTPAP | 218947_s_at | 0.765 |
| BRP44 | 202427_s_at | CDC25B | 201853_s_at | 0.881 |
| BRP44 | 202427_s_at | ABCF1 | 200045_at | 0.768 |
| H2AFZ | 200853_at | PNP | 201695_s_at | 0.823 |
| H2AFZ | 200853_at | SMC4 | 201664_at | 0.840 |
| H2AFZ | 200853_at | DEK | 200934_at | 0.780 |
| H2AFZ | 200853_at | TMEM97 | 212282_at | 0.826 |
| H2AFZ | 200853_at | AURKA | 208079_s_at | 0.8 |
| H2AFZ | 200853_at | NR4A2 | 216248_s_at | 0.816 |
| H2AFZ | 200853_at | C3orf37 | 201678_s_at | 0.862 |
| H2AFZ | 200853_at | LZTFL1 | 218437_s_at | 0.756 |
| H2AFZ | 200853_at | MTPAP | 218947_s_at | 0.793 |
| H2AFZ | 200853_at | CDC25B | 201853_s_at | 0.885 |
| H2AFZ | 200853_at | ABCF1 | 200045_at | 0.760 |
| PNP | 201695_s_at | SMC4 | 201664_at | 0.807 |
| PNP | 201695_s_at | DEK | 200934_at | 0.797 |
| PNP | 201695_s_at | TMEM97 | 212282_at | 0.810 |
| PNP | 201695_s_at | AURKA | 208079_s_at | 0.769 |

TABLE 39-continued

F-Scores for the Group Consisting of HER2-Negative Patients, TxA Regimen, Pairs of Probes

| Gene 1 | Probe 1 | Gene 2 | Probe 2 | f-score |
|---|---|---|---|---|
| PNP | 201695_s_at | NR4A2 | 216248_s_at | 0.8 |
| PNP | 201695_s_at | C3orf37 | 201678_s_at | 0.754 |
| PNP | 201695_s_at | LZTFL1 | 218437_s_at | 0.790 |
| PNP | 201695_s_at | MTPAP | 218947_s_at | 0.829 |
| PNP | 201695_s_at | CDC25B | 201853_s_at | 0.833 |
| PNP | 201695_s_at | ABCF1 | 200045_at | 0.814 |
| SMC4 | 201664_at | DEK | 200934_at | 0.783 |
| SMC4 | 201664_at | TMEM97 | 212282_at | 0.803 |
| SMC4 | 201664_at | AURKA | 208079_s_at | 0.885 |
| SMC4 | 201664_at | NR4A2 | 216248_s_at | 0.768 |
| SMC4 | 201664_at | C3orf37 | 201678_s_at | 0.783 |
| SMC4 | 201664_at | LZTFL1 | 218437_s_at | 0.797 |
| SMC4 | 201664_at | MTPAP | 218947_s_at | 0.810 |
| SMC4 | 201664_at | CDC25B | 201853_s_at | 0.902 |
| SMC4 | 201664_at | ABCF1 | 200045_at | 0.817 |
| DEK | 200934_at | TMEM97 | 212282_at | 0.826 |
| DEK | 200934_at | AURKA | 208079_s_at | 0.777 |
| DEK | 200934_at | NR4A2 | 216248_s_at | 0.780 |
| DEK | 200934_at | C3orf37 | 201678_s_at | 0.829 |
| DEK | 200934_at | LZTFL1 | 218437_s_at | 0.797 |
| DEK | 200934_at | MTPAP | 218947_s_at | 0.780 |
| DEK | 200934_at | CDC25B | 201853_s_at | 0.84 |
| DEK | 200934_at | ABCF1 | 200045_at | 0.835 |
| TMEM97 | 212282_at | AURKA | 208079_s_at | 0.786 |
| TMEM97 | 212282_at | NR4A2 | 216248_s_at | 0.754 |
| TMEM97 | 212282_at | C3orf37 | 201678_s_at | 0.797 |
| TMEM97 | 212282_at | LZTFL1 | 218437_s_at | 0.810 |
| TMEM97 | 212282_at | MTPAP | 218947_s_at | 0.836 |
| TMEM97 | 212282_at | CDC25B | 201853_s_at | 0.862 |
| TMEM97 | 212282_at | ABCF1 | 200045_at | 0.786 |
| AURKA | 208079_s_at | NR4A2 | 216248_s_at | 0.777 |
| AURKA | 208079_s_at | C3orf37 | 201678_s_at | 0.756 |
| AURKA | 208079_s_at | LZTFL1 | 218437_s_at | 0.793 |
| AURKA | 208079_s_at | MTPAP | 218947_s_at | 0.8 |
| AURKA | 208079_s_at | CDC25B | 201853_s_at | 0.894 |
| AURKA | 208079_s_at | ABCF1 | 200045_at | 0.739 |
| NR4A2 | 216248_s_at | C3orf37 | 201678_s_at | 0.803 |
| NR4A2 | 216248_s_at | LZTFL1 | 218437_s_at | 0.780 |
| NR4A2 | 216248_s_at | MTPAP | 218947_s_at | 0.786 |
| NR4A2 | 216248_s_at | CDC25B | 201853_s_at | 0.836 |
| NR4A2 | 216248_s_at | ABCF1 | 200045_at | 0.816 |
| C3orf37 | 201678_s_at | LZTFL1 | 218437_s_at | 0.833 |
| C3orf37 | 201678_s_at | MTPAP | 218947_s_at | 0.779 |
| C3orf37 | 201678_s_at | CDC25B | 201853_s_at | 0.807 |
| C3orf37 | 201678_s_at | ABCF1 | 200045_at | 0.794 |
| LZTFL1 | 218437_s_at | MTPAP | 218947_s_at | 0.789 |
| LZTFL1 | 218437_s_at | CDC25B | 201853_s_at | 0.852 |
| LZTFL1 | 218437_s_at | ABCF1 | 200045_at | 0.820 |
| MTPAP | 218947_s_at | CDC25B | 201853_s_at | 0.841 |
| MTPAP | 218947_s_at | ABCF1 | 200045_at | 0.773 |
| CDC25B | 201853_s_at | ABCF1 | 200045_at | 0.780 |

Figure 6A:
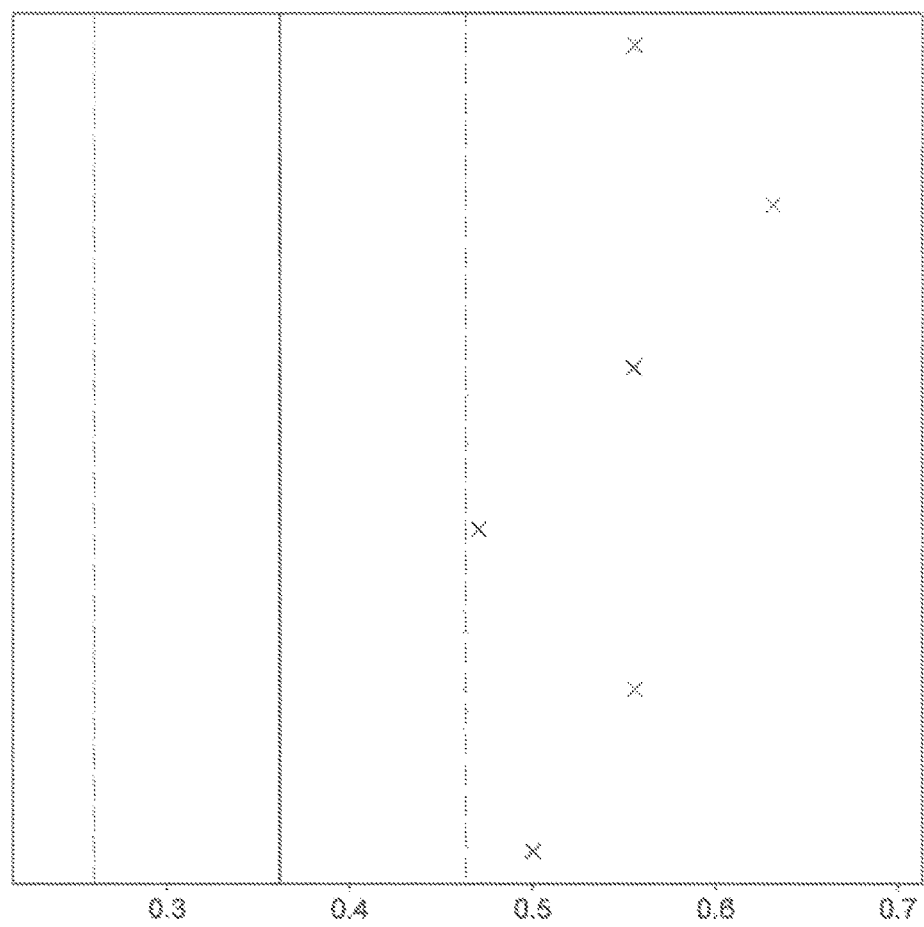
FIG. 6A shows the anthracycline (A) regimen with individual probes.
Figure 6B:
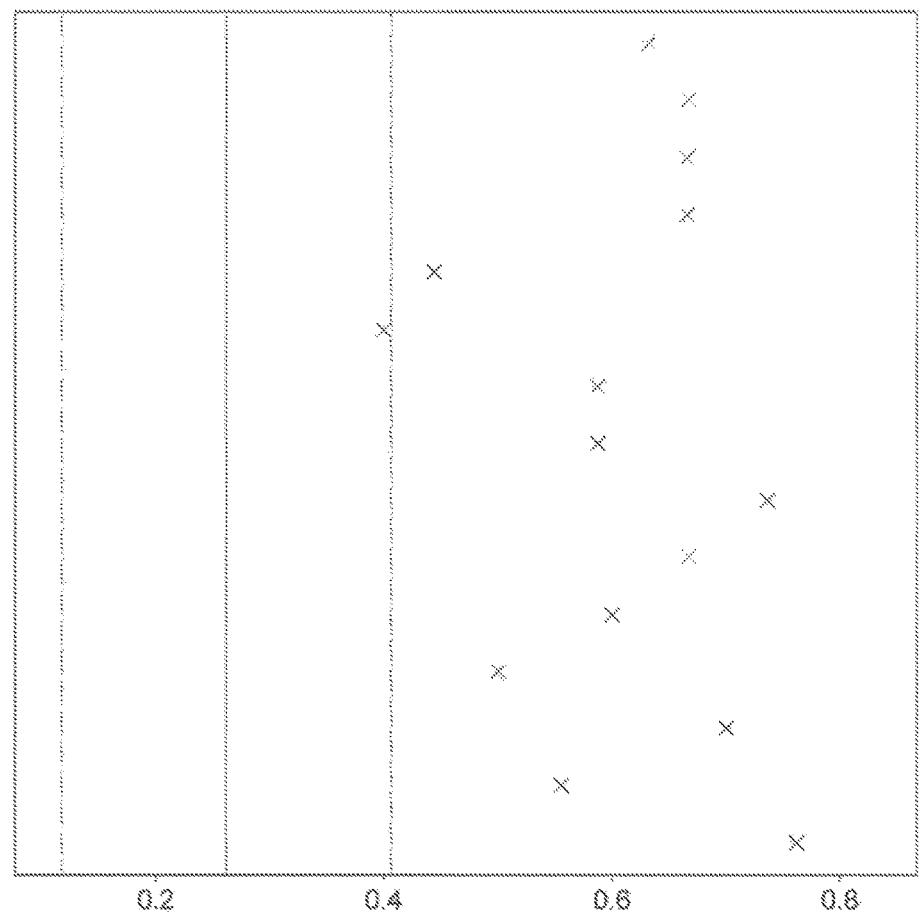
FIG. 6B shows the anthracycline (A) regimen with pairs of probes.
Figure 6C:
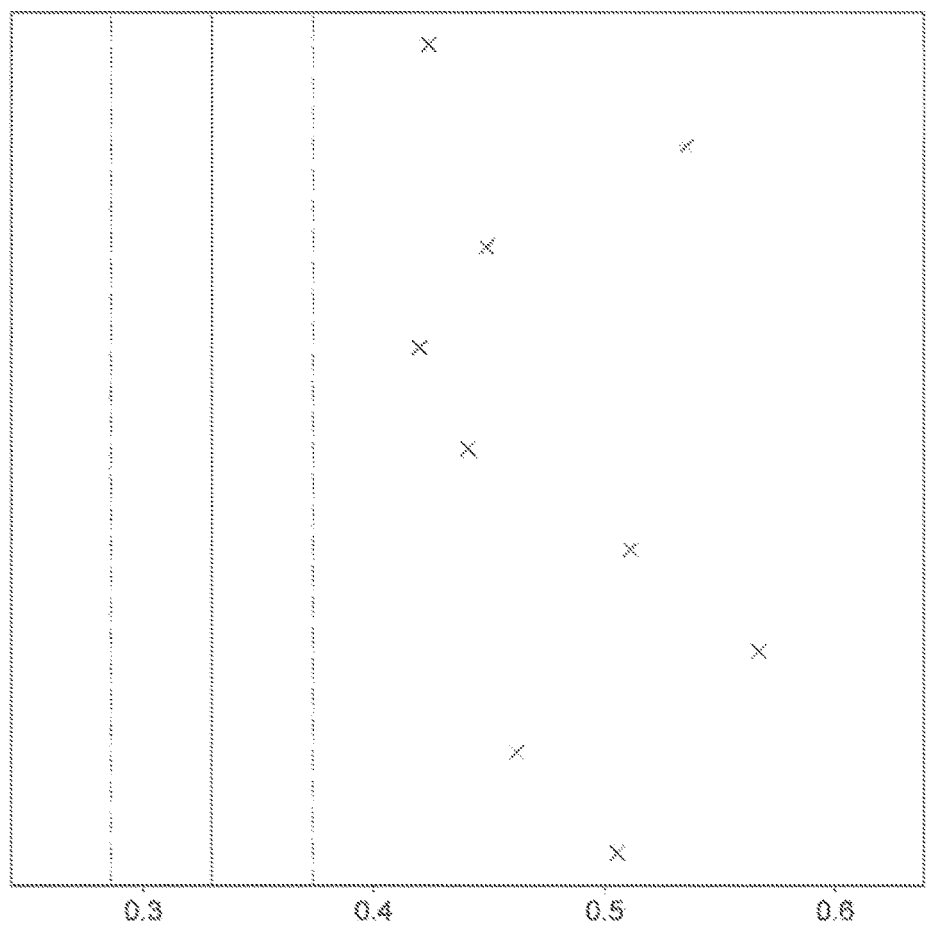
FIG. 6C shows the paclitaxel and anthracycline (TA) regimen with individual probes.
Figure 6D:
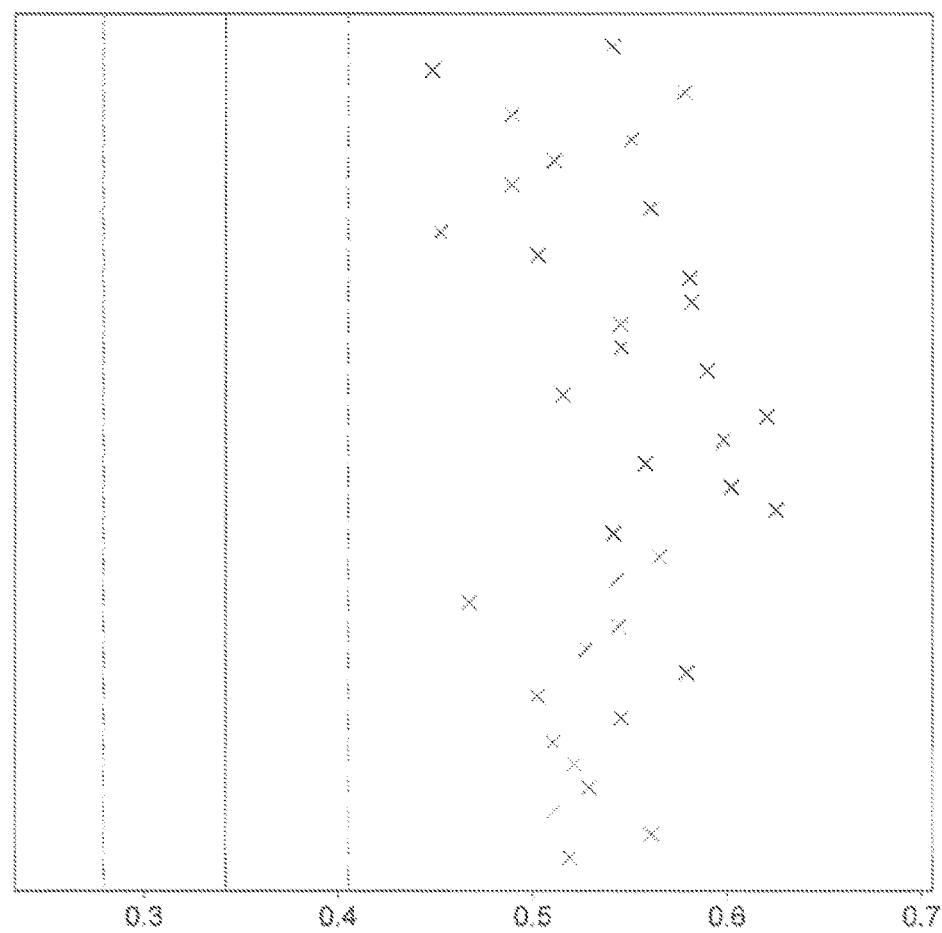
FIG. 6D shows the paclitaxel and anthracycline (TA) regimen with pairs of probes.
Figure 6E:
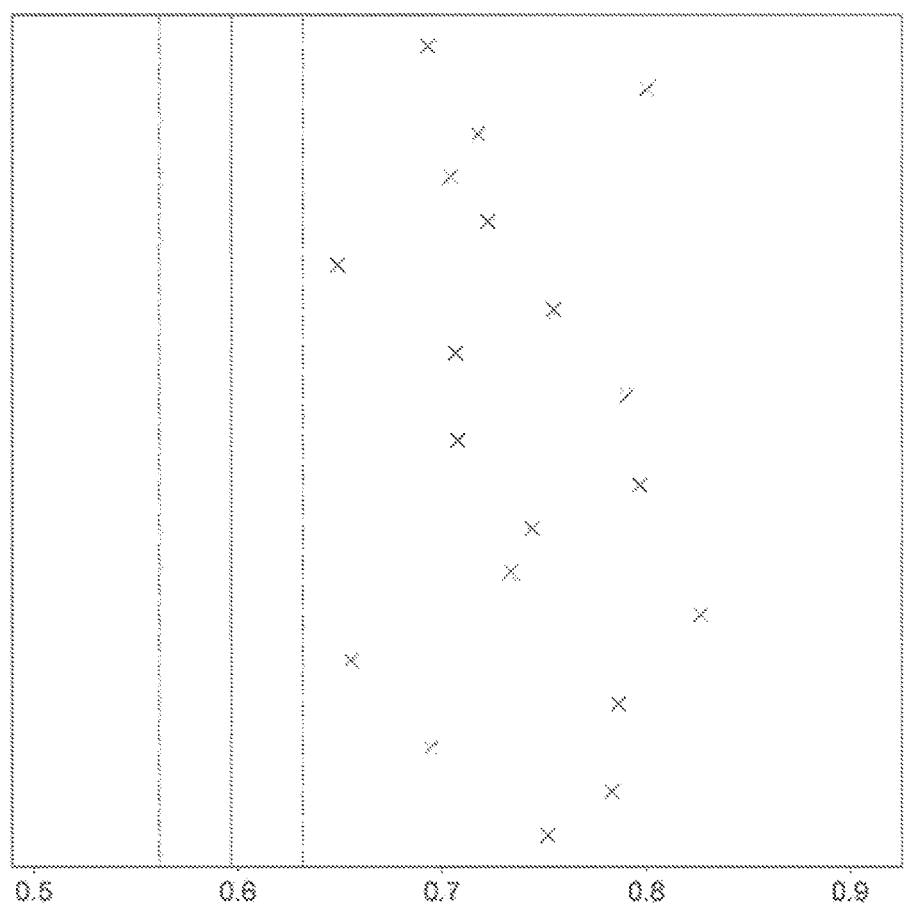
FIG. 6E shows the docetaxel and anthracycline (TxA) regimen with individual probes.
Figure 6F:
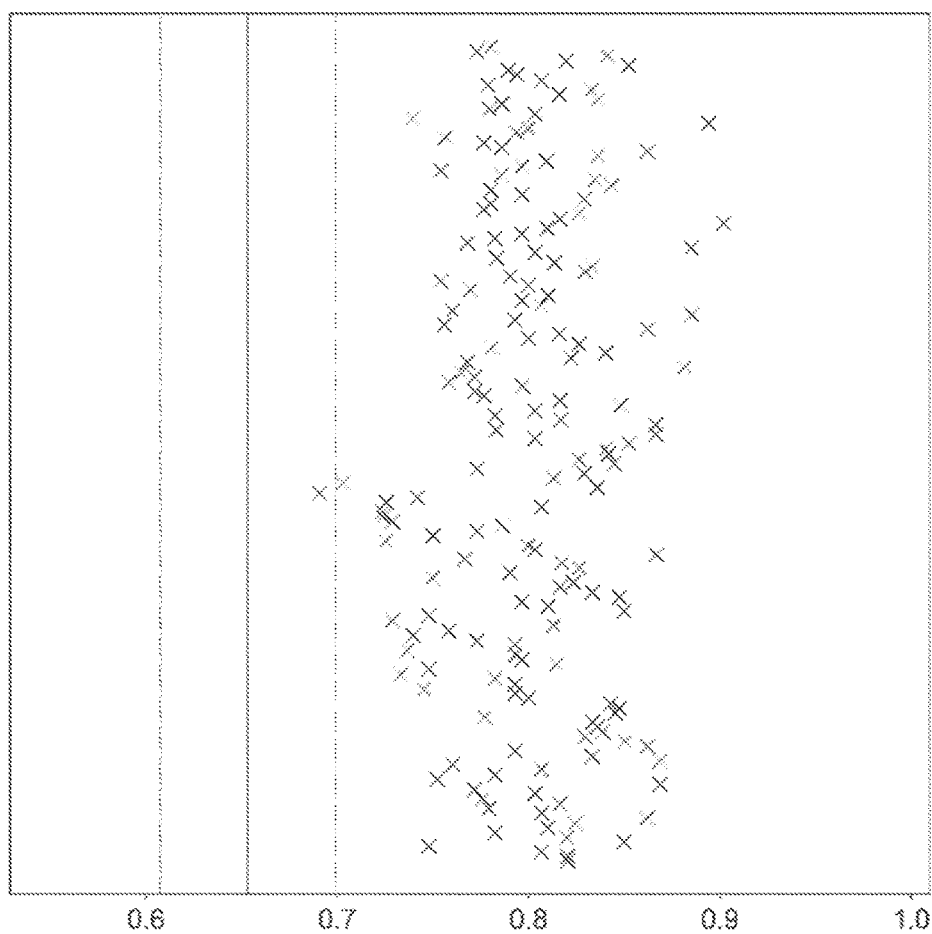
FIG. 6F shows the docetaxel and anthracycline (TxA) regimen with pair of probes.
Figure 7A:
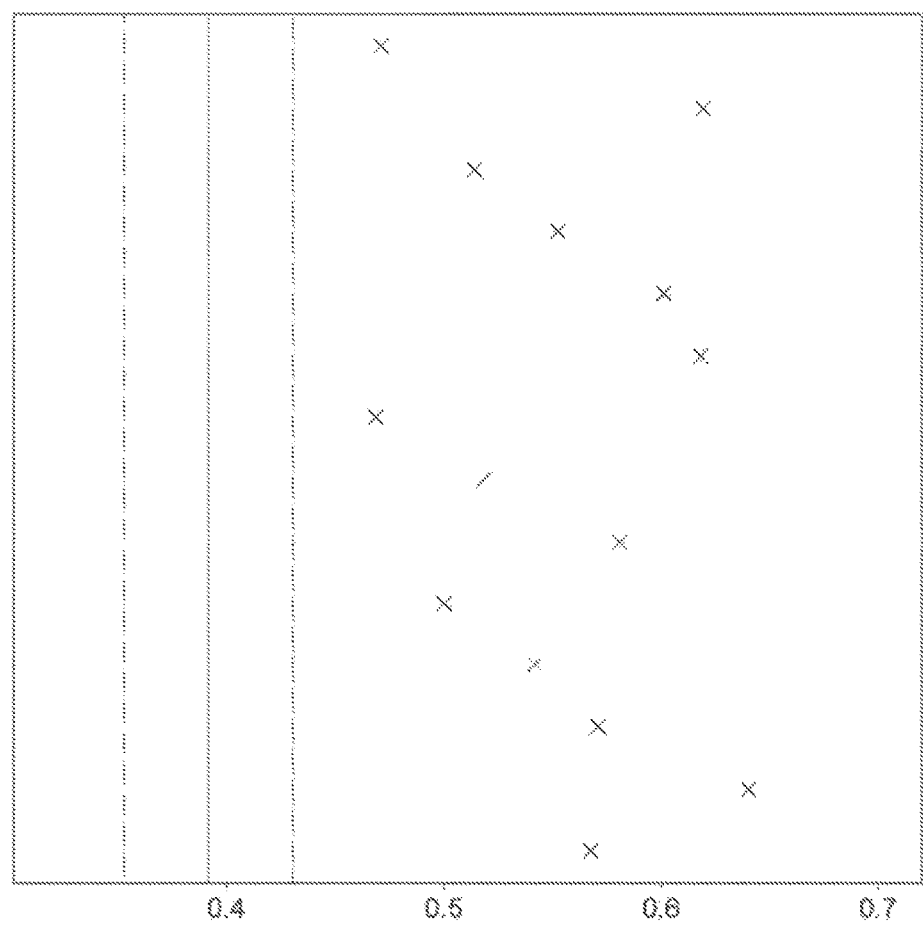
FIG. 7A shows the paclitaxel and anthracycline (TA) regimen with individual probes.
Figure 7B:
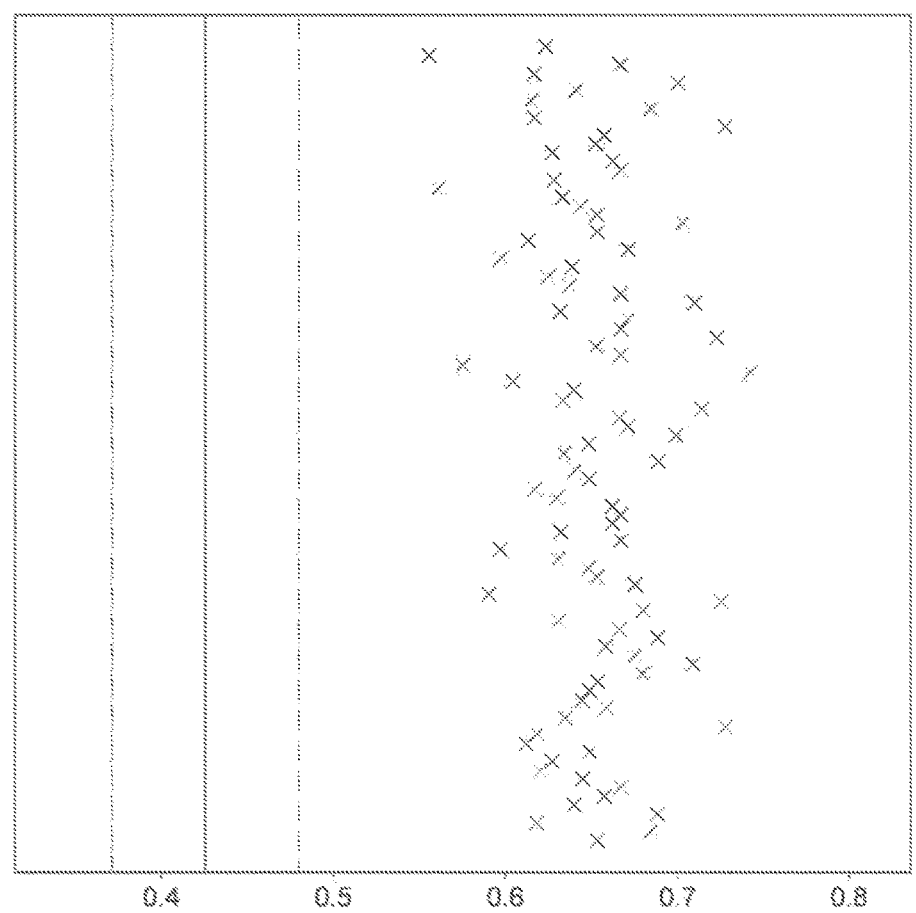
FIG. 7B shows the paclitaxel and anthracycline (TA) regimen with pairs of probes.
Figure 7C:
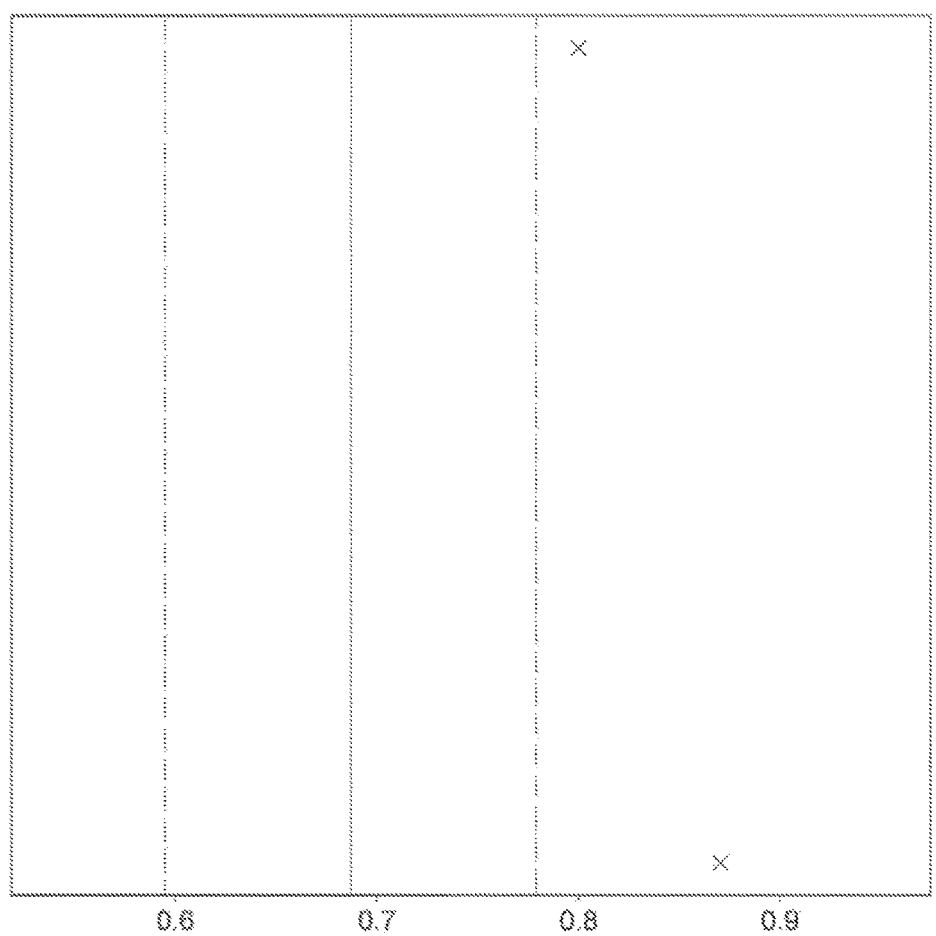
FIG. 7C shows the docetaxel and anthracycline (TxA) regimen with individual probes.
Figure 7D:
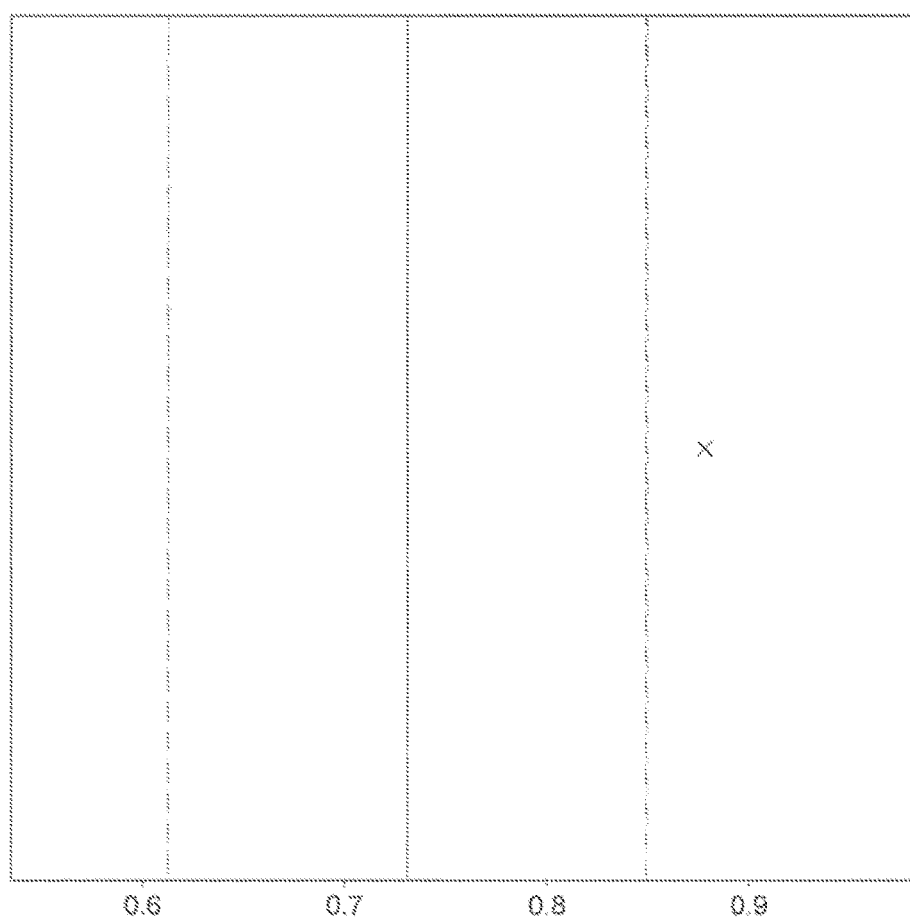
FIG. 7D shows the docetaxel and anthracycline (TxA) regimen with pairs of probes.
Figure 8A:
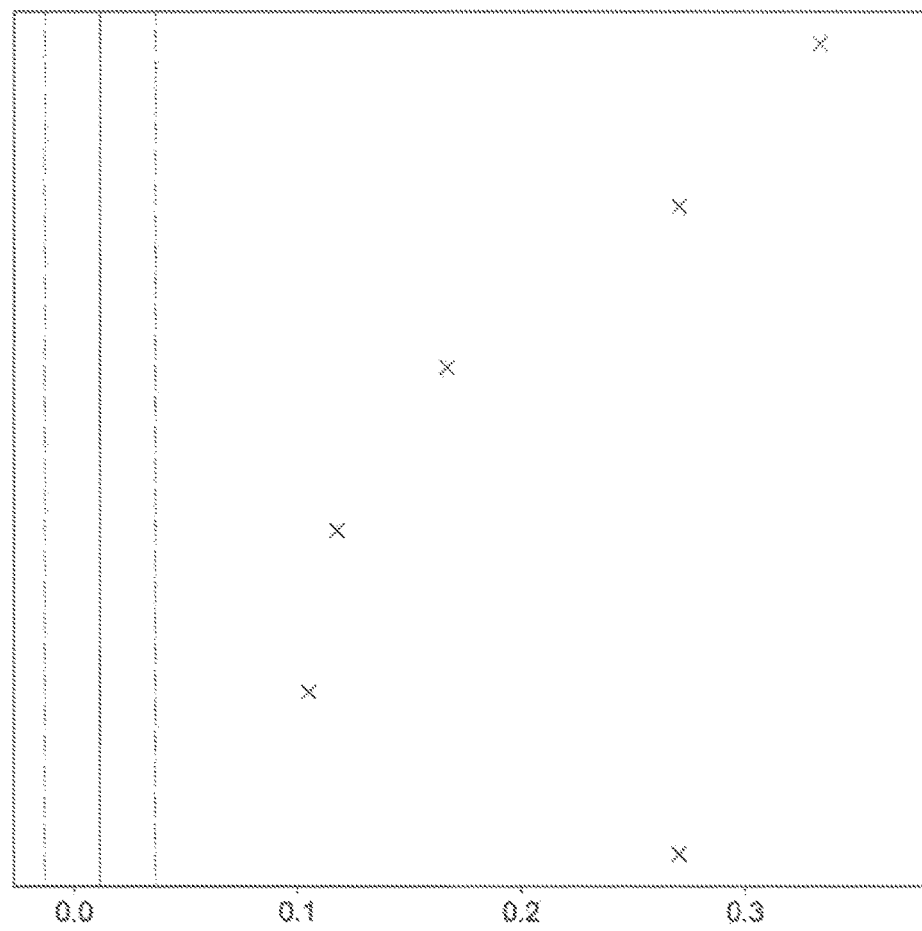
FIG. 8A shows the paclitaxel and anthracycline (TA) regimen with individual probes.
Figure 8B:
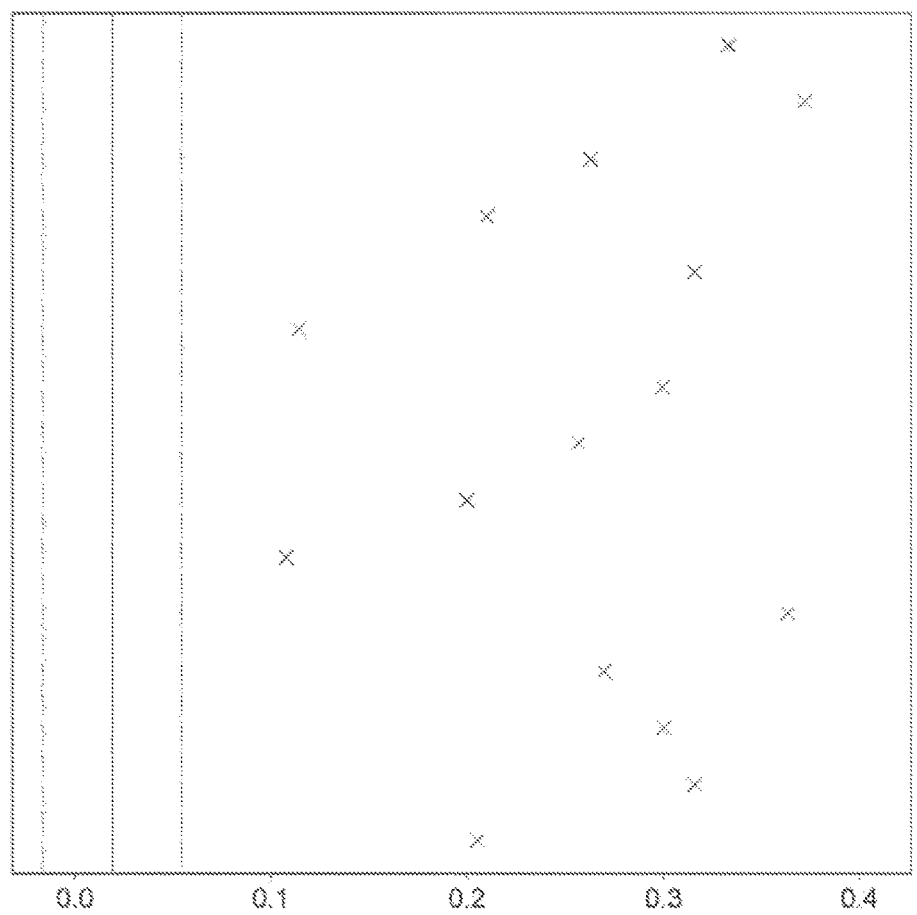
FIG. 8B shows the paclitaxel and anthracycline (TA) regimen with pairs of probes.
Figure 8C:
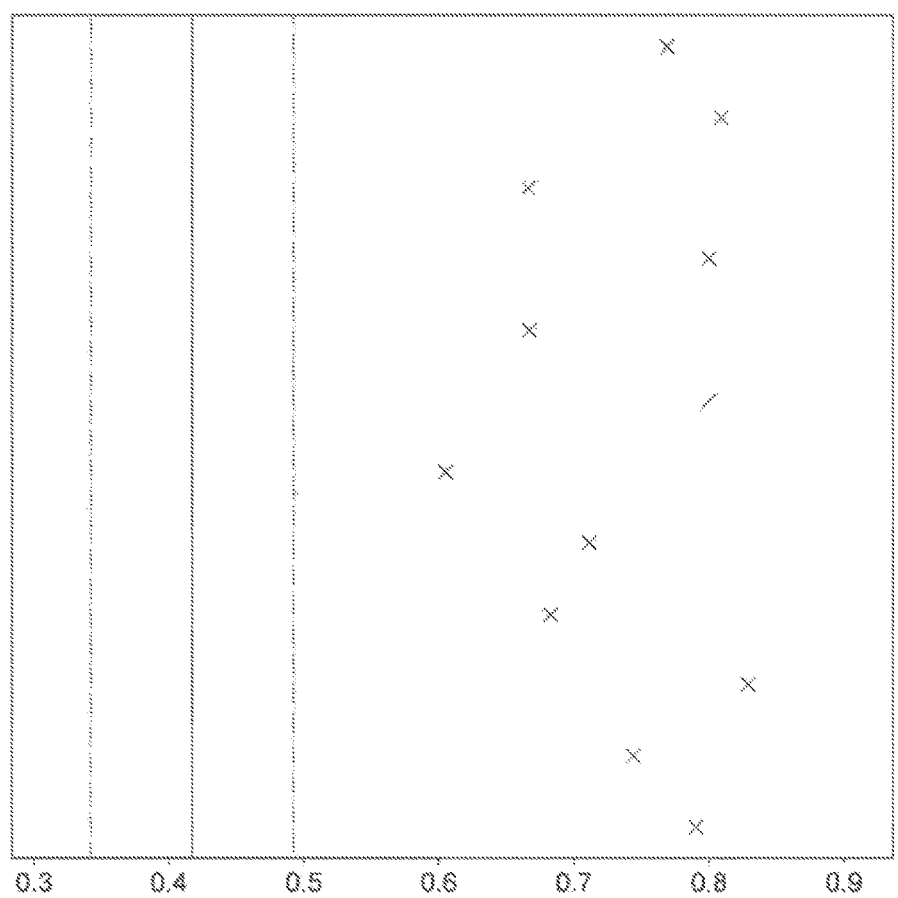
FIG. 8C shows the docetaxel and anthracycline (TxA) regimen with individual probes.
Figure 8D:
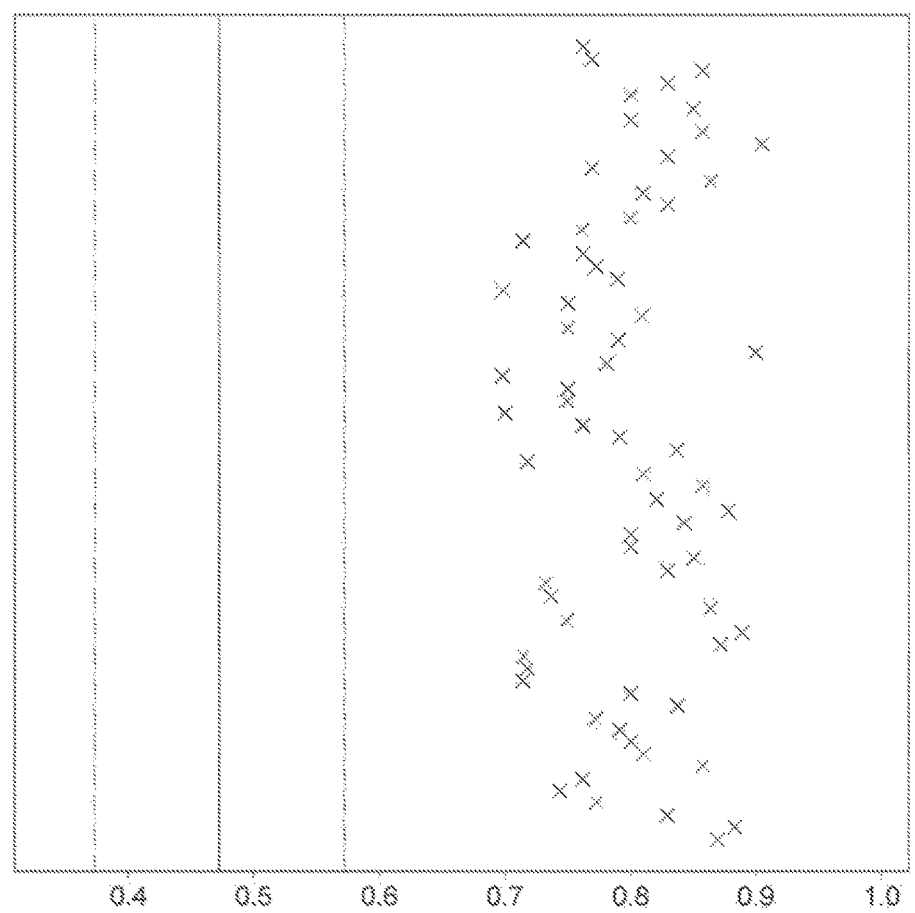
FIG. 8D shows the docetaxel and anthracycline (TxA) regimen with pairs of probes.

For the group of HER2-negative patients (FIGS. 6A-F), in regimen A, there was a pair of probes sitting inside the 95% CI, which was the pair C11orf17 (219953_s_at) and TAF6L (213211_s_at). (FIG. 6B). In regimen TxA, there was also a pair inside the 95% CI, which was AURKA (204092_s_at) and MTPAP (218947_s_at) (FIG. 6F).

Tables 40-43 show the f-scores of models of the group consisting of HER2-negative, ER-negative patients for: TA regimen with single probes (Table 40, FIG. 7A), TA regimen with pairs of probes (Table 41, FIG. 7B), TxA regimen with single probes (Table 42, FIG. 7C), and TxA regimen with pairs of probes (Table 43, FIG. 7D).

TABLE 40

F-Scores for the Group Consisting of HER2-Negative, ER-Negative Patients, TA Regimen, Single Probes

| Gene | Probe | F-score |
|---|---|---|
| NFIB | 213033_s_at | 0.568 |
| NFIB | 209289_at | 0.641 |
| MTAP | 211363_s_at | 0.571 |
| SNAPC3 | 210465_s_at | 0.542 |
| RANBP9 | 202583_s_at | 0.5 |
| NFIB | 213032_at | 0.581 |
| COIL | 203653_s_at | 0.519 |
| FAM86B1 | 65585_at | 0.469 |
| ITGA6 | 215177_s_at | 0.618 |
| S100P | 204351_at | 0.601 |
| RANBP1 | 202483_s_at | 0.553 |
| PRSS16 | 208165_s_at | 0.514 |
| SMARCA2 | 206542_s_at | 0.619 |
| STK24 | 208854_s_at | 0.471 |

TABLE 41

F-Scores for the Group Consisting of HER2-Negative, ER-Negative Patients, TA Regimen, Pairs of Probes

| Gene 1 | Probe 1 | Gene 2 | Probe 2 | F-score |
|---|---|---|---|---|
| NFIB | 213033_s_at | NFIB | 209289_at | 0.654 |
| NFIB | 213033_s_at | MTAP | 211363_s_at | 0.685 |
| NFIB | 213033_s_at | SNAPC3 | 210465_s_at | 0.618 |
| NFIB | 213033_s_at | RANBP9 | 202583_s_at | 0.688 |
| NFIB | 213033_s_at | NFIB | 213032_at | 0.64 |
| NFIB | 213033_s_at | COIL | 203653_s_at | 0.658 |
| NFIB | 213033_s_at | FAM86B1 | 65585_at | 0.667 |
| NFIB | 213033_s_at | ITGA6 | 215177_s_at | 0.645 |
| NFIB | 213033_s_at | S100P | 204351_at | 0.62 |
| NFIB | 213033_s_at | RANBP1 | 202483_s_at | 0.627 |
| NFIB | 213033_s_at | PRSS16 | 208165_s_at | 0.649 |
| NFIB | 213033_s_at | SMARCA2 | 206542_s_at | 0.612 |
| NFIB | 213033_s_at | STK24 | 208854_s_at | 0.618 |
| NFIB | 209289_at | MTAP | 211363_s_at | 0.728 |
| NFIB | 209289_at | SNAPC3 | 210465_s_at | 0.635 |
| NFIB | 209289_at | RANBP9 | 202583_s_at | 0.658 |
| NFIB | 209289_at | NFIB | 213032_at | 0.645 |
| NFIB | 209289_at | COIL | 203653_s_at | 0.649 |
| NFIB | 209289_at | FAM86B1 | 65585_at | 0.654 |
| NFIB | 209289_at | ITGA6 | 215177_s_at | 0.680 |
| NFIB | 209289_at | S100P | 204351_at | 0.709 |
| NFIB | 209289_at | RANBP1 | 202483_s_at | 0.675 |
| NFIB | 209289_at | PRSS16 | 208165_s_at | 0.658 |
| NFIB | 209289_at | SMARCA2 | 206542_s_at | 0.688 |
| NFIB | 209289_at | STK24 | 208854_s_at | 0.667 |
| MTAP | 211363_s_at | SNAPC3 | 210465_s_at | 0.632 |
| MTAP | 211363_s_at | RANBP9 | 202583_s_at | 0.680 |
| MTAP | 211363_s_at | NFIB | 213032_at | 0.725 |
| MTAP | 211363_s_at | COIL | 203653_s_at | 0.591 |
| MTAP | 211363_s_at | FAM86B1 | 65585_at | 0.675 |
| MTAP | 211363_s_at | ITGA6 | 215177_s_at | 0.654 |
| MTAP | 211363_s_at | S100P | 204351_at | 0.649 |
| MTAP | 211363_s_at | RANBP1 | 202483_s_at | 0.631 |
| MTAP | 211363_s_at | PRSS16 | 208165_s_at | 0.597 |
| MTAP | 211363_s_at | SMARCA2 | 206542_s_at | 0.667 |
| MTAP | 211363_s_at | STK24 | 208854_s_at | 0.632 |
| SNAPC3 | 210465_s_at | RANBP9 | 202583_s_at | 0.662 |
| SNAPC3 | 210465_s_at | NFIB | 213032_at | 0.667 |
| SNAPC3 | 210465_s_at | COIL | 203653_s_at | 0.662 |
| SNAPC3 | 210465_s_at | FAM86B1 | 65585_at | 0.630 |
| SNAPC3 | 210465_s_at | ITGA6 | 215177_s_at | 0.617 |
| SNAPC3 | 210465_s_at | S100P | 204351_at | 0.649 |
| SNAPC3 | 210465_s_at | RANBP1 | 202483_s_at | 0.64 |
| SNAPC3 | 210465_s_at | PRSS16 | 208165_s_at | 0.689 |
| SNAPC3 | 210465_s_at | SMARCA2 | 206542_s_at | 0.634 |
| SNAPC3 | 210465_s_at | STK24 | 208854_s_at | 0.648 |
| RANBP9 | 202583_s_at | NFIB | 213032_at | 0.699 |
| RANBP9 | 202583_s_at | COIL | 203653_s_at | 0.671 |
| RANBP9 | 202583_s_at | FAM86B1 | 65585_at | 0.667 |
| RANBP9 | 202583_s_at | ITGA6 | 215177_s_at | 0.714 |

TABLE 41-continued

F-Scores for the Group Consisting of HER2-Negative,
ER-Negative Patients, TA Regimen, Pairs of Probes

| Gene 1 | Probe 1 | Gene 2 | Probe 2 | F-score |
|---|---|---|---|---|
| RANBP9 | 202583_s_at | S100P | 204351_at | 0.634 |
| RANBP9 | 202583_s_at | RANBP1 | 202483_s_at | 0.64 |
| RANBP9 | 202583_s_at | PRSS16 | 208165_s_at | 0.604 |
| RANBP9 | 202583_s_at | SMARCA2 | 206542_s_at | 0.742 |
| RANBP9 | 202583_s_at | STK24 | 208854_s_at | 0.576 |
| NFIB | 213032_at | COIL | 203653_s_at | 0.667 |
| NFIB | 213032_at | FAM86B1 | 65585_at | 0.653 |
| NFIB | 213032_at | ITGA6 | 215177_s_at | 0.723 |
| NFIB | 213032_at | S100P | 204351_at | 0.667 |
| NFIB | 213032_at | RANBP1 | 202483_s_at | 0.671 |
| NFIB | 213032_at | PRSS16 | 208165_s_at | 0.632 |
| NFIB | 213032_at | SMARCA2 | 206542_s_at | 0.710 |
| NFIB | 213032_at | STK24 | 208854_s_at | 0.667 |
| COIL | 203653_s_at | FAM86B1 | 65585_at | 0.638 |
| COIL | 203653_s_at | ITGA6 | 215177_s_at | 0.625 |
| COIL | 203653_s_at | S100P | 204351_at | 0.639 |
| COIL | 203653_s_at | RANBP1 | 202483_s_at | 0.597 |
| COIL | 203653_s_at | PRSS16 | 208165_s_at | 0.671 |
| COIL | 203653_s_at | SMARCA2 | 206542_s_at | 0.613 |
| COIL | 203653_s_at | STK24 | 208854_s_at | 0.653 |
| FAM86B1 | 65585_at | ITGA6 | 215177_s_at | 0.703 |
| FAM86B1 | 65585_at | S100P | 204351_at | 0.653 |
| FAM86B1 | 65585_at | RANBP1 | 202483_s_at | 0.644 |
| FAM86B1 | 65585_at | PRSS16 | 208165_s_at | 0.633 |
| FAM86B1 | 65585_at | SMARCA2 | 206542_s_at | 0.561 |
| FAM86B1 | 65585_at | STK24 | 208854_s_at | 0.629 |
| ITGA6 | 215177_s_at | S100P | 204351_at | 0.667 |
| ITGA6 | 215177_s_at | RANBP1 | 202483_s_at | 0.662 |
| ITGA6 | 215177_s_at | PRSS16 | 208165_s_at | 0.627 |
| ITGA6 | 215177_s_at | SMARCA2 | 206542_s_at | 0.653 |
| ITGA6 | 215177_s_at | STK24 | 208854_s_at | 0.658 |
| S100P | 204351_at | RANBP1 | 202483_s_at | 0.727 |
| S100P | 204351_at | PRSS16 | 208165_s_at | 0.616 |
| S100P | 204351_at | SMARCA2 | 206542_s_at | 0.684 |
| S100P | 204351_at | STK24 | 208854_s_at | 0.615 |
| RANBP1 | 202483_s_at | PRSS16 | 208165_s_at | 0.641 |
| RANBP1 | 202483_s_at | SMARCA2 | 206542_s_at | 0.701 |
| RANBP1 | 202483_s_at | STK24 | 208854_s_at | 0.616 |
| PRSS16 | 208165_s_at | SMARCA2 | 206542_s_at | 0.667 |
| PRSS16 | 208165_s_at | STK24 | 208854_s_at | 0.556 |
| SMARCA2 | 206542_s_at | STK24 | 208854_s_at | 0.623 |

TABLE 42

F-Scores for the Group Consisting of HER2-Negative,
ER-Negative Patients, TxA Regimen, Single Probes

| Gene | Probe | F-score |
|---|---|---|
| TSPYL5 | 213122_at | 0.871 |
| SRI | 208920_at | 0.8 |

TABLE 43

F-Scores for the Group Consisting of HER2-Negative,
ER-Negative Patients, TxA Regimen, Pairs of Probes

| Gene 1 | Probe 1 | Gene 2 | Probe 2 | F-score |
|---|---|---|---|---|
| TSPYL5 | 213122_at | SRI | 208920_at | 0.878 |

Tables 44-47 show the f-scores of models of the group consisting of HER2-negative, ER-positive patients for: TA regimen with single probes (Table 44, FIG. 8A), TA regimen with pairs of probes (Table 45, FIG. 8B), TxA regimen with single probes (Table 46, FIG. 8C), and TxA regimen with pairs of probes (Table 47, FIG. 8D).

TABLE 44

F-Scores for the Group Consisting of HER2-Negative,
ER-Positive Patients, TA Regimen, Single Probes

| Gene | Probe | F-score |
|---|---|---|
| LRP12 | 219631_at | 0.270 |
| CENPF | 207828_s_at | 0.105 |
| TUBD1 | 210389_x_at | 0.118 |
| KIAA1324 | 221874_at | 0.167 |
| LRP12 | 220253_s_at | 0.270 |
| TTK | 204822_at | 0.333 |

TABLE 45

F-Scores for the Group Consisting of HER2-Negative,
ER-Positive Patients, TA Regimen, Pairs of Probes

| Gene 1 | Probe 1 | Gene 2 | Probe 2 | F-score |
|---|---|---|---|---|
| LRP12 | 219631_at | CENPF | 207828_s_at | 0.205 |
| LRP12 | 219631_at | TUBD1 | 210389_x_at | 0.316 |
| LRP12 | 219631_at | KIAA1324 | 221874_at | 0.3 |
| LRP12 | 219631_at | LRP12 | 220253_s_at | 0.270 |
| LRP12 | 219631_at | TTK | 204822_at | 0.364 |
| CENPF | 207828_s_at | TUBD1 | 210389_x_at | 0.108 |
| CENPF | 207828_s_at | KIAA1324 | 221874_at | 0.2 |
| CENPF | 207828_s_at | LRP12 | 220253_s_at | 0.256 |
| CENPF | 207828_s_at | TTK | 204822_at | 0.3 |
| TUBD1 | 210389_x_at | KIAA1324 | 221874_at | 0.114 |
| TUBD1 | 210389_x_at | LRP12 | 220253_s_at | 0.316 |
| TUBD1 | 210389_x_at | TTK | 204822_at | 0.211 |
| KIAA1324 | 221874_at | LRP12 | 220253_s_at | 0.263 |
| KIAA1324 | 221874_at | TTK | 204822_at | 0.372 |
| LRP12 | 220253_s_at | TTK | 204822_at | 0.333 |

TABLE 46

F-Scores for the Group Consisting of HER2-Negative,
ER-Positive Patients, TxA Regimen, Single Probes

| Gene | Probe | F-score |
|---|---|---|
| DBF4 | 204244_s_at | 0.791 |
| DEK | 200934_at | 0.744 |
| CDC25B | 201853_s_at | 0.829 |
| CCNA2 | 203418_at | 0.683 |
| DLGAP5 | 203764_at | 0.711 |
| MCM2 | 202107_s_at | 0.605 |
| CDKN2C | 204159_at | 0.8 |
| FHL1 | 210298_x_at | 0.667 |
| SIRT3 | 221913_at | 0.8 |
| GTSE1 | 215942_s_at | 0.667 |
| PCNA | 201202_at | 0.810 |
| CCNE2 | 205034_at | 0.769 |

TABLE 47

F-Scores for the Group Consisting of HER2-Negative,
ER-Positive Patients, TxA Regimen, Pairs of Probes

| Gene 1 | Probe 1 | Gene 2 | Probe 2 | F-score |
|---|---|---|---|---|
| DBF4 | 204244_s_at | DEK | 200934_at | 0.870 |
| DBF4 | 204244_s_at | CDC25B | 201853_s_at | 0.884 |
| DBF4 | 204244_s_at | CCNA2 | 203418_at | 0.829 |
| DBF4 | 204244_s_at | DLGAP5 | 203764_at | 0.773 |
| DBF4 | 204244_s_at | MCM2 | 202107_s_at | 0.744 |
| DBF4 | 204244_s_at | CDKN2C | 204159_at | 0.762 |
| DBF4 | 204244_s_at | FHL1 | 210298_x_at | 0.857 |
| DBF4 | 204244_s_at | SIRT3 | 221913_at | 0.810 |
| DBF4 | 204244_s_at | GTSE1 | 215942_s_at | 0.8 |
| DBF4 | 204244_s_at | PCNA | 201202_at | 0.791 |
| DBF4 | 204244_s_at | CCNE2 | 205034_at | 0.773 |

TABLE 47-continued

F-Scores for the Group Consisting of HER2-Negative,
ER-Positive Patients, TxA Regimen, Pairs of Probes

| Gene 1 | Probe 1 | Gene 2 | Probe 2 | F-score |
|---|---|---|---|---|
| DEK | 200934_at | CDC25B | 201853_s_at | 0.837 |
| DEK | 200934_at | CCNA2 | 203418_at | 0.8 |
| DEK | 200934_at | DLGAP5 | 203764_at | 0.714 |
| DEK | 200934_at | MCM2 | 202107_s_at | 0.718 |
| DEK | 200934_at | CDKN2C | 204159_at | 0.714 |
| DEK | 200934_at | FHL1 | 210298_x_at | 0.872 |
| DEK | 200934_at | SIRT3 | 221913_at | 0.889 |
| DEK | 200934_at | GTSE1 | 215942_s_at | 0.75 |
| DEK | 200934_at | PCNA | 201202_at | 0.864 |
| DEK | 200934_at | CCNE2 | 205034_at | 0.737 |
| CDC25B | 201853_s_at | CCNA2 | 203418_at | 0.732 |
| CDC25B | 201853_s_at | DLGAP5 | 203764_at | 0.829 |
| CDC25B | 201853_s_at | MCM2 | 202107_s_at | 0.85 |
| CDC25B | 201853_s_at | CDKN2C | 204159_at | 0.8 |
| CDC25B | 201853_s_at | FHL1 | 210298_x_at | 0.8 |
| CDC25B | 201853_s_at | SIRT3 | 221913_at | 0.842 |
| CDC25B | 201853_s_at | GTSE1 | 215942_s_at | 0.878 |
| CDC25B | 201853_s_at | PCNA | 201202_at | 0.821 |
| CDC25B | 201853_s_at | CCNE2 | 205034_at | 0.857 |
| CCNA2 | 203418_at | DLGAP5 | 203764_at | 0.810 |
| CCNA2 | 203418_at | MCM2 | 202107_s_at | 0.718 |
| CCNA2 | 203418_at | CDKN2C | 204159_at | 0.837 |
| CCNA2 | 203418_at | FHL1 | 210298_x_at | 0.791 |
| CCNA2 | 203418_at | SIRT3 | 221913_at | 0.762 |
| CCNA2 | 203418_at | GTSE1 | 215942_s_at | 0.7 |
| CCNA2 | 203418_at | PCNA | 201202_at | 0.75 |
| CCNA2 | 203418_at | CCNE2 | 205034_at | 0.75 |
| DLGAP5 | 203764_at | MCM2 | 202107_s_at | 0.698 |
| DLGAP5 | 203764_at | CDKN2C | 204159_at | 0.780 |
| DLGAP5 | 203764_at | FHL1 | 210298_x_at | 0.9 |
| DLGAP5 | 203764_at | SIRT3 | 221913_at | 0.791 |
| DLGAP5 | 203764_at | GTSE1 | 215942_s_at | 0.75 |
| DLGAP5 | 203764_at | PCNA | 201202_at | 0.810 |
| DLGAP5 | 203764_at | CCNE2 | 205034_at | 0.75 |
| MCM2 | 202107_s_at | CDKN2C | 204159_at | 0.698 |
| MCM2 | 202107_s_at | FHL1 | 210298_x_at | 0.789 |
| MCM2 | 202107_s_at | SIRT3 | 221913_at | 0.773 |
| MCM2 | 202107_s_at | GTSE1 | 215942_s_at | 0.762 |
| MCM2 | 202107_s_at | PCNA | 201202_at | 0.714 |
| MCM2 | 202107_s_at | CCNE2 | 205034_at | 0.762 |
| CDKN2C | 204159_at | FHL1 | 210298_x_at | 0.8 |
| CDKN2C | 204159_at | SIRT3 | 221913_at | 0.829 |
| CDKN2C | 204159_at | GTSE1 | 215942_s_at | 0.810 |
| CDKN2C | 204159_at | PCNA | 201202_at | 0.864 |
| CDKN2C | 204159_at | CCNE2 | 205034_at | 0.769 |
| FHL1 | 210298_x_at | SIRT3 | 221913_at | 0.829 |
| FHL1 | 210298_x_at | GTSE1 | 215942_s_at | 0.905 |
| FHL1 | 210298_x_at | PCNA | 201202_at | 0.857 |
| FHL1 | 210298_x_at | CCNE2 | 205034_at | 0.8 |
| SIRT3 | 221913_at | GTSE1 | 215942_s_at | 0.85 |
| SIRT3 | 221913_at | PCNA | 201202_at | 0.8 |
| SIRT3 | 221913_at | CCNE2 | 205034_at | 0.829 |
| GTSE1 | 215942_s_at | PCNA | 201202_at | 0.857 |
| GTSE1 | 215942_s_at | CCNE2 | 205034_at | 0.769 |
| PCNA | 201202_at | CCNE2 | 205034_at | 0.762 |

Figure 9A:
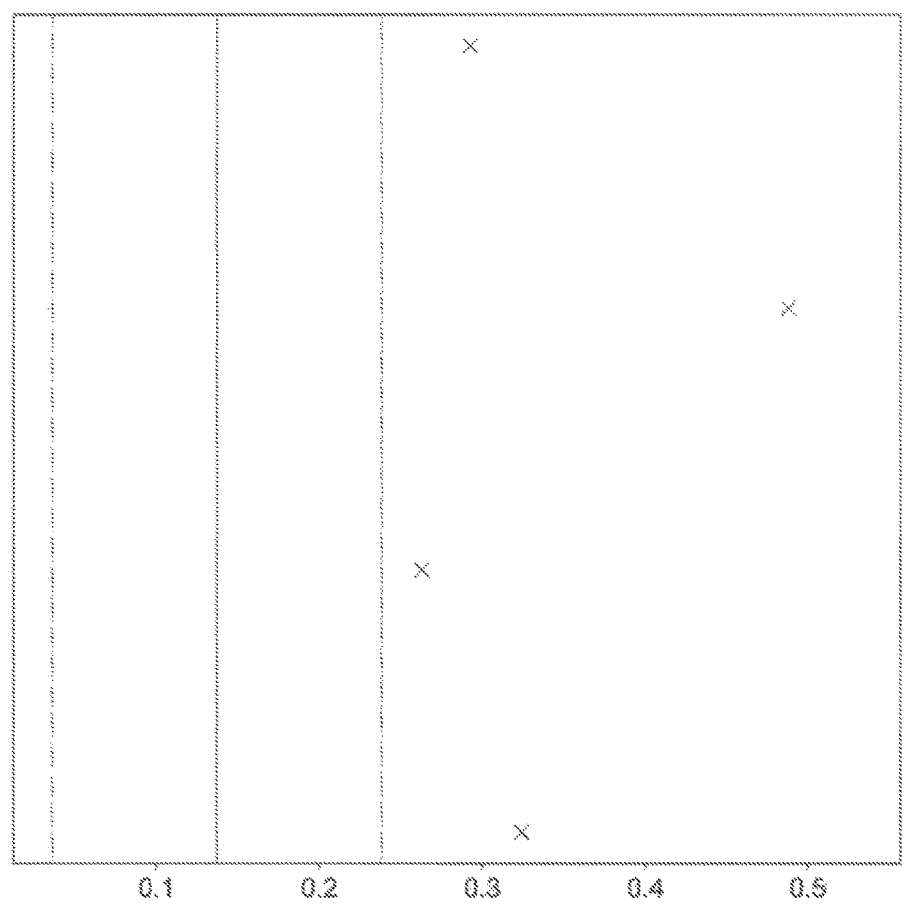
FIG. 9A shows the paclitaxel and anthracycline (TA) regimen with individual probes.
Figure 9B:
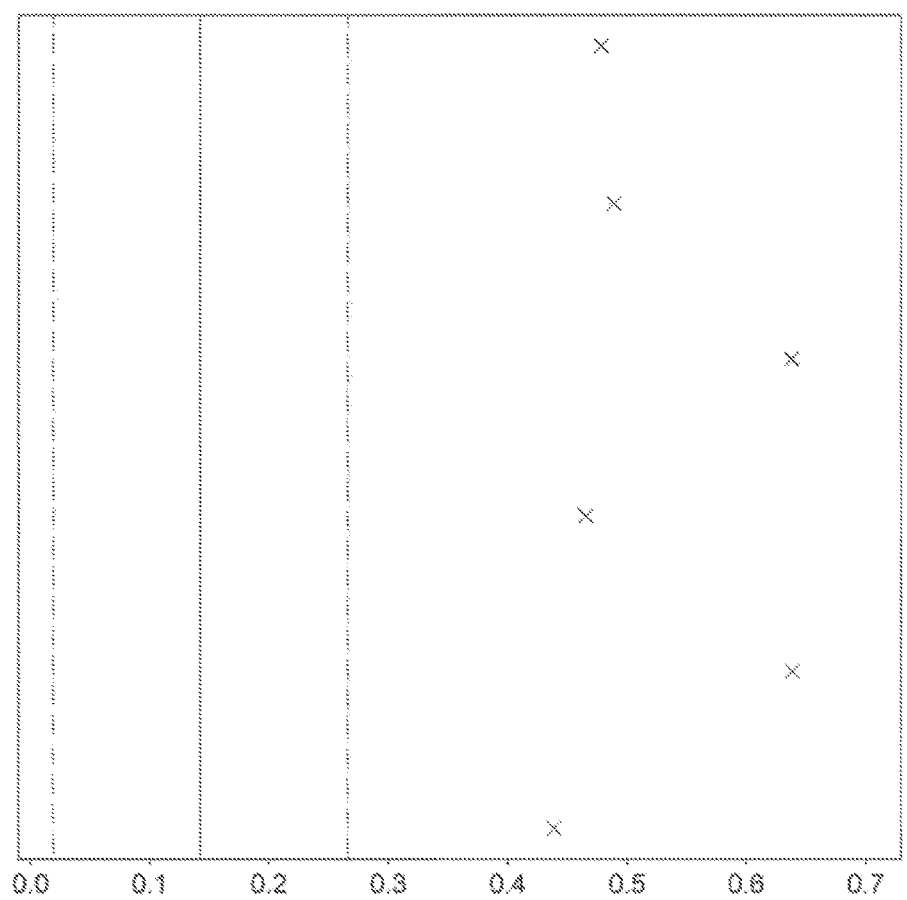
FIG. 9B shows the paclitaxel and anthracycline (TA) regimen with pairs of probes.
Figure 9C:
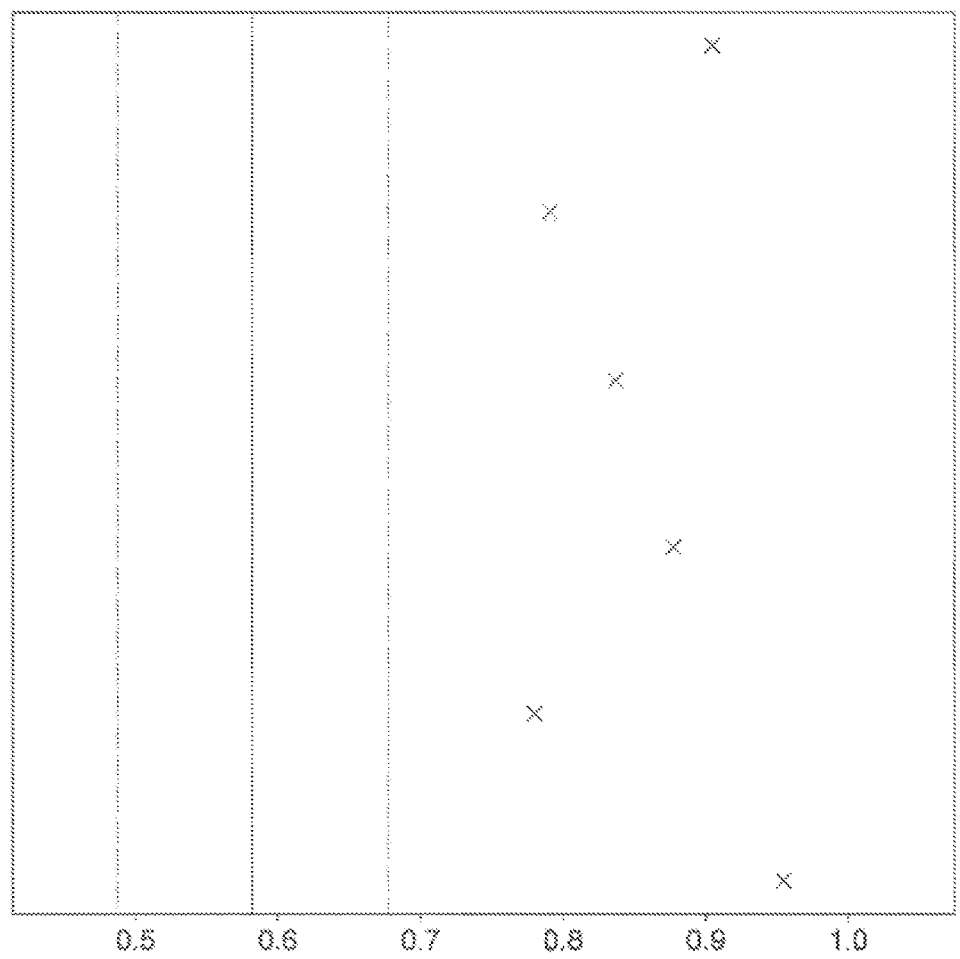
FIG. 9C shows the docetaxel and anthracycline (TxA) regimen with individual probes.
Figure 9D:
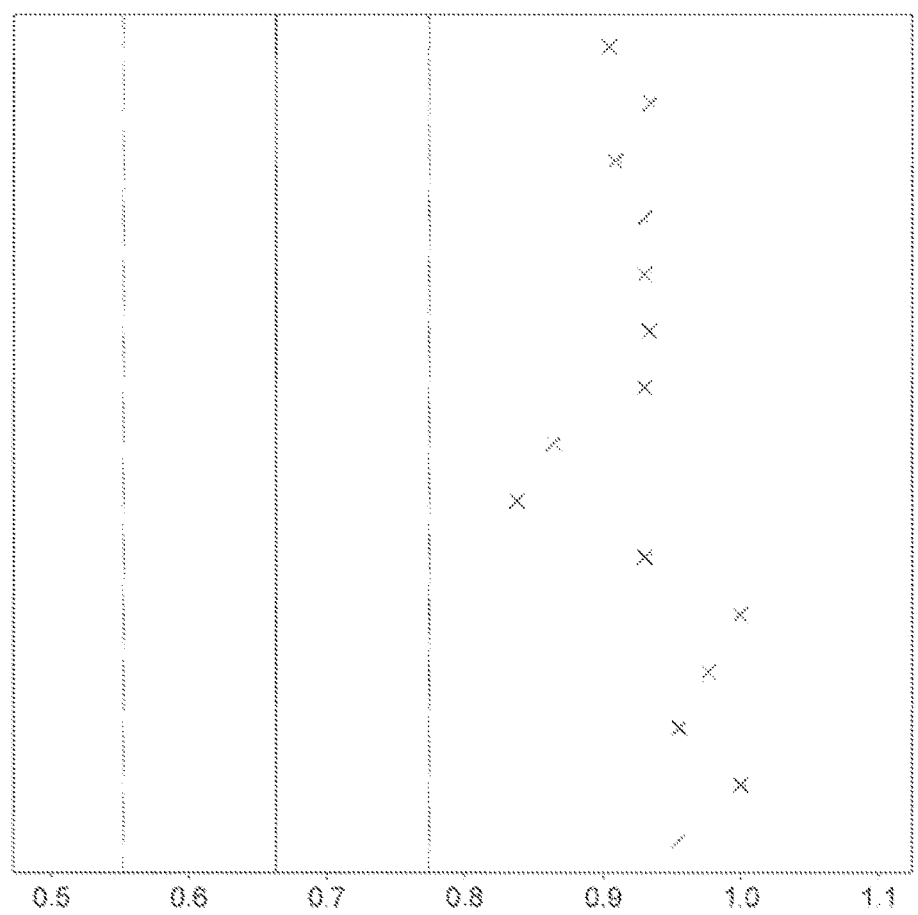
FIG. 9D shows the docetaxel and anthracycline (TxA) regimen with pairs of probes.

Tables 48-51 show the f-scores of models of the group consisting of HER2-negative, lymph node-negative patients for: TA regimen with single probes (Table 48, FIG. 9A), TA regimen with pairs of probes (Table 49, FIG. 9B), TxA regimen with single probes (Table 50, FIG. 9C). and TxA regimen with pairs of probes (Table 51. FIG. 9D).

TABLE 48

F-Scores for the Group Consisting of HER2-Negative,
Lymph Node-Negative, TA Regimen, Single Probes

| Gene | Probe | F-score |
|---|---|---|
| CHD3 | 208807_s_at | 0.324 |
| CAP1 | 200625_s_at | 0.263 |

TABLE 48-continued

F-Scores for the Group Consisting of HER2-Negative,
Lymph Node-Negative, TA Regimen, Single Probes

| Gene | Probe | F-score |
|---|---|---|
| GPM6B | 209170_s_at | 0.488 |
| GUSBP3 | 215599_at | 0.293 |

TABLE 49

F-Scores for the Group Consisting of HER2-Negative,
Lymph Node-Negative, TA Regimen, Pairs of Probes

| Gene 1 | Probe 1 | Gene 2 | Probe 2 | F-score |
|---|---|---|---|---|
| CHD3 | 208807_s_at | CAP1 | 200625_s_at | 0.439 |
| CHD3 | 208807_s_at | GPM6B | 209170_s_at | 0.638 |
| CHD3 | 208807_s_at | GUSBP3 | 215599_at | 0.465 |
| CAP1 | 200625_s_at | GPM6B | 209170_s_at | 0.638 |
| CAP1 | 200625_s_at | GUSBP3 | 215599_at | 0.489 |
| GPM6B | 209170_s_at | GUSBP3 | 215599_at | 0.478 |

TABLE 50

F-Scores for the Group Consisting of HER2-Negative,
Lymph Node-Negative, TxA Regimen, Single Probes

| Gene | Probe | F-score |
|---|---|---|
| CDKN2C | 204159_at | 0.955 |
| GNAI3 | 201180_s_at | 0.780 |
| LMO4 | 209205_s_at | 0.878 |
| PSRC1 | 201896_s_at | 0.837 |
| USP1 | 202413_s_at | 0.791 |
| STK38 | 202951_at | 0.905 |

TABLE 51

F-Scores for the Group Consisting of HER2-Negative,
Lymph Node-Negative, TxA Regimen, Pairs of Probes

| Gene 1 | Probe 1 | Gene 2 | Probe 2 | F-score |
|---|---|---|---|---|
| CDKN2C | 204159_at | GNAI3 | 201180_s_at | 0.955 |
| CDKN2C | 204159_at | LMO4 | 209205_s_at | 1 |
| CDKN2C | 204159_at | PSRC1 | 201896_s_at | 0.955 |
| CDKN2C | 204159_at | USP1 | 202413_s_at | 0.977 |
| CDKN2C | 204159_at | STK38 | 202951_at | 1 |
| GNAI3 | 201180_s_at | LMO4 | 209205_s_at | 0.930 |
| GNAI3 | 201180_s_at | PSRC1 | 201896_s_at | 0.837 |
| GNAI3 | 201180_s_at | USP1 | 202413_s_at | 0.864 |
| GNAI3 | 201180_s_at | STK38 | 202951_at | 0.930 |
| LMO4 | 209205_s_at | PSRC1 | 201896_s_at | 0.933 |
| LMO4 | 209205_s_at | USP1 | 202413_s_at | 0.930 |
| LMO4 | 209205_s_at | STK38 | 202951_at | 0.930 |
| PSRC1 | 201896_s_at | USP1 | 202413_s_at | 0.909 |
| PSRC1 | 201896_s_at | STK38 | 202951_at | 0.933 |
| USP1 | 202413_s_at | STK38 | 202951_at | 0.905 |

Tables 52-55 show the f-scores of models of the group consisting of HER2-negative, lymph node-positive patients for: TA regimen with single probes (Table 52, FIG. 10A), TA regimen with pairs of probes (Table 53, FIG. 10B), TxA regimen with single probes (Table 54, FIG. 10C), and TxA regimen with pairs of probes (Table 55, FIG. 10D).

TABLE 52

F-Scores for the Group Consisting of HER2-Negative,
Lymph Node-Positive, TA Regimen, Single Probes

| Gene | Probe | F-score |
|---|---|---|
| NFIB | 213033_s_at | 0.538 |
| NFIB | 213032_at | 0.531 |
| ROPN1B | 220425_x_at | 0.529 |

TABLE 53

F-Scores for the Group Consisting of HER2-Negative,
Lymph Node-Positive, TA Regimen, Pairs of Probes

| Gene 1 | Probe 1 | Gene 2 | Probe 2 | F-score |
|---|---|---|---|---|
| NFIB | 213033_s_at | NFIB | 213032_at | 0.566 |
| NFIB | 213033_s_at | ROPN1B | 220425_x_at | 0.538 |
| NFIB | 213032_at | ROPN1B | 220425_x_at | 0.64 |

TABLE 54

F-Scores for the Group Consisting of HER2-Negative,
Lymph Node-Positive, TxA Regimen, Single Probes

| Gene | Probe | F-score |
|---|---|---|
| TPX2 | 210052_s_at | 0.767 |
| BAT2L1 | 212068_s_at | 0.741 |
| PMP22 | 210139_s_at | 0.775 |
| PTTG1 | 203554_x_at | 0.759 |
| NME5 | 206197_at | 0.617 |
| CENPA | 204962_s_at | 0.78 |
| BANK1 | 219667_s_at | 0.75 |

TABLE 55

F-Scores for the Group Consisting of HER2-Negative,
Lymph Node-Positive, TxA Regimen, Pairs of Probes

| Gene 1 | Probe 1 | Gene 2 | Probe 2 | F-score |
|---|---|---|---|---|
| TPX2 | 210052_s_at | BAT2L1 | 212068_s_at | 0.835 |
| TPX2 | 210052_s_at | PMP22 | 210139_s_at | 0.864 |
| TPX2 | 210052_s_at | PTTG1 | 203554_x_at | 0.831 |
| TPX2 | 210052_s_at | NME5 | 206197_at | 0.825 |
| TPX2 | 210052_s_at | CENPA | 204962_s_at | 0.753 |
| TPX2 | 210052_s_at | BANK1 | 219667_s_at | 0.840 |
| BAT2L1 | 212068_s_at | PMP22 | 210139_s_at | 0.825 |
| BAT2L1 | 212068_s_at | PTTG1 | 203554_x_at | 0.85 |
| BAT2L1 | 212068_s_at | NME5 | 206197_at | 0.683 |
| BAT2L1 | 212068_s_at | CENPA | 204962_s_at | 0.816 |
| BAT2L1 | 212068_s_at | BANK1 | 219667_s_at | 0.784 |
| PMP22 | 210139_s_at | PTTG1 | 203554_x_at | 0.833 |
| PMP22 | 210139_s_at | NME5 | 206197_at | 0.815 |
| PMP22 | 210139_s_at | CENPA | 204962_s_at | 0.853 |
| PMP22 | 210139_s_at | BANK1 | 219667_s_at | 0.867 |
| PTTG1 | 203554_x_at | NME5 | 206197_at | 0.769 |
| PTTG1 | 203554_x_at | CENPA | 204962_s_at | 0.843 |
| PTTG1 | 203554_x_at | BANK1 | 219667_s_at | 0.878 |
| NME5 | 206197_at | CENPA | 204962_s_at | 0.819 |
| NME5 | 206197_at | BANK1 | 219667_s_at | 0.734 |
| CENPA | 204962_s_at | BANK1 | 219667_s_at | 0.810 |

Figure 10A:
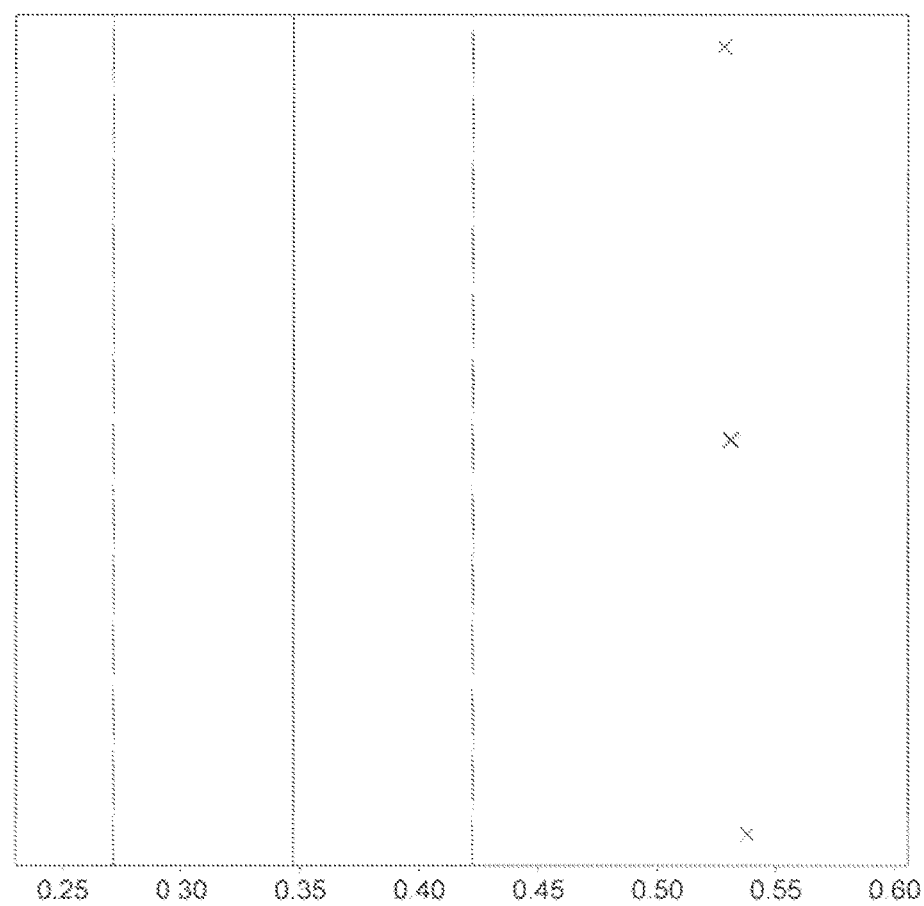
FIG. 10A shows the paclitaxel and anthracycline (TA) regimen with individual probes.
Figure 10B:
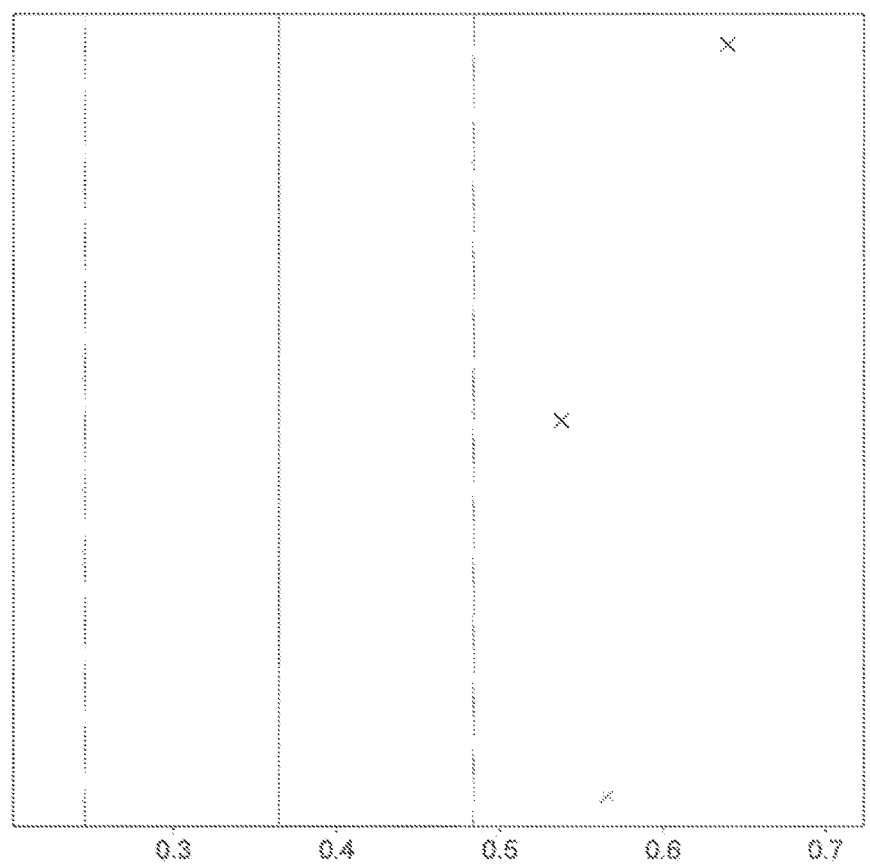
FIG. 10B shows the paclitaxel and anthracycline (TA) regimen with pairs of probes.
Figure 10C:
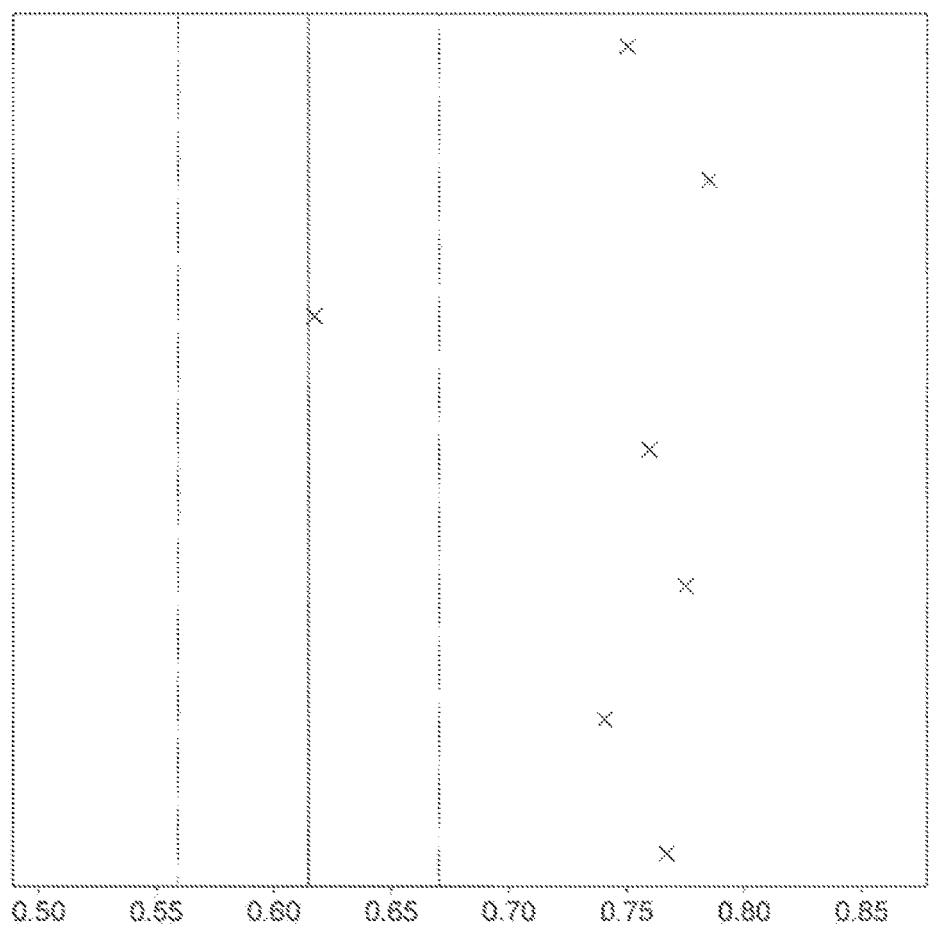
FIG. 10C shows the docetaxel and anthracycline (TxA) regimen with individual probes.
Figure 10D:
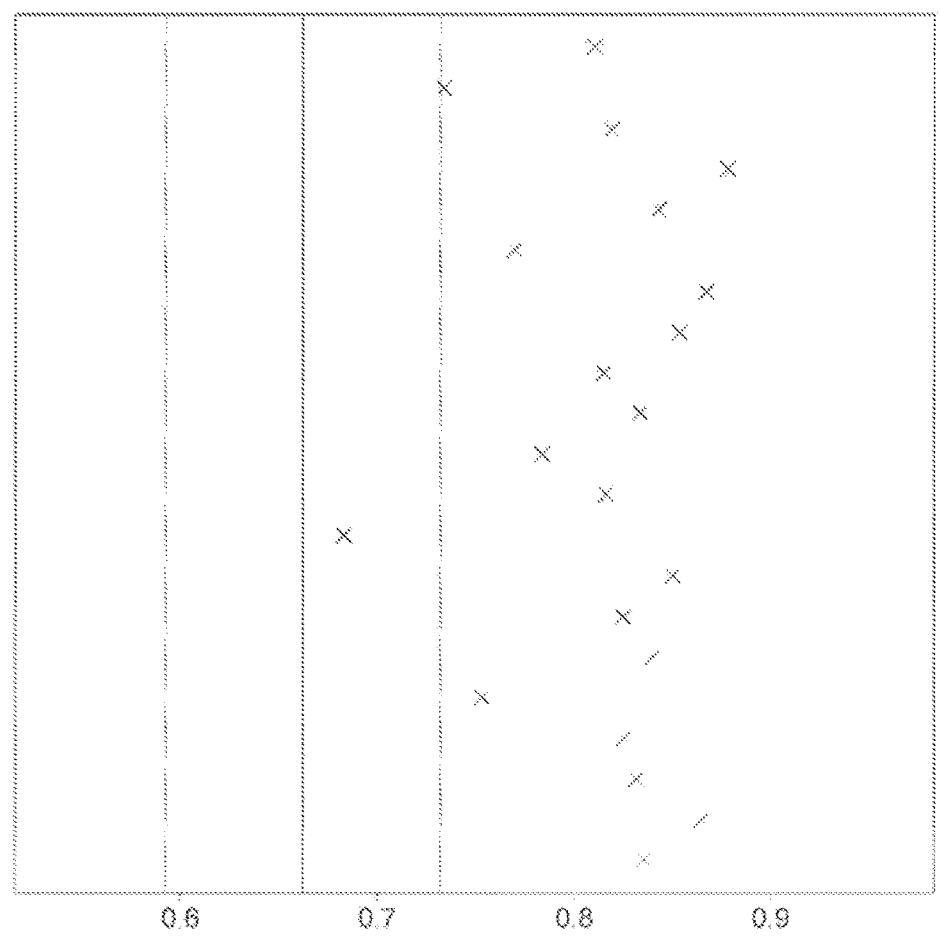
FIG. 10D shows the docetaxel and anthracycline (TxA) regimen with pairs of probes.

FIGS. 10A-D show the f-scores for the group of HER2-negative, Lymph node-positive patients. For HER2-negative, Lymph node-positive patients, in the regimen TxA, most of the single probes have much higher f-scores than the mean f-score of 300 random sets (FIG. 10C), except NME5, and most of the probe pairs have much higher f-scores than the mean f-score of 300 random sets, except BAT2L1 and NME5 (FIG. 10D).

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

REFERENCES

ALBAIN, K. S., et al. Prognostic and predictive value of the 21-gene recurrence score assay in postmenopausal women with node-positive, oestrogen-receptor-positive breast cancer on chemotherapy: a retrospective analysis of a randomised trial. Lancet Oncol 2010; 11:55-65.

BARRETT, T., et al. NCBI GEO: archive for functional genomics data sets—update. Nucleic Acids Res 2013; 41:D991-5.

BUYSE, M., et al. Validation and clinical utility of a 70-gene prognostic signature for women with node-negative breast cancer. J Natl Cancer Inst 2006; 98:1183-92.

CALLE, M. L., et al. AUC-RF: a new strategy for genomic profiling with random forest. Hum Hered 2011; 72:121-32.

CHAN, S., et al. Prospective randomized trial of docetaxel versus doxorubicin in patients with metastatic breast cancer. J Clin Oncol 1999; 17:2341-54.

D E LAURENTIIS, M., et al. Taxane-based combinations as adjuvant chemotherapy of early breast cancer: a meta-analysis of randomized trials. J Clin Oncol 2008; 26:44-53.

DOTAN, E., et al. Optimizing chemotherapy regimens for patients with early-stage breast cancer. Clin Breast Cancer 2010; 10 Suppl 1:E8-15.

EDGAR, R., et al. Gene Expression Omnibus: NCBI gene expression and hybridization array data repository. Nucleic Acids Res 2002; 30:207-10.

ENG-WONG, J., et al. Prediction of benefit from adjuvant treatment in patients with breast cancer. Clin Breast Cancer 2010; 10 Suppl 1:E32-7.

ESSERMAN, L. J., et al. Chemotherapy response and recurrence-free survival in neoadjuvant breast cancer depends on biomarker profiles: results from the I-SPY 1 TRIAL (CALGB 150007/150012; ACRIN 6657). Breast Cancer Res Treat 2012; 132:1049-62.

FOEKENS, J. A., et al. Multicenter validation of a gene expression-based prognostic signature in lymph node-negative primary breast cancer. J Clin Oncol 2006; 24:1665-71.

GAJRIA, D., et al. Adjuvant taxanes: more to the story. Clin Breast Cancer 2010; 10 Suppl 2:S41-9.

GRAESER, M., et al. A marker of homologous recombination predicts pathologic complete response to neoadjuvant chemotherapy in primary breast cancer. Clin Cancer Res 2010; 16:6159-68.

HARBECK, N., et al. Ten-year analysis of the prospective multicentre Chemo-N0 trial validates American Society of Clinical Oncology (ASCO)-recommended biomarkers uPA and PAI-1 for therapy decision making in node-negative breast cancer patients. Eur J Cancer 2013; 49:1825-35.

HATZIS, C., et al. A genomic predictor of response and survival following taxane- anthracycline chemotherapy for invasive breast cancer. JAMA 2011; 305:1873-81.

HESS, K. R., et al. Pharmacogenomic predictor of sensitivity to preoperative chemotherapy with paclitaxel and fluorouracil, doxorubicin, and cyclophosphamide in breast cancer. J Clin Oncol 2006; 24:4236-44.

IWAMOTO, T., et al. Gene pathways associated with prognosis and chemotherapy sensitivity in molecular subtypes of breast cancer. J Natl Cancer Inst 2011; 103:264-72.

KAUFMANN, M., et al. Recommendations from an international expert panel on the use of neoadjuvant (primary) systemic treatment of operable breast cancer: an update. J Clin Oncol 2006; 24:1940-9.

KUERER, H. M., et al. Clinical course of breast cancer patients with complete pathologic primary tumor and axillary lymph node response to doxorubicin-based neoadjuvant chemotherapy. J Clin Oncol 1999; 17:460-9.

LIPS, E. H., et al. Neoadjuvant chemotherapy in ER+ HER2− breast cancer: response prediction based on immunohistochemical and molecular characteristics. Breast Cancer Res Treat 2012; 131:827-36.

LIU, J. C., et al. Seventeen-gene signature from enriched Her2/Neu mammary tumor-initiating cells predicts clinical outcome for human HER2+:ERalpha− breast cancer. Proc Natl Acad Sci USA 2012; 109:5832-7.

LOOK, M. P., et al. Pooled analysis of prognostic impact of urokinase-type plasminogen activator and its inhibitor PAI-1 in 8377 breast cancer patients. J Natl Cancer Inst 2002; 94:116-28.

MIYAKE, T., et al. GSTP1 expression predicts poor pathological complete response to neoadjuvant chemotherapy in E R-negative breast cancer. Cancer Sci 2012; 103:913-20.

MOOK, S., et al. Individualization of therapy using Mammaprint: from development to the MINDACT Trial. Cancer Genomics Proteomics 2007; 4:147-55.

OAKMAN, C., et al. Breast cancer assessment tools and optimizing adjuvant therapy. Nat Rev Clin Oncol 2010; 7:725-32.

PAIK, S., et al. Gene expression and benefit of chemotherapy in women with node-negative, estrogen receptor-positive breast cancer. J Clin Oncol 2006; 24:3726-34.

POPOVICI, V., et al. Effect of training-sample size and classification difficulty on the accuracy of genomic predictors. Breast Cancer Res 2010; 12.

SHEN, K., et al. Cell line derived multi-gene predictor of pathologic response to neoadjuvant chemotherapy in breast cancer: a validation study on U S Oncology 02-103 clinical trial. BMC Med Genomics 2012; 5:51.

SHEN, K., et al. Cell line derived multi-gene predictor of pathologic response to neoadjuvant chemotherapy in breast cancer: a validation study on U S Oncology 02-103 clinical trial. BMC Med Genomics 2012; 5.

SLEDGE, G. W., et al. Phase III trial of doxorubicin, paclitaxel, and the combination of doxorubicin and paclitaxel as front-line chemotherapy for metastatic breast cancer: an intergroup trial (E1193). J Clin Oncol 2003; 21:588-92.

SPARANO, J. A., et al. Weekly paclitaxel in the adjuvant treatment of breast cancer. N Engl J Med 2008; 358:1663-71.

STRAYER, M. E., et al. The 70-gene signature as a response predictor for neoadjuvant chemotherapy in breast cancer. Breast Cancer Res Treat 2010; 119:551-8.

TABCHY, A., et al. Evaluation of a 30-gene paclitaxel, fluorouracil, doxorubicin, and cyclophosphamide chemotherapy response predictor in a multicenter randomized trial in breast cancer. Clinical cancer research: an official journal of the American Association for Cancer Research 2010; 16:5351-61.

TAKADA, M., et al. Predictions of the pathological response to neoadjuvant chemotherapy in patients with primary breast cancer using a data mining technique. Breast Cancer Res Treat 2012; 134:661-70.

THE CANCER GENOME ATLAS NETWORK. Comprehensive molecular portraits of human breast tumours. Nature 2012; 490:61-70.

VAN D E VIJVER, M. J., et al. A gene-expression signature as a predictor of survival in breast cancer. N Engl J Med 2002; 347:1999-2009.

VAN'T VEER, L. J., et al. Gene expression profiling predicts clinical outcome of breast cancer. Nature 2002; 415:530-6.

VERWEIJ, J., et al. Paclitaxel (Taxol) and docetaxel (Taxotere): not simply two of a kind. Ann Oncol 1994; 5:495-505.

VON MINCKWITZ, G., et al. Definition and impact of pathologic complete response on prognosis after neoadjuvant chemotherapy in various intrinsic breast cancer subtypes. J Clin Oncol 2012; 30:1796-804.

WANG, Y., et al. Gene-expression profiles to predict distant metastasis of lymph-node-negative primary breast cancer. Lancet 2005; 365:671-9.

What is claimed is:

1. A method for selecting a chemotherapy regimen for a human breast cancer subject, comprising:
    a) obtaining from said breast cancer subject a breast cancer tumor sample comprising mRNA expression products;
    b) determining mRNA expression of a plurality of genes in said sample, said genes comprises
        (i) solute carrier family 12, member 7 (SLC12A7), granzyme B (GZMB), TAF6-like RNA polymerase II (TAF6L);
        (ii) nuclear factor I/B (NFIB), glial cell differentiation regulator (METRN), rhophilin associated tail protein 1B (ROPN1B), TTK protein kinase (TTK), cyclin D1 (CCND1); and
        (iii) pituitary tumor-transforming 1 (PTTG1), H2A histone family, member Z (H2AFZ), WD repeat-containing protein 45-like (WDR45L), DEK oncogene (DEK), minichromosome maintenance complex component 2 (MCM2), ubiquitin specific peptidase 1 (USP1), chromatin licensing and DNA replication factor 1 (CDT1), transmembrane protein 97 (TMEM97), retention in endoplasmic reticulum 1 homolog (RER1), minichromosome maintenance complex component 6 (MCM6), and leucine zipper transcription factor-like 1 (LZTFL1);
    wherein mRNA expressions of the genes in group (i) are predictive of a patient's response to chemotherapy regimen I comprising anthracycline only; gene expressions of the genes in group (ii) are predictive of a patient's response to chemotherapy regimen II comprising anthracycline and paclitaxel without docetaxel; and gene expressions of the genes in group (iii) are predictive of a patient's response to chemotherapy regimen III comprising anthracycline and docetaxel without paclitaxel;
    c) using mRNA expression data from human breast cancer tumor sample from about one thousand human breast cancer patients treated with chemotherapy regimens I, II and III to construct a computer-generated model for each of chemotherapy regimens I, II and III, said models are constructed by methods comprising Random Forest modeling, wherein inputs of said models comprise genetic data of each patient and outputs from said models comprise a predicted probability of pathological complete response for each patient;
d) sorting the predicted probabilities of pathological complete response from step (c) into a plurality of probability intervals (PI), each PI contains roughly equal number of patients;
e) calculating a pathologic complete response (pCR) score for each PI, said pCR score is defined as a ratio of number of observed pathological complete response in said PI to total number of patients in said PI;
f) inputting the mRNA gene expression results from (b) into the models from (c) to obtain a predicted probability of pathological complete response for said breast cancer subject in response to each of said three chemotherapy regimens, thereby said breast cancer subject has three predicted probabilities of pathological complete response in response to chemotherapy regimens I, II and III;
g) mapping each of the three predicted probabilities of pathological complete response from (f) to one of the PI in each model, wherein each PI to which each predicted probability of pathological complete response is mapped has its corresponding pCR score, thereby said breast cancer subject has a pCR score for each of said chemotherapy regimens I, II and III; and
h) based on the three pCR scores from (g), treating said breast cancer subject with a chemotherapy regimen, wherein when the pCR score for chemotherapy regimen I is highest, said subject is treated with a chemotherapy regimen comprising anthracycline only; wherein when the pCR score for chemotherapy regimen II is highest, said subject is treated with a chemotherapy regimen comprising anthracycline and paclitaxel without docetaxel; wherein when the pCR score for chemotherapy regimen III is highest, said subject is treated with a chemotherapy regimen comprising anthracycline and docetaxel without paclitaxel.

2. The method of claim 1, wherein said mRNA expression is detected by a DNA array chip, a RNA array chip, or an oligonucleotide array chip.

* * * * *